United States Patent
Beaudet et al.

(10) Patent No.: US 6,818,401 B2
(45) Date of Patent: Nov. 16, 2004

(54) METHOD OF DETECTION AND INTERPRETATION OF MUTATIONS THROUGH EXPRESSION OR FUNCTION TESTS OF HAPLOID GENES

(75) Inventors: Arthur Beaudet, Houston, TX (US); Olaf Bodamer, Vienna (AT); Ann Killary, Houston, TX (US); Maria Mercedes Lovell, Houston, TX (US)

(73) Assignees: Board of Regents University of Texas System, Houston, TX (US); Baylor College of Medicine, Houston, TX (US)

( * ) Notice: Subject to any disclaimer, the term of this patent is extended or adjusted under 35 U.S.C. 154(b) by 0 days.

(21) Appl. No.: 09/969,861

(22) Filed: Oct. 2, 2001

(65) Prior Publication Data

US 2002/0137067 A1 Sep. 26, 2002

Related U.S. Application Data

(60) Provisional application No. 60/237,471, filed on Oct. 2, 2000.

(51) Int. Cl.[7] ............................ C12Q 1/68; C12N 5/10; C12N 15/63; C12N 15/87
(52) U.S. Cl. .......................... 435/6; 435/325; 435/455; 435/461
(58) Field of Search ................................ 435/325, 455, 435/461, 6

(56) References Cited

FOREIGN PATENT DOCUMENTS

WO    WO 00/34436 A2 * 6/2000

OTHER PUBLICATIONS

Morrison et al., Analysis of receptor clustering on cell surfaces by imaging fluorescent particles, 1994, Biophysical Journal, vol., 67, pp. 1280–1290.*
Bendich et al., Information transfer and sperm uptake by mammalian somatic cells, 1976, Prog. Nucleic Acid Research, vol. 14, pp. 43–75.*
Athwal et al., Complementation mapping in microcell hybrids: Localization of XRCC4 to 5q15–q21, 1996, Methods: A Companion to Methods in Enzymology, vol. 9, pp. 12–19.*
Haardt et al., C–terminal truncations destabilize the cystic fibrosis transmembrane conductance regulator without impairing its biogenesis, 1999, The Journal of Biological Chemistry, vol. 274, pp. 21873–21877.*
Tomizuka et al., Functional expression and germline transmission of a human chromosome fragment in chimaeric mice, 1997, Nature Genetics, vol. 16, pp. 133–143.*
Kirchgessner et al., Complementation of the radiosensitive phenotype in severe combined immunodeficient mice by human chromosome 81, 1993, Cancer Research, vol. 53, pp. 6011–6016.*
Sawami et al., Transfer of the adenosine deaminase (ADA) gene of a B–lymphoblastoid cell line (LCL) to an ADA–deficient LCL by a microcell–mediated chromosome transfer technique, 1989, ACT Haematol. Jpn., vol. 52, pp. 1033–1044.*
Sun et al., Characterization of a spice–site mutation in the gene for the LDL receptor associated with an unpredictably sever clinical phenotype in english patients with heterozygous FH, 1995, Arterioscler Thromb. Vasc. Biol., vol. 15, pp. 219–227.*

* cited by examiner

Primary Examiner—Anne-Marie Falk
Assistant Examiner—Daniel M. Sullivan
(74) Attorney, Agent, or Firm—Baker Botts LLP

(57) ABSTRACT

The present invention relates to a method for detection and interpretation of loss-of-function or gain-of-function mutations for test genes of interest. The genes of interest include those associated with inherited genetic disorders. The present invention involves the process of obtaining a sample of genetic material from an individual in the form of tissue or cells, separation of the genetic material from the cells of the individuals into haploid sets by transferring the individual chromosomal entities into a population of target cells, and monitoring the target cell population for successful transfer and expression of the test genes of interest using various functional, immunological and structural assays.

46 Claims, 49 Drawing Sheets

STATS: NOT NORMALIZED,    LISTGATING: DISABLED

| HIST | REGION ID | % | COUNT | PkPosX | PkPosY | PkCnt | HPCV | FPCVX | FPCVY | MnlX | Mn |
|---|---|---|---|---|---|---|---|---|---|---|---|
| 1 | A | 69.2 | 20000 | 59.0 | 18.2 | 92 | | 28.59 | 34.79 | 61.1 | 21.8 |

| HIST | REGION ID | % | COUNT | PkPosX | | PkCnt | HPCV | Min | Min | Max | Mn |
|---|---|---|---|---|---|---|---|---|---|---|---|
| 2 | B | 94.7 | 18933 | 0.102 | | 184 | 0.00 | 0.102 | | 2.75 | 1.18 |
|   | C | 5.6  | 1110  | 2.78  | | 47  | 86.40 | 2.75 | | 996.7 | 3.99 |
|   | D | 100  | 20000 | 0.102 | | 184 | 0.00 | 0.102 | | 1024.0 | 1.34 |
| 3 | E | 7.1  | 2044  | 0.102 | | 68  | 0.00 | 0.102 | | 2.43 | 0.970 |
|   | F | 92.9 | 26858 | 1014.8 | | 252 | ** | 2.43 | | 1024.0 | 111.8 |
|   | G | 100  | 28896 | 1014.8 | | 252 | ** | 0.102 | | 1024.0 | 104.0 |

FIG. 10D

STATS: NOT NORMALIZED,   LISTGATING: DISABLED

| HIST | REGION ID | % | COUNT | PkPosX | PkPosY | PkCnt | HPCV | FPCVX | FPCVY | MnI X | MnI Y |
|---|---|---|---|---|---|---|---|---|---|---|---|
| 1 | A | 89.6 | 12866 | 45.0 | 11.8 | 111 | | 29.34 | 36.25 | 53.4 | 16.3 |

| HIST | REGION ID | % | COUNT | PkPosX | | PkCnt | HPCV | Min | | Max | Mn |
|---|---|---|---|---|---|---|---|---|---|---|---|
| 2 | B | 99.0 | 12742 | 0.102 | | 1011 | 0.00 | 0.102 | | 2.75 | 0.486 |
| | C | 1.0 | 124 | 2.88 | | 8 | 0.95 | 2.75 | | 996.7 | 3.56 |
| | D | 100 | 12866 | 0.102 | | 1011 | 0.00 | 0.102 | | 1024.0 | 0.516 |
| 3 | E | 78.9 | 11331 | 0.102 | | 823 | 0.00 | 0.102 | | 2.43 | 0.498 |
| | F | 21.1 | 3030 | 1014.8 | | 21 | * * | 2.43 | | 1024.0 | 95.3 |
| | G | 100 | 14358 | 0.102 | | 823 | 0.00 | 0.102 | | 1024.0 | 20.5 |

FIG.11D

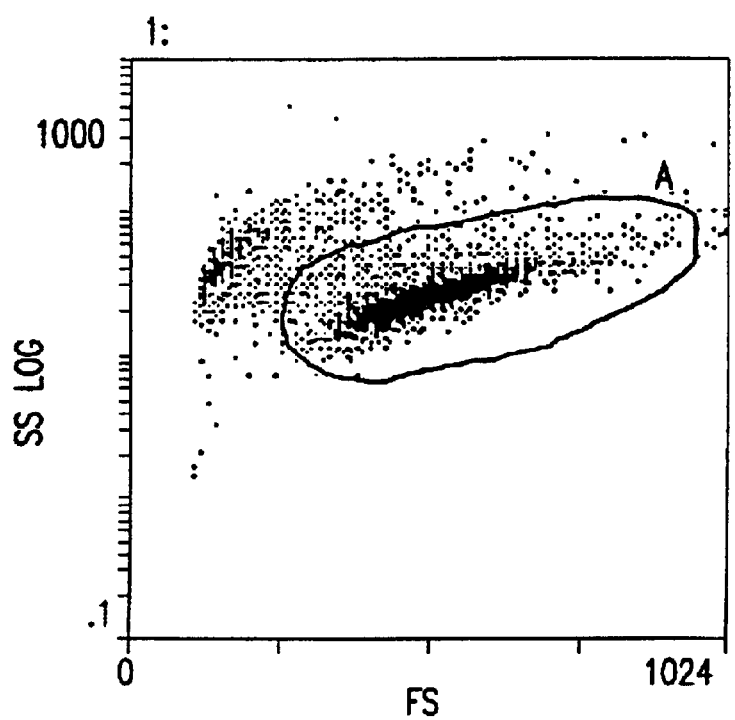
FIG.13A1
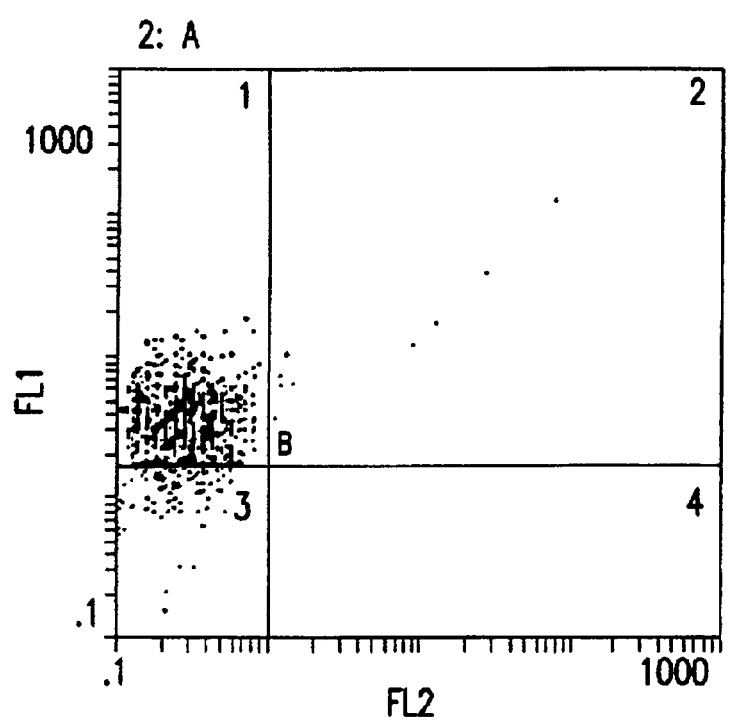
FIG.13A2

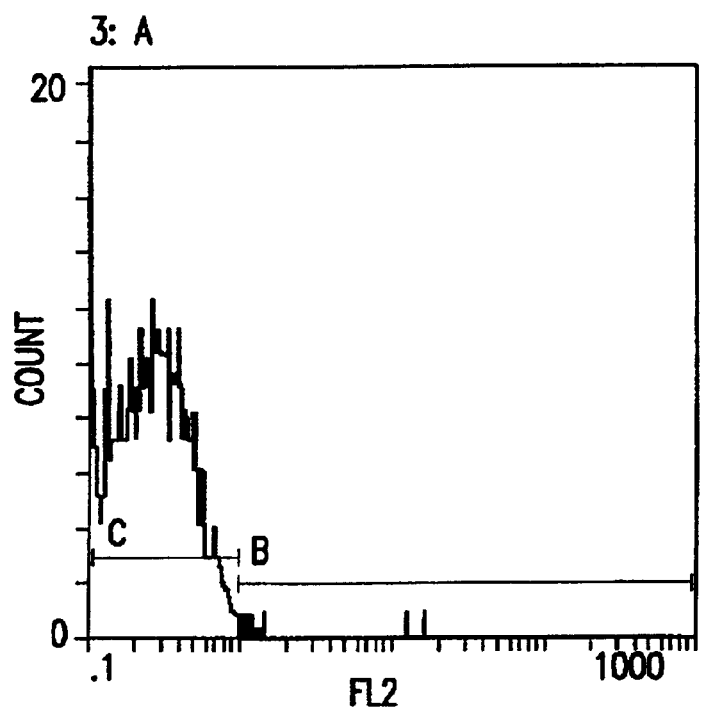
FIG.13A3
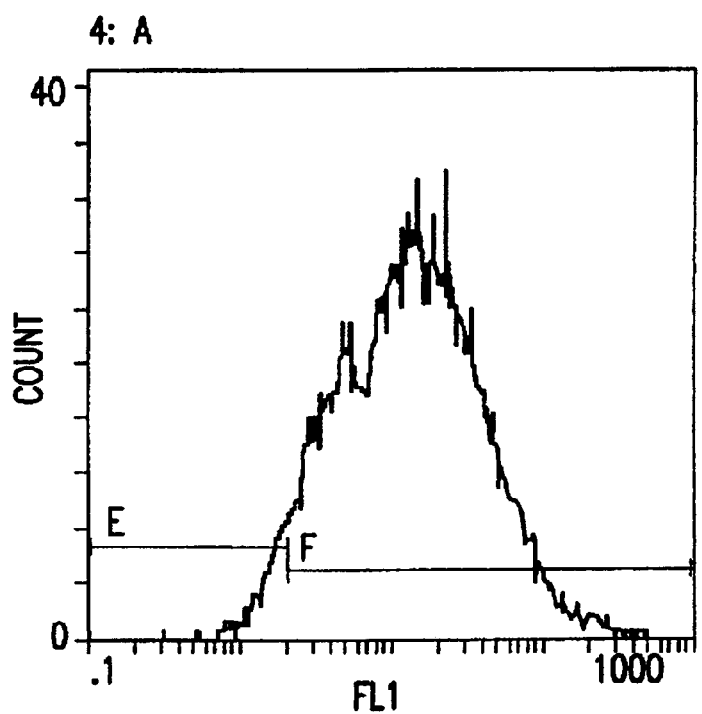
FIG.13A4

STATS: NORMALIZED,    LISTGATING: DISABLED

| HIST | REGION ID | % | COUNT | PkPosX | PkPosY | PkCnt | FPCVX | FPCVY | MnI X | MnIY |
|---|---|---|---|---|---|---|---|---|---|---|
| 1 | A A | 76.8 | 10000 | 464.0 | 21.0 | 56 | 23.20 | 38.40 | 500.9 | 27.7 |
| 2 | B1 B | 96.8 | 9677 | 0.102 | 14.7 | 289 | 40.65 | 108.00 | 0.139 | 24.1 |
|   | B2 B | 0.35 | 35 | 1.47 | 5.76 | 2 | 139.91 | 89.48 | 9.59 | 14.6 |
|   | B3 B | 2.87 | 287 | 0.102 | 1.37 | 11 | 55.47 | 50.95 | 0.273 | 1.23 |
|   | B4 B | 0.01 | 1 | 1.10 | 1.58 | 1 | 0.00 | 0.00 | 1.14 | 1.63 |

| HIST | REGION ID | % | COUNT | PkPosX | PkPosY | PkCnt | HPCV | Min | Max | Mn |
|---|---|---|---|---|---|---|---|---|---|---|
| 3 | C C | 16.7 | 1667 | 0.116 |  | 20 | 0.53 | 0.110 | 1.04 | 0.325 |
|   | D D | 0.36 | 36 | 1.08 |  | 2 | 0.38 | 1.02 | 970.2 | 9.47 |
| 4 | E E | 5.09 | 509 | 1.84 |  | 13 | 3.59 | 0.110 | 2.10 | 1.53 |
|   | F F | 95.2 | 9519 | 15.5 |  | 47 | 10.86 | 2.07 | 979.0 | 24.3 |

FIG. 13A5

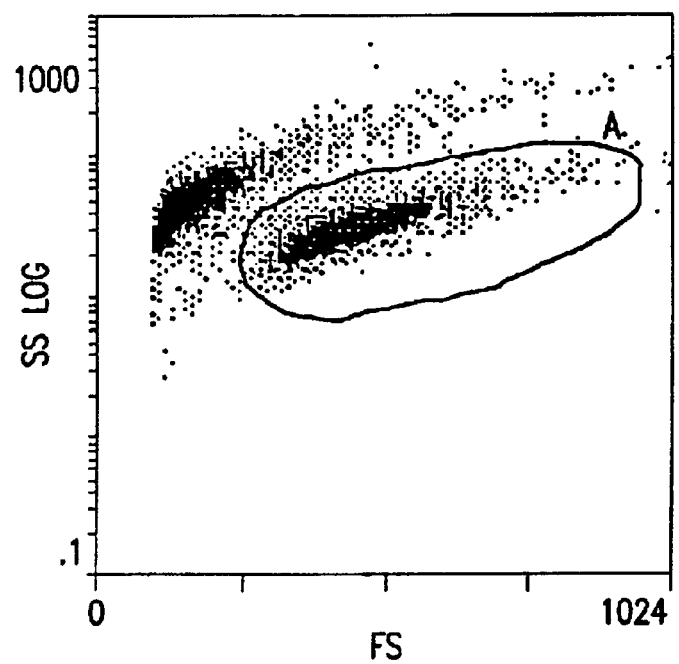
FIG.13B1
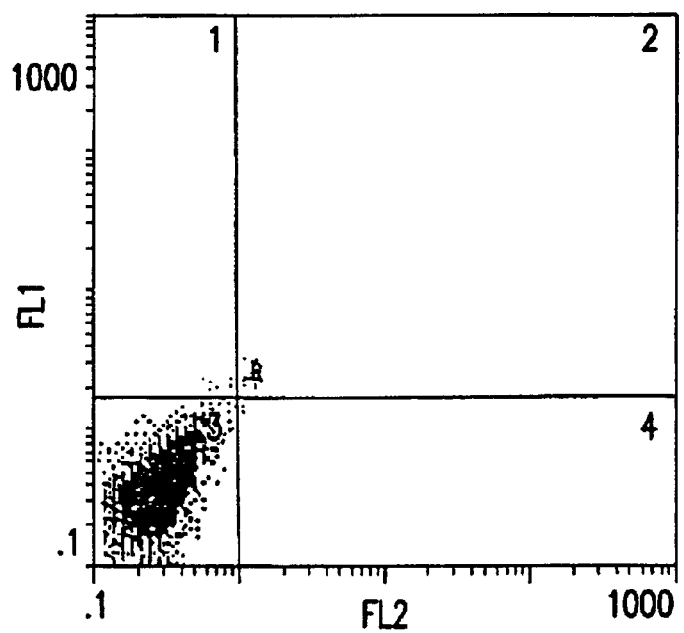
FIG.13B2

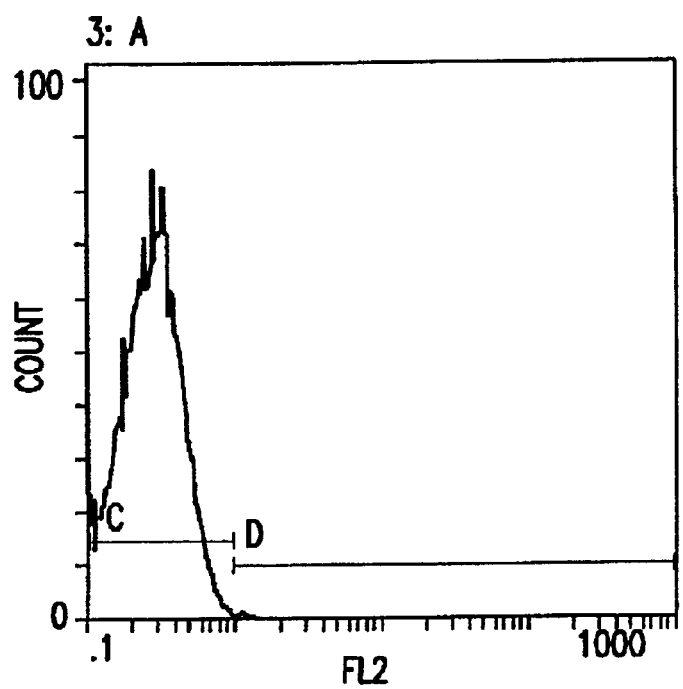
FIG.13B3
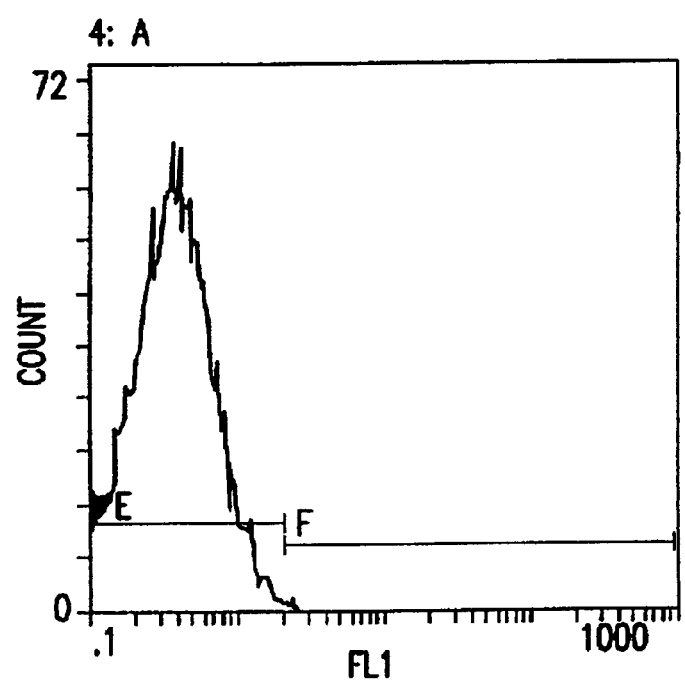
FIG.13B4

STATS: NORMALIZED, LISTGATING: DISABLED

| HIST | REGION ID | % | COUNT | PkPosX | PkPosY | PkCnt | FPCVX | FPCVY | MnlX | MnlY |
|---|---|---|---|---|---|---|---|---|---|---|
| 1 | A A | 45.5 | 10000 | 408.0 | 22.6 | 65 | 22.18 | 34.15 | 458.5 | 31.2 |
| 2 | B1 B | 0.37 | 37 | 0.665 | 1.82 | 3 | 39.12 | 29.87 | 0.764 | 2.19 |
|   | B2 B | 0.30 | 30 | 1.18 | 2.26 | 3 | 75.00 | 57.16 | 2.61 | 3.48 |
|   | B3 B | 99.2 | 9923 | 0.102 | 0.102 | 279 | 51.58 | 65.59 | 0.285 | 0.398 |
|   | B4 B | 0.10 | 10 | 1.10 | 1.37 | 3 | 5.98 | 17.11 | 1.15 | 1.39 |

| HIST | REGION ID | % | COUNT | PkPosX | PkPosY | PkCnt | HPCV | Min | Max | Mn |
|---|---|---|---|---|---|---|---|---|---|---|
| 3 | C C | 88.6 | 8888 | 0.271 |  | 100 | 3.72 | 0.110 | 1.04 | 0.310 |
|   | D D | 0.40 | 40 | 1.14 |  | 4 | 0.76 | 1.02 | 970.2 | 2.22 |
| 4 | E E | 90.4 | 9043 | 0.398 |  | 70 | 20.55 | 0.110 | 2.10 | 0.435 |
|   | F F | 0.30 | 30 | 2.14 |  | 2 | 0.57 | 2.07 | 979.0 | 3.91 |

FIG.13B5

STATS: NORMALIZED, LISTGATING: DISABLED

| HIST | REGION ID | | % | COUNT | PkPosX | PkPosY | PkCnt | FPCVX | FPCVY | MnI X | MnI Y |
|---|---|---|---|---|---|---|---|---|---|---|---|
| 1 | A | A | 84.0 | 8572 | 264.0 | 14.7 | 48 | 40.53 | 49.42 | 397.2 | 29.9 |
| 2 | B1 | B FITC | 13.8 | 1179 | 0.102 | 34.8 | 36 | 137.10 | 82.75 | 0.690 | 33.2 |
|   | B2 | B DOUBLE LABELED | 26.2 | 2247 | 4.32 | 8.87 | 11 | 69.76 | 73.66 | 12.0 | 27.4 |
|   | B3 | B NOT LABELED | 54.0 | 4632 | 0.102 | 0.102 | 28 | 78.81 | 82.60 | 0.998 | 0.598 |
|   | B4 | B Rhod | 6.00 | 514 | 19.6 | 0.102 | 10 | 82.82 | 122.34 | 10.8 | 0.766 |

| HIST | REGION ID | % | COUNT | PkPosX | PkPosY | PkCnt | HPCV | Min | Max | Mn |
|---|---|---|---|---|---|---|---|---|---|---|
| 3 | C C | 62.4 | 5351 | 0.825 | | 41 | 0.82 | 0.106 | 3.88 | 1.22 |
|   | D D | 28.3 | 2425 | 7.68 | | 23 | 3.01 | 3.88 | 970.2 | 1.29 |
| 4 | E E | 60.9 | 5222 | 0.102 | | 826 | 0.00 | 0.102 | 4.32 | 0.658 |
|   | F F | 39.2 | 3361 | 18.7 | | 23 | 1.63 | 4.17 | 979.0 | 29.9 |

FIG.14E

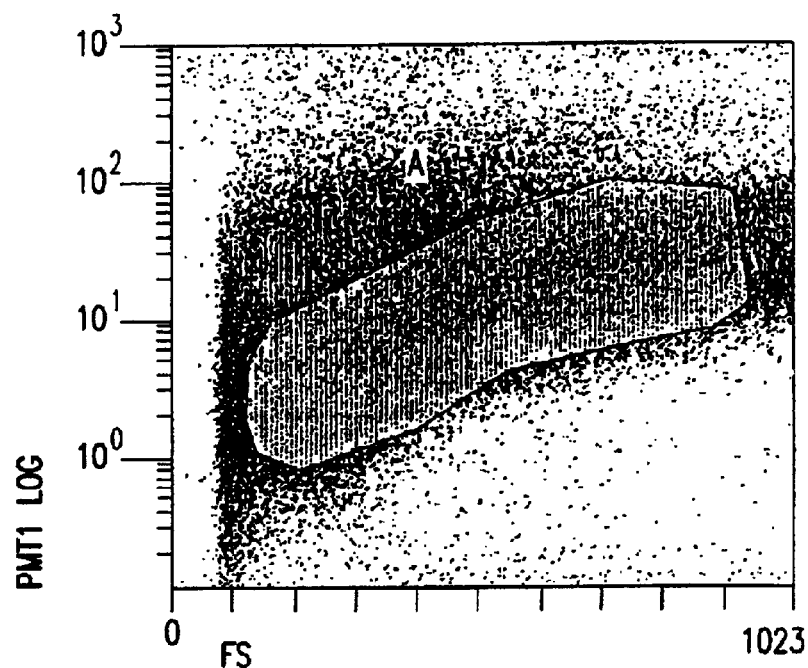
FIG.15A1
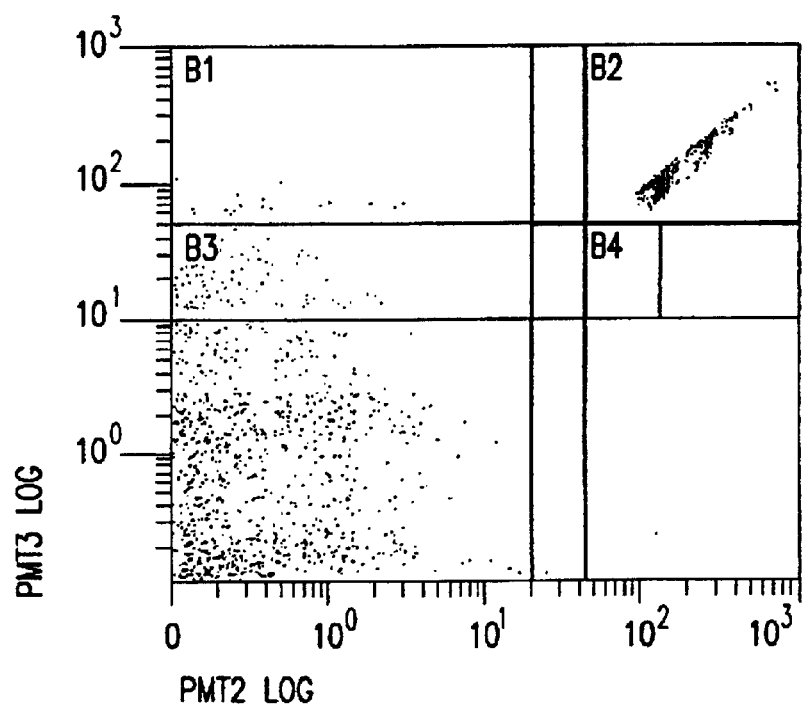
FIG.15A2

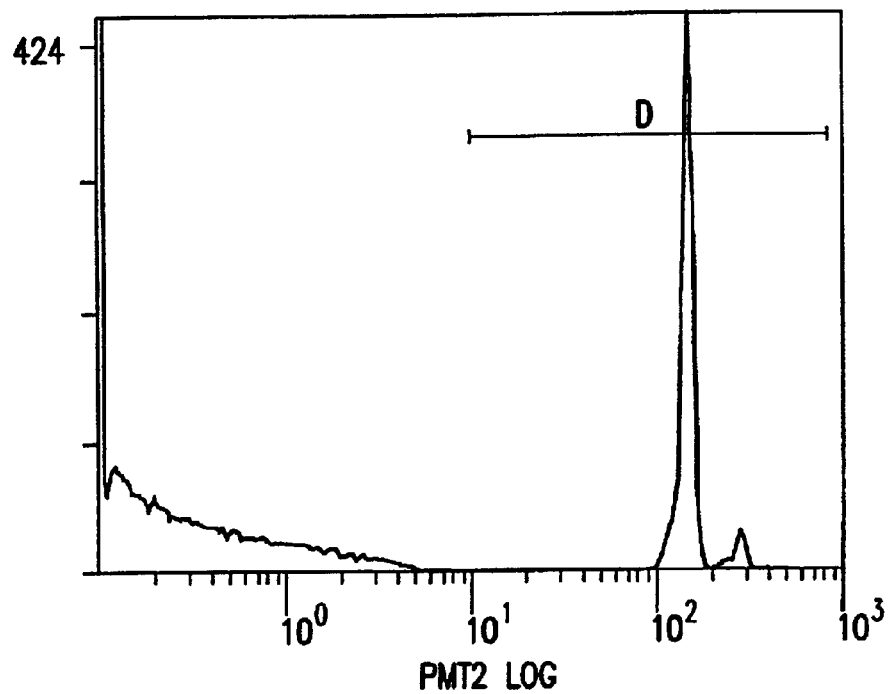
FIG.15A3
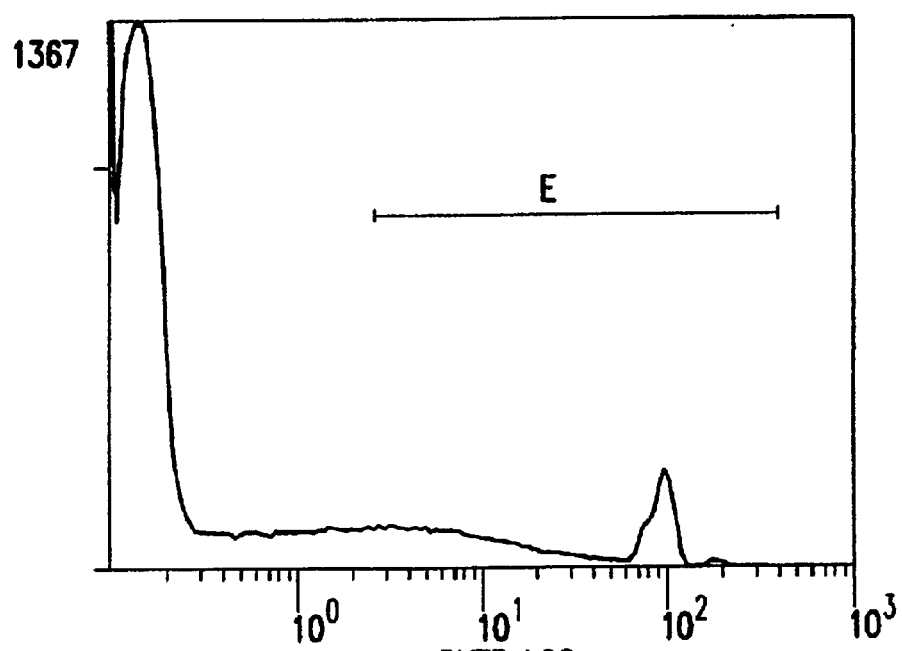
FIG.15A4

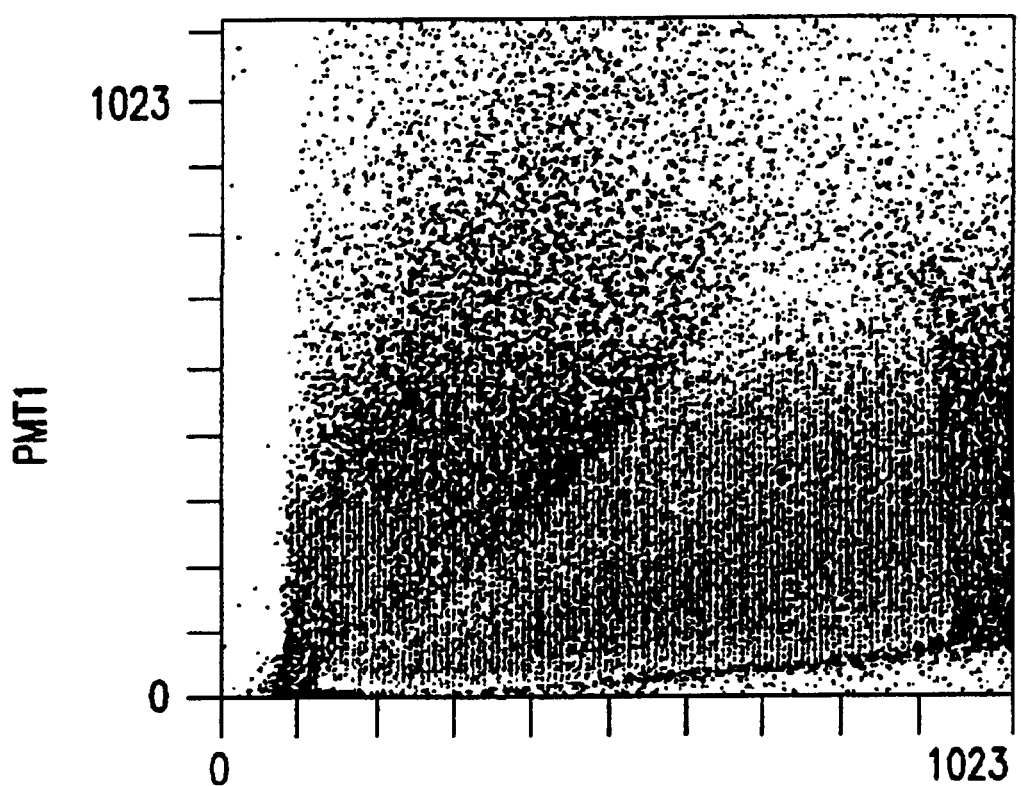
FIG.15A5

| GATE:- UNGATED | | | | |
|---|---|---|---|---|
| FILENAME:- 00001264 158.LMD | | | | |
| MEAN CALCULATION METHOD:-LOG-LOG | | | | |
| REGION | NUMBER | %TOTAL | %GATED | X-MEDIAN |
| A | 1475351 | 79.68 | 79.68 | 371.0 |
| B1 | 1983 | 0.11 | 0.11 | 0.1 |
| B2 | 9512 | 0.51 | 0.51 | 144.1 |
| B3 | 1839985 | 99.38 | 99.38 | 0.1 |
| B4 | 57 | 0.00 | 0.00 | 70.8 |
| C | 9565 | 0.52 | 0.52 | 144.1 |
| D | 9764 | 0.53 | 0.53 | 144.1 |
| E | 34097 | 1.84 | 1.84 | 14.2 |

FIG.15A6

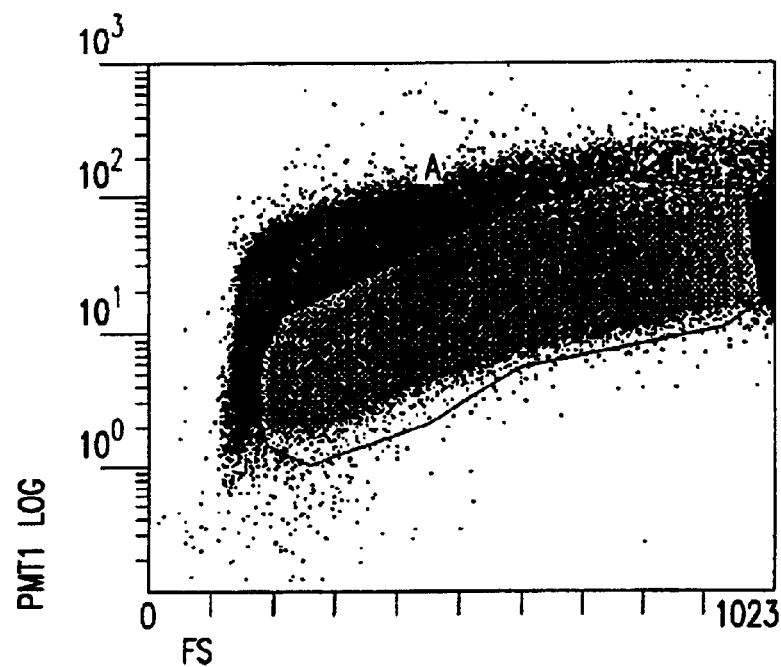
FIG.15B1
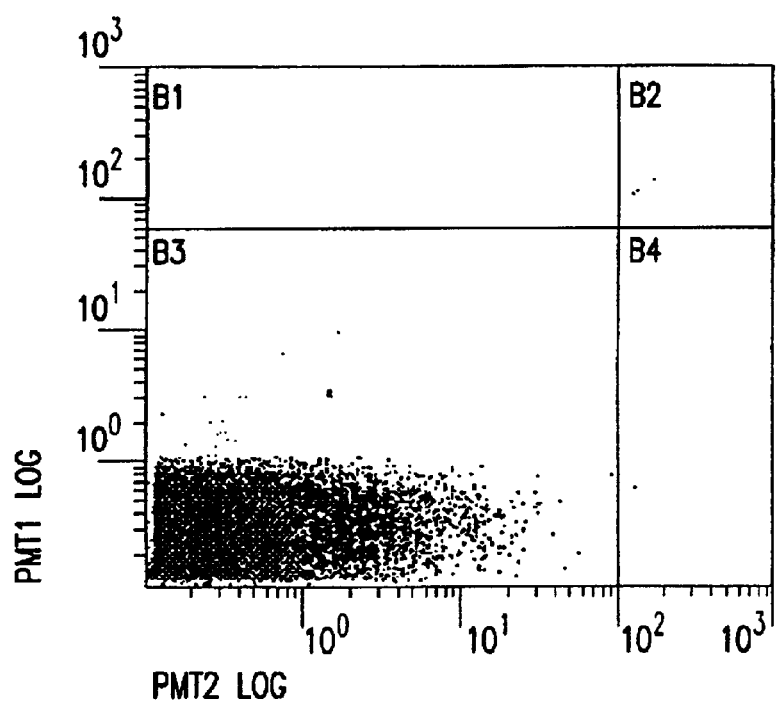
FIG.15B2

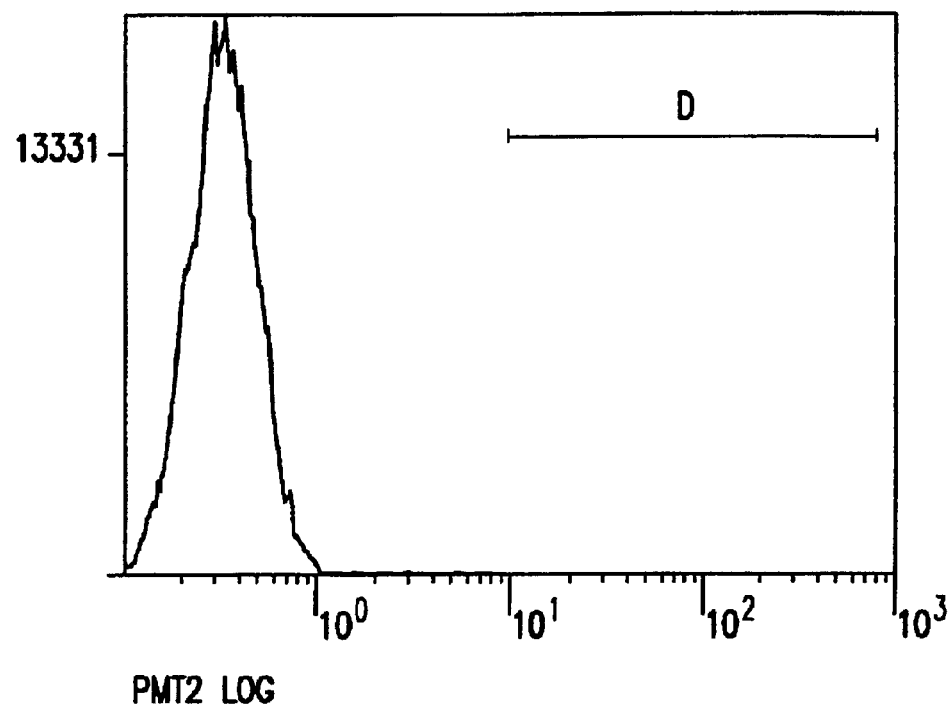
FIG.15B3
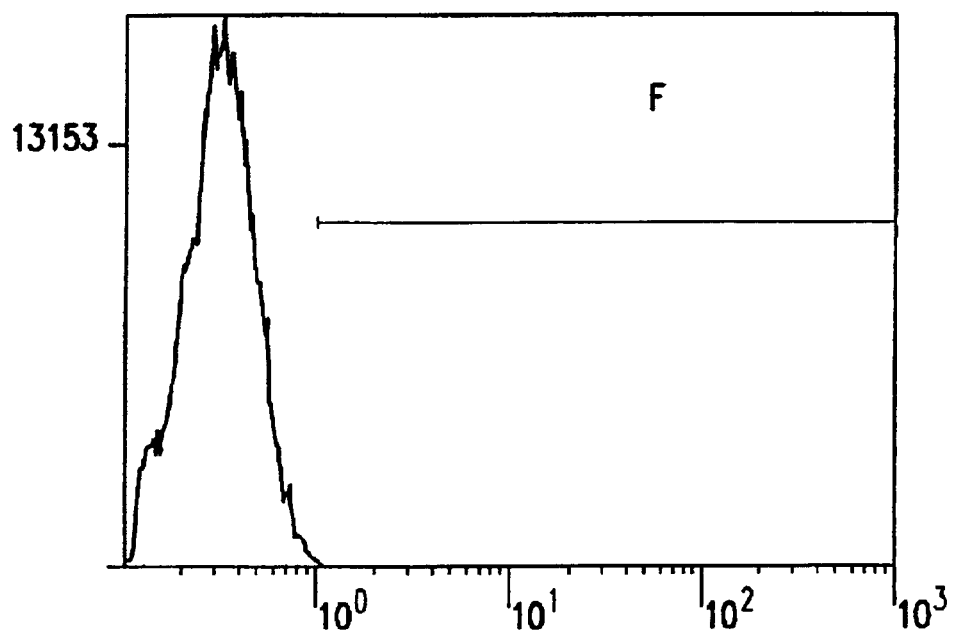
FIG.15B4

| GATE:- UNGATED | | | | |
|---|---|---|---|---|
| FILENAME:- 00001721 566.LMD | | | | |
| MEAN CALCULATION METHOD:-LOG-LOG | | | | |
| REGION | NUMBER | %TOTAL | %GATED | X-MEDIAN |
| A | 1172798 | 83.13 | 83.13 | 414.0 |
| B1 | 1 | 0.00 | 0.00 | 0.7 |
| B2 | 15 | 0.00 | 0.00 | 159.1 |
| B3 | 1410858 | 100.00 | 100.00 | 0.3 |
| B4 | 6 | 0.00 | 0.00 | 172.5 |
| C | 21 | 0.00 | 0.00 | 164.9 |
| D | 254 | 0.02 | 0.02 | 13.4 |
| F | 609 | 0.04 | 0.04 | 1.0 |

FIG.15B5

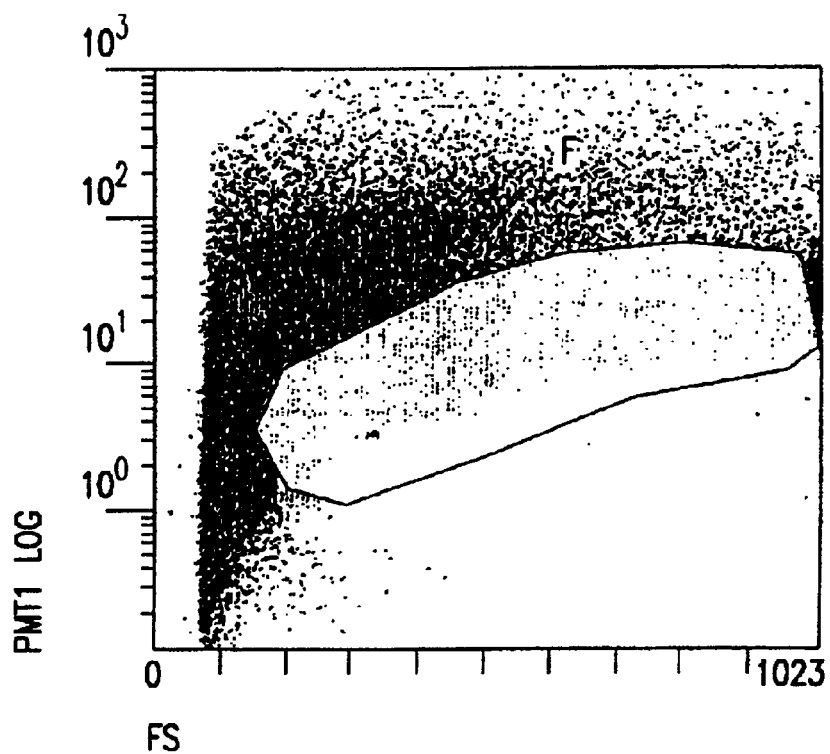
FIG.16A1
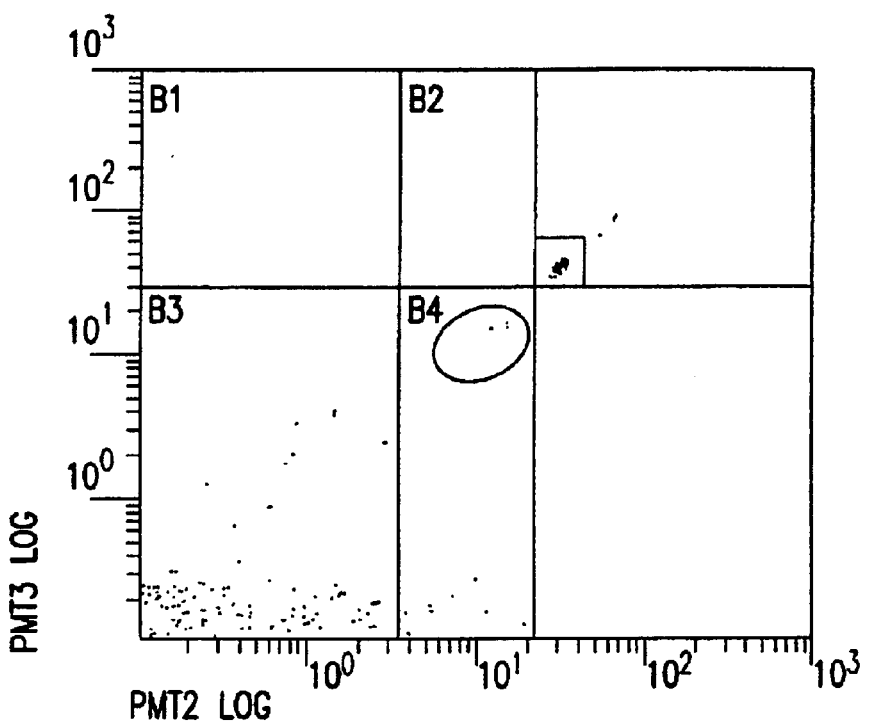
FIG.16A2

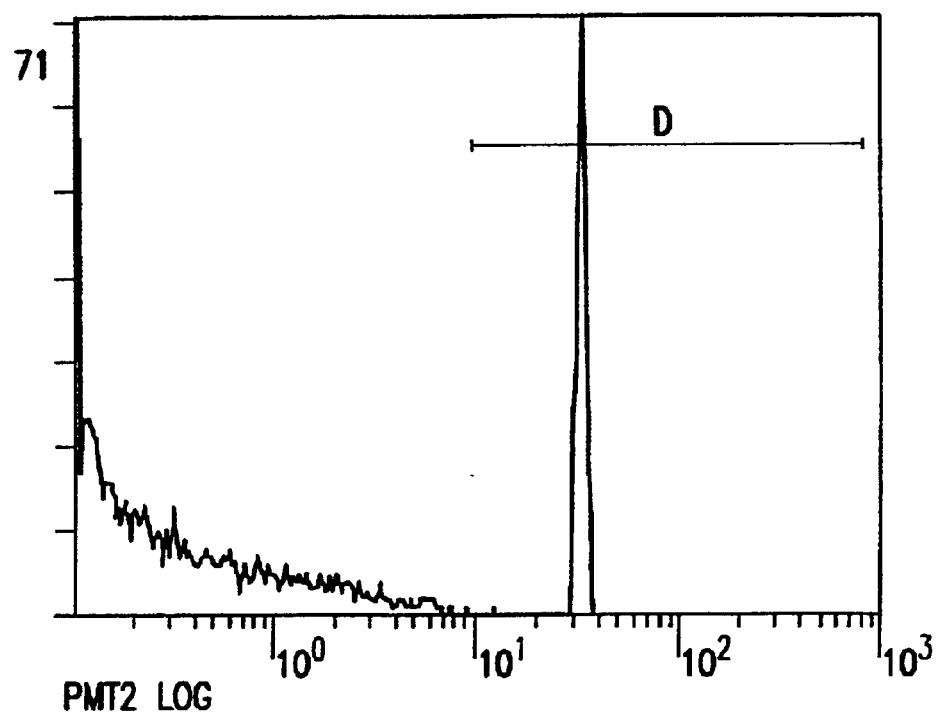
FIG.16A3
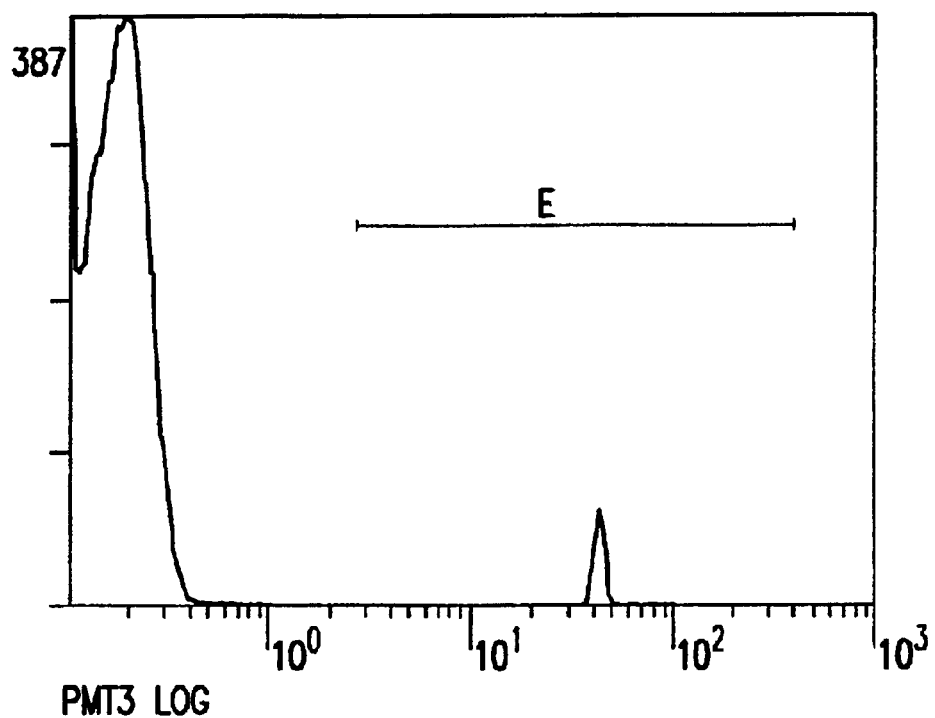
FIG.16A4

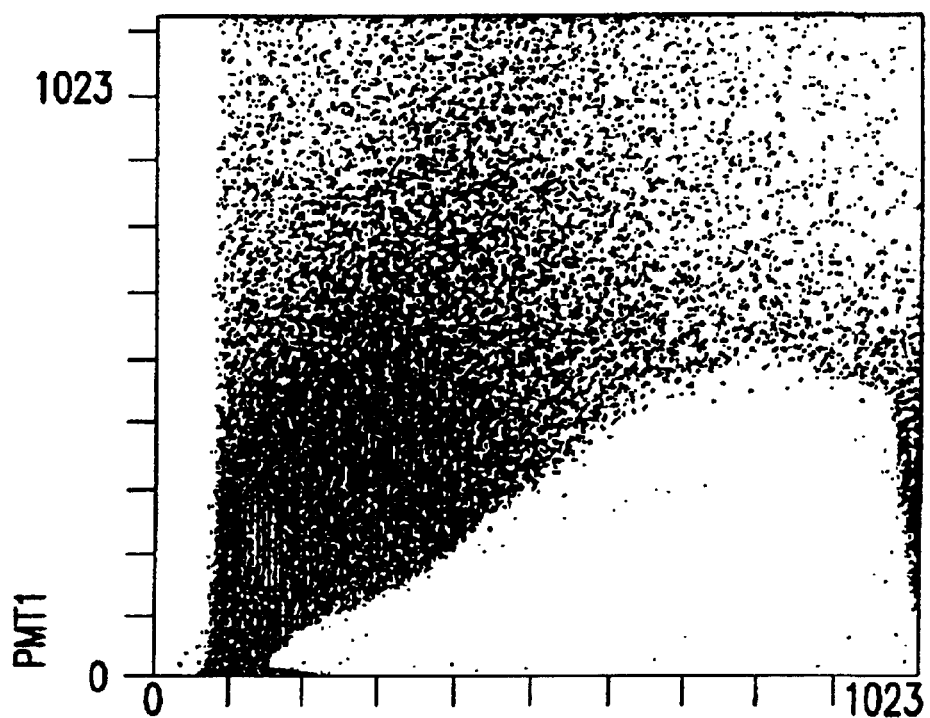
FIG.16A5

| GATE:- UNGATED | | | | |
|---|---|---|---|---|
| FILENAME:- 00001224 118.LMD | | | | |
| MEAN CALCULATION METHOD:-LOG-LOG | | | | |
| REGION | NUMBER | %TOTAL | %GATED | X-MEDIAN |
| B1 | 203 | 0.02 | 0.02 | 0.1 |
| B2 | 1029 | 0.10 | 0.10 | 32.7 |
| B3 | 979209 | 99.84 | 99.84 | 0.1 |
| B4 | 326 | 0.03 | 0.03 | 5.5 |
| C | 1342 | 0.14 | 0.14 | 32.1 |
| D | 1082 | 0.11 | 0.11 | 32.7 |
| E | 1489 | 0.15 | 0.15 | 41.7 |
| F | 574114 | 58.54 | 58.54 | 383.0 |

FIG.16A6

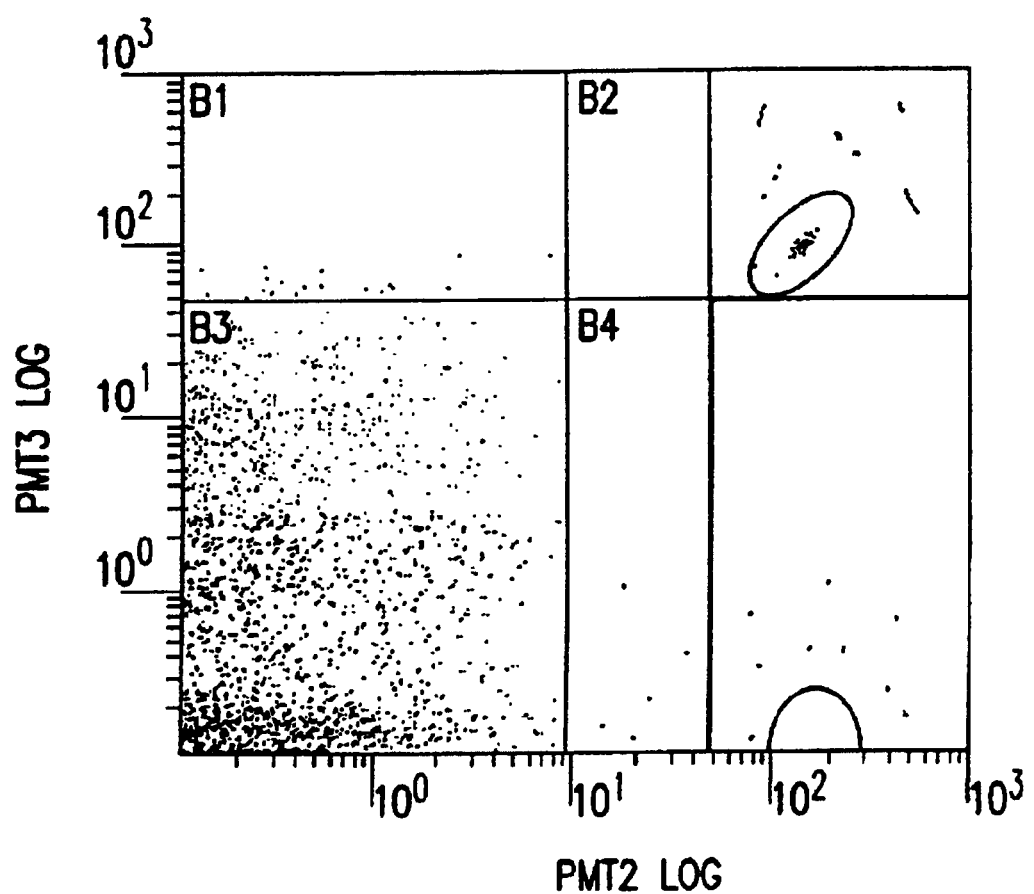
FIG.16B1

| GATE:- UNGATED | | | | |
| --- | --- | --- | --- | --- |
| FILENAME:- FHhetero_7-21_olaf.LMD | | | | |
| MEAN CALCULATION METHOD:-LOG-LOG | | | | |
| REGION | NUMBER | %TOTAL | %GATED | X-MEDIAN |
| A | 3078481 | 87.70 | 87.70 | 371.0 |
| B1 | 1182 | 0.03 | 0.03 | 0.1 |
| B2 | 335 | 0.01 | 0.01 | 144.1 |
| B3 | 3508248 | 99.95 | 99.95 | 0.1 |
| B4 | 282 | 0.01 | 0.01 | 16.5 |
| C | 368 | 0.01 | 0.01 | 144.1 |
| D | 587 | 0.02 | 0.02 | 134.1 |
| E | 19444 | 0.55 | 0.55 | 7.4 |

FIG.16B2

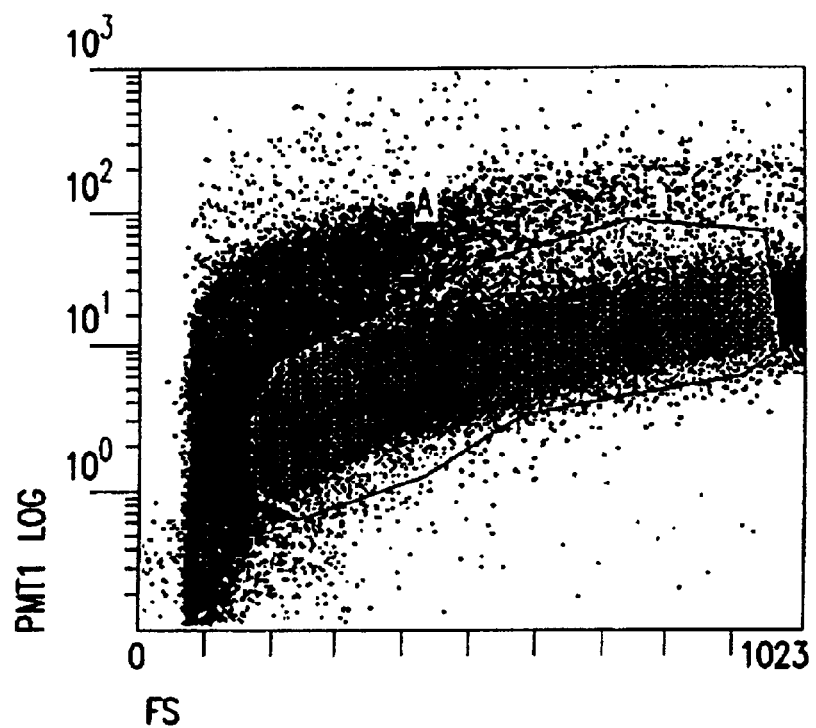
FIG.17A1
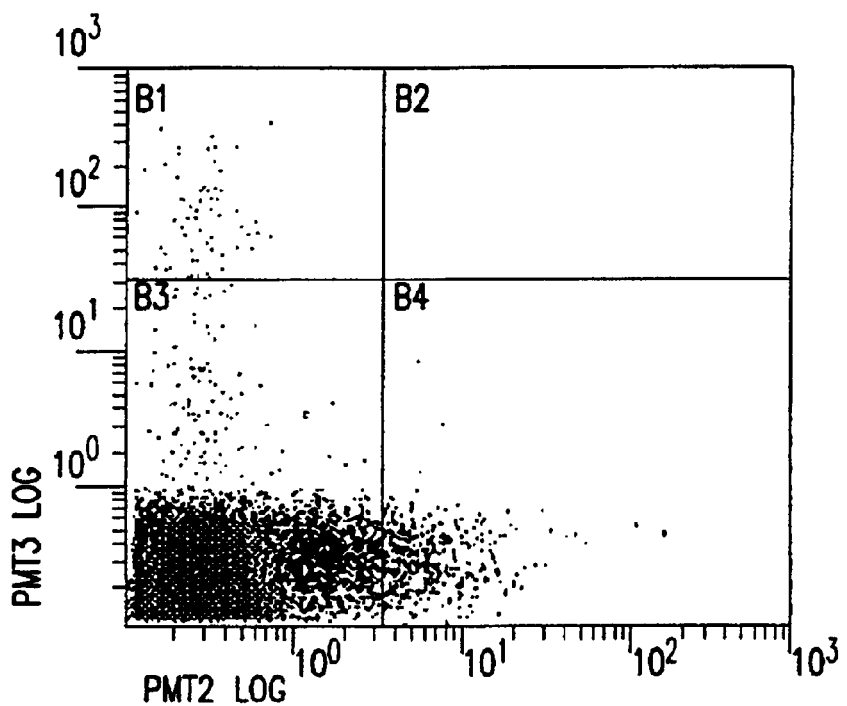
FIG.17A2

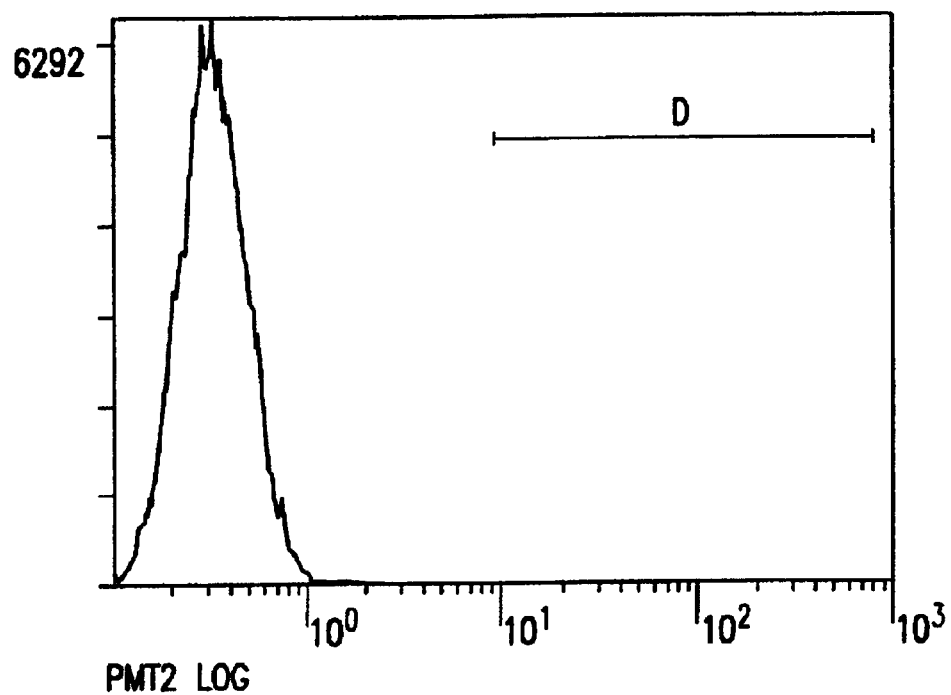
FIG.17A3
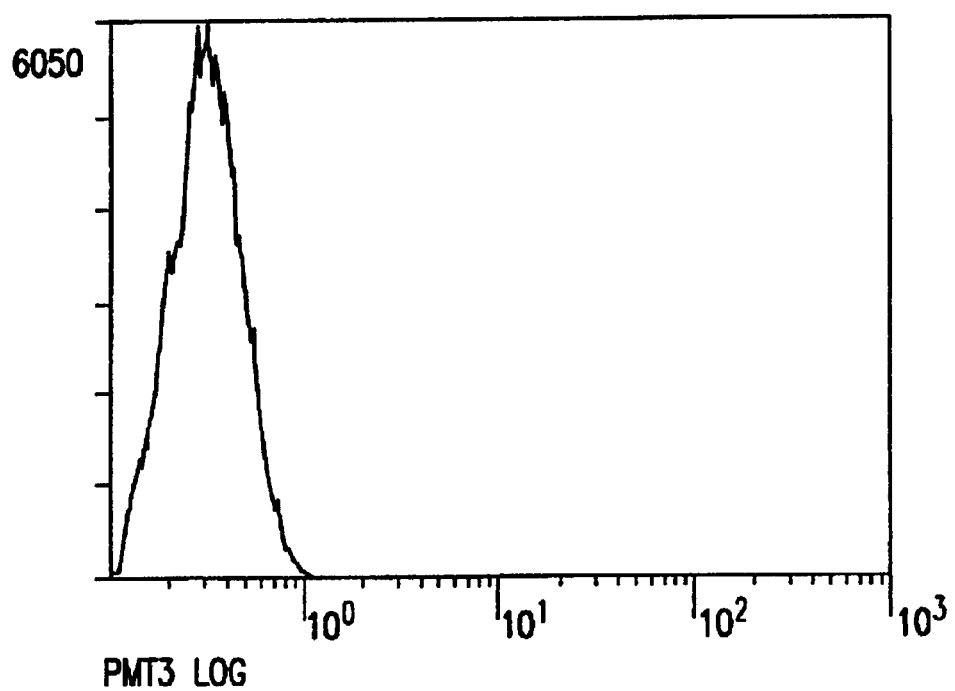
FIG.17A4

| GATE:- UNGATED | | | | |
|---|---|---|---|---|
| FILENAME:- Olaf_cntrol_8-11-00.LMD | | | | |
| MEAN CALCULATION METHOD:- LOG-LOG | | | | |
| REGION | NUMBER | %TOTAL | %GATED | X-MEDIAN |
| A | 502458 | 76.28 | 76.28 | 373.0 |
| B1 | 99 | 0.02 | 0.02 | 0.3 |
| B2 | 1 | 0.00 | 0.00 | 3.7 |
| B3 | 658574 | 99.98 | 99.81 | 0.3 |
| B4 | 1095 | 0.17 | 0.17 | 5.2 |
| D | 174 | 0.03 | 0.03 | 13.7 |

FIG. 17A5

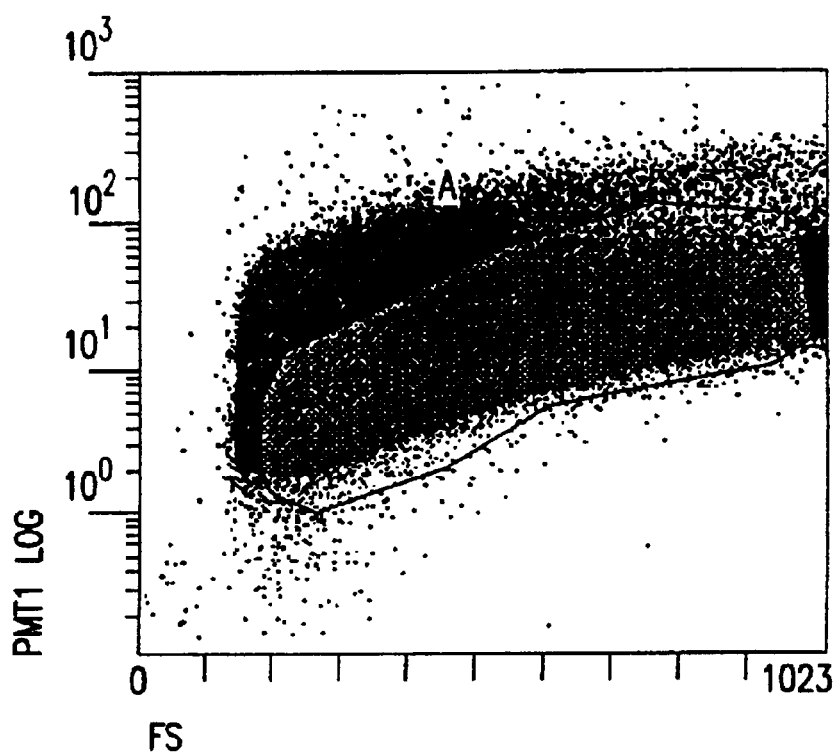
FIG.17B1
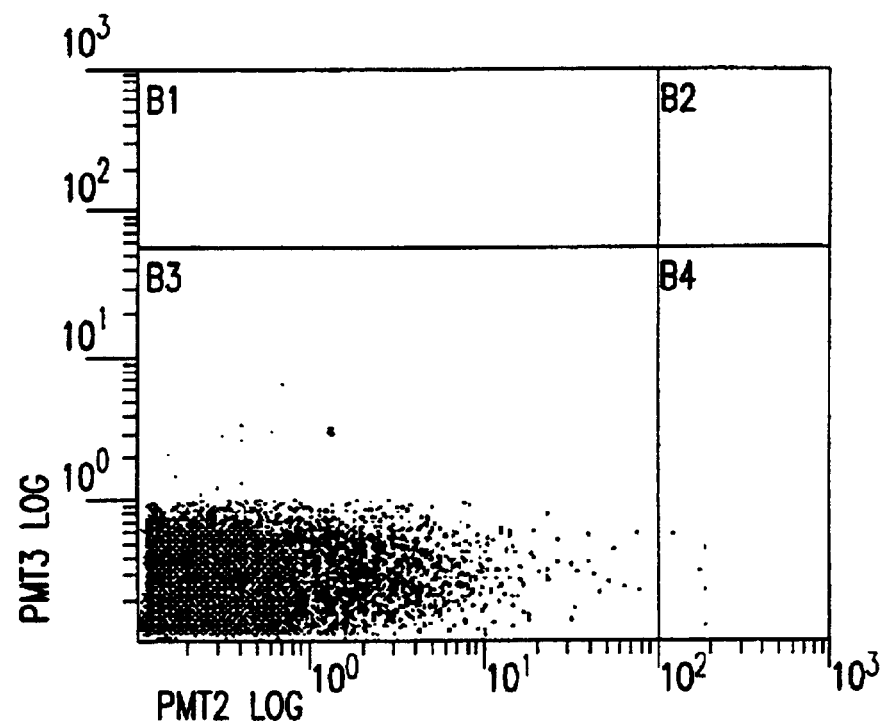
FIG.17B2

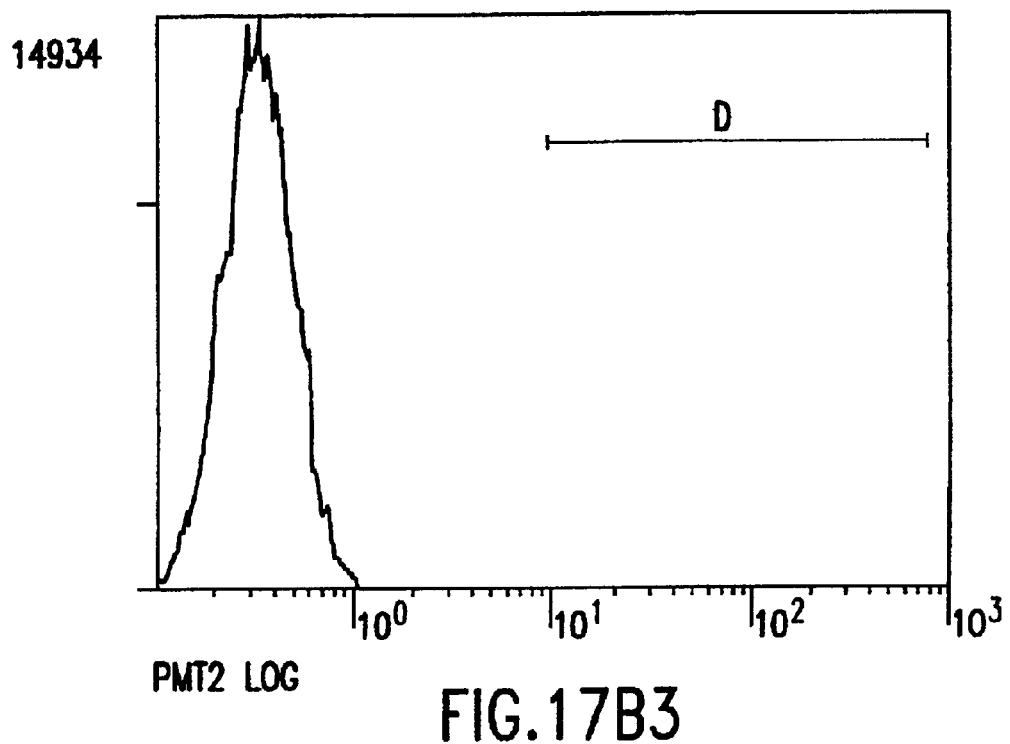
FIG.17B3
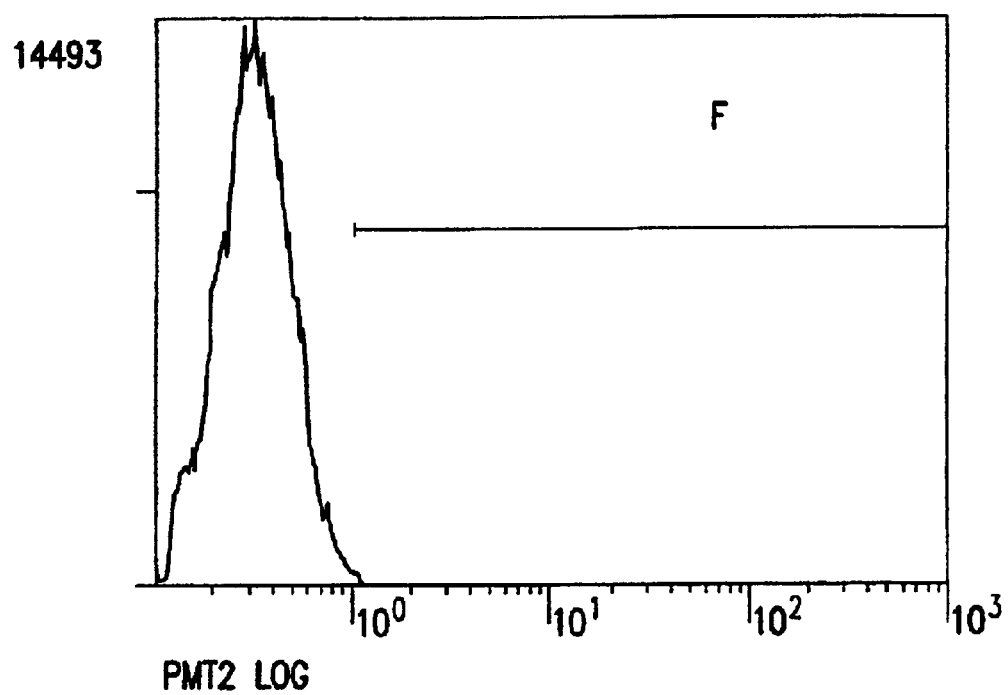
FIG.17B4

| GATE:- UNGATED | | | | |
|---|---|---|---|---|
| FILENAME:- 00001722 567.LMD | | | | |
| MEAN CALCULATION METHOD:-LOG-LOG | | | | |
| REGION | NUMBER | %TOTAL | %GATED | X-MEDIAN |
| A | 1304963 | 83.83 | 83.83 | 398.0 |
| B1 | 4 | 0.00 | 0.00 | 0.3 |
| B2 | 2 | 0.00 | 0.00 | 162.0 |
| B3 | 1556736 | 100.00 | 100.00 | 0.3 |
| B4 | 11 → 50 | 0.00 | 0.00 | 182.1 |
| C | 13 | 0.00 | 0.00 | 180.5 |
| D | 179 | 0.01 | 0.01 | 15.2 |
| F | 664 | 0.04 | 0.04 | 1.0 |

FIG.17B5

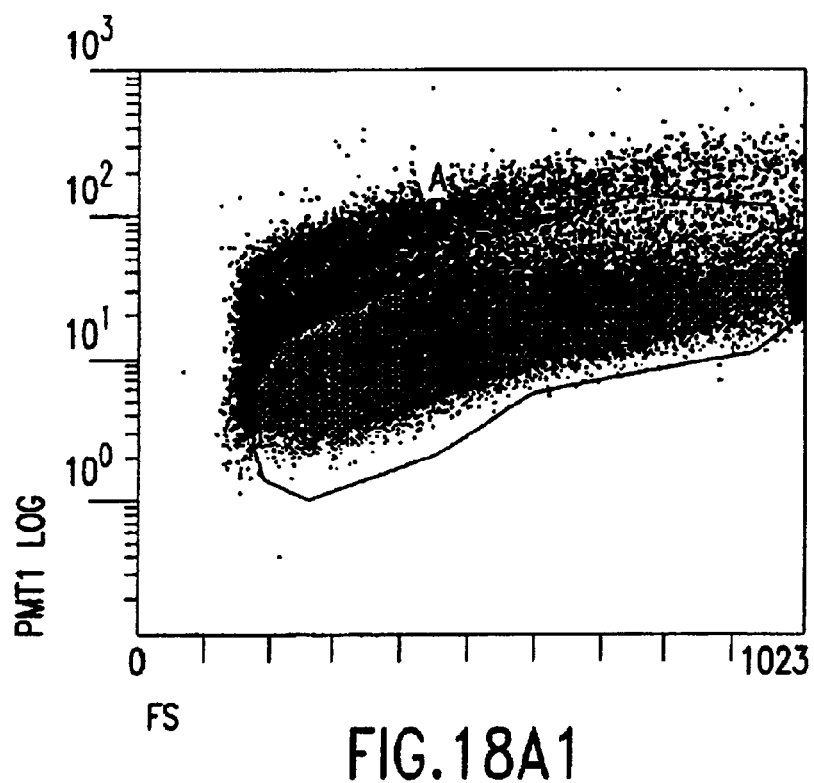
FIG.18A1
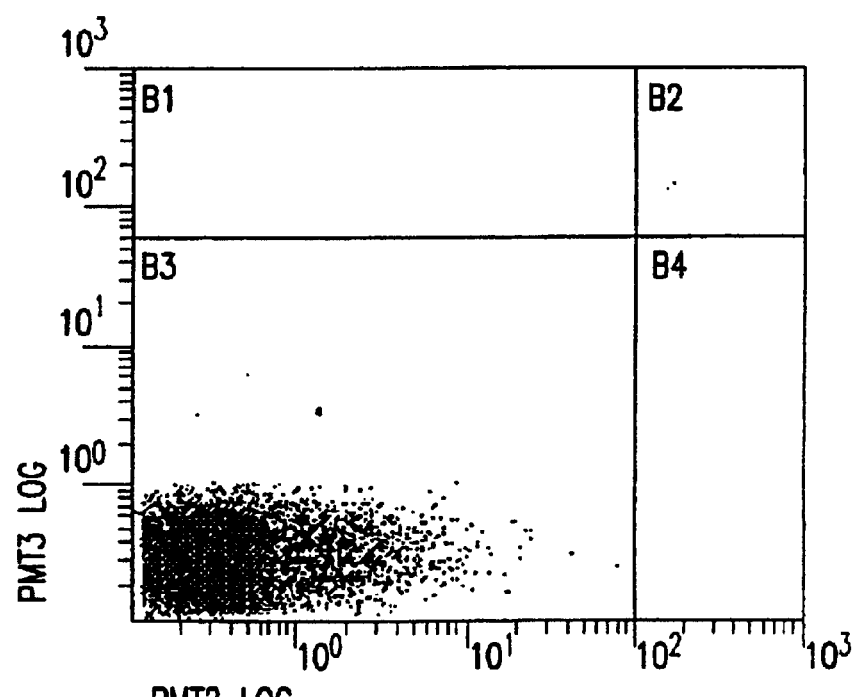
FIG.18A2

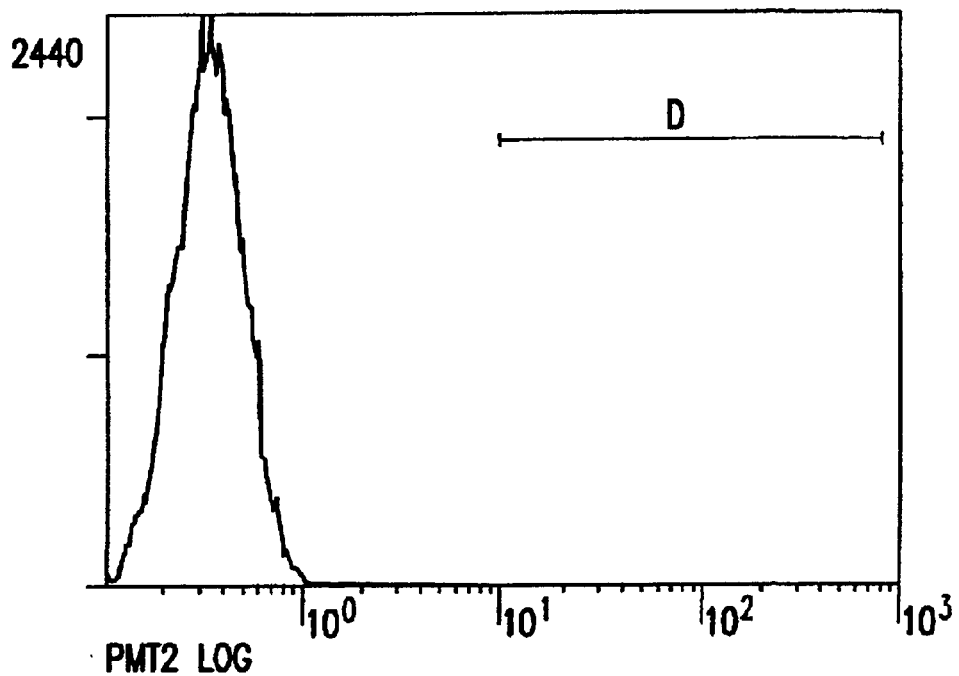
FIG.18A3
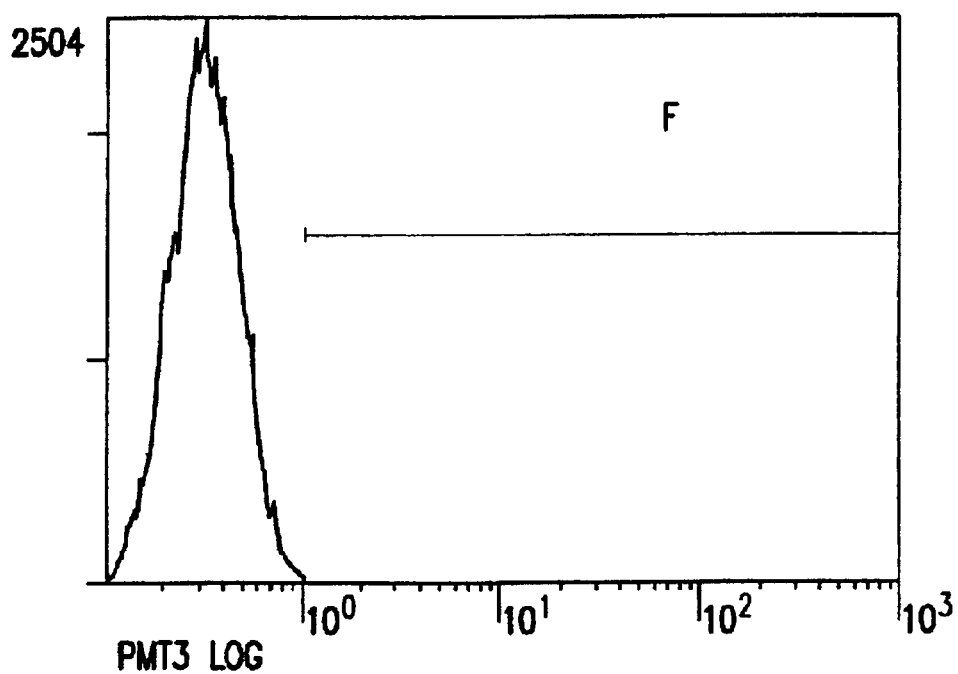
FIG.18A4

| GATE:- UNGATED | | | | |
|---|---|---|---|---|
| FILENAME:- 00001720 565.LMD | | | | |
| MEAN CALCULATION METHOD:- LOG-LOG | | | | |
| REGION | NUMBER | %TOTAL | %GATED | X-MEDIAN |
| A | 189157 | 72.32 | 72.32 | 437.0 |
| B1 | 0 | 0.00 | 0.00 | 0.1 |
| B2 | 10 | 0.00 | 0.00 | 166.4 |
| B3 | 261563 | 100.00 | 100.00 | 0.3 |
| B4 | 0 | 0.00 | 0.00 | 0.1 |
| C | 10 | 0.00 | 0.00 | 166.4 |
| D | 52 | 0.02 | 0.02 | 15.3 |
| F | 121 | 0.05 | 0.05 | 1.0 |

FIG.18A5

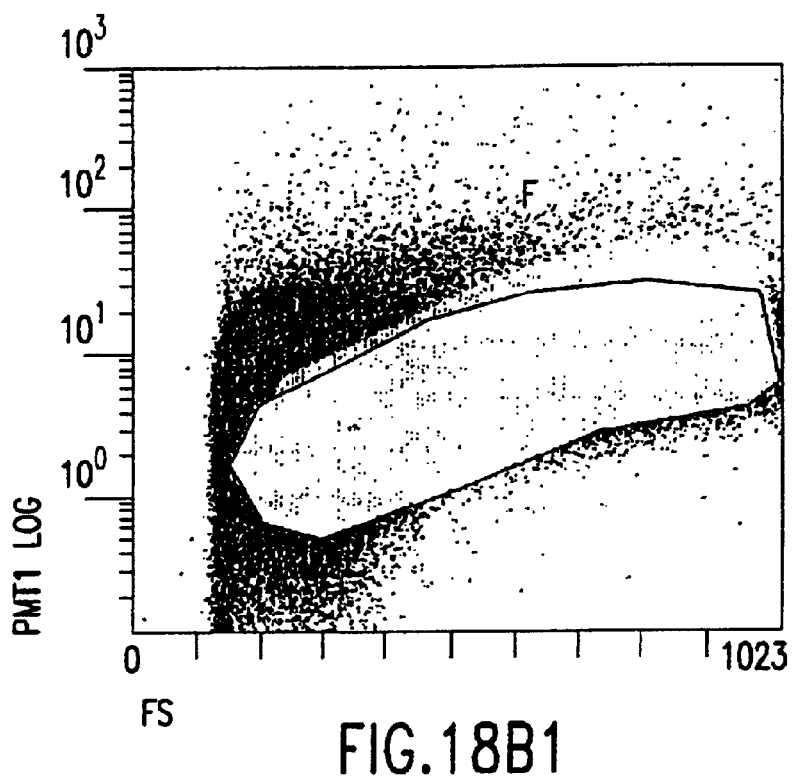
FIG.18B1
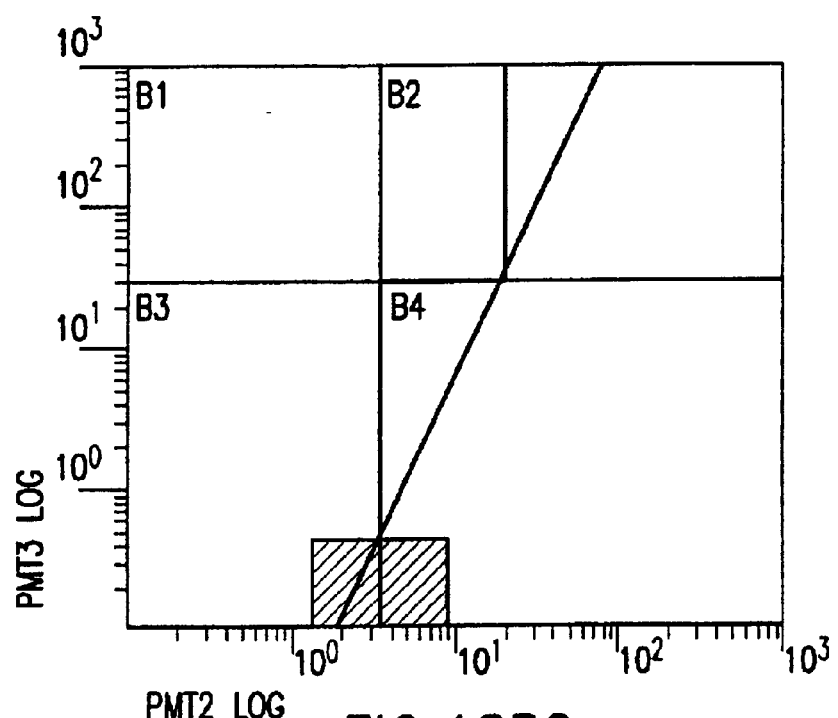
FIG.18B2

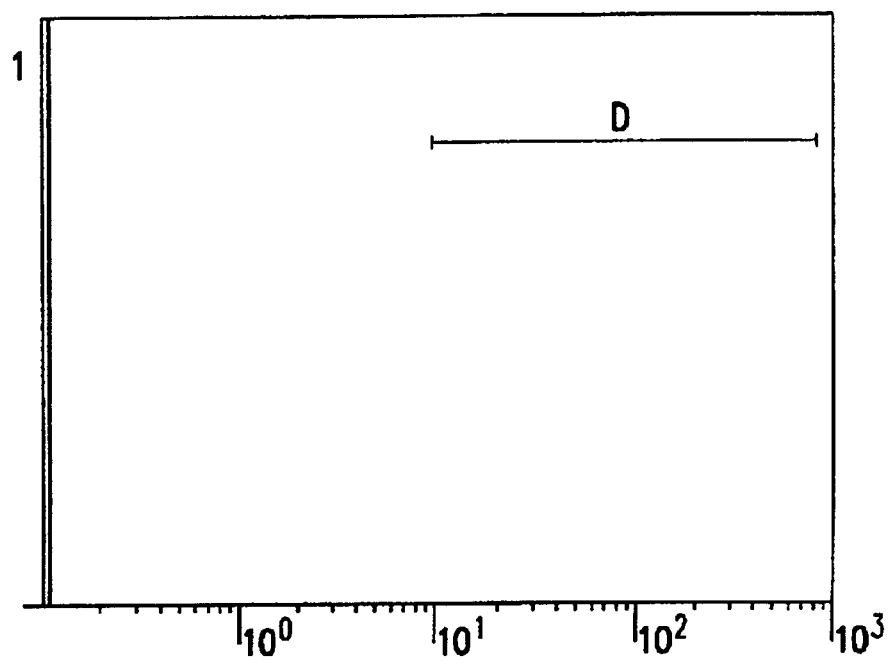
FIG.18B3
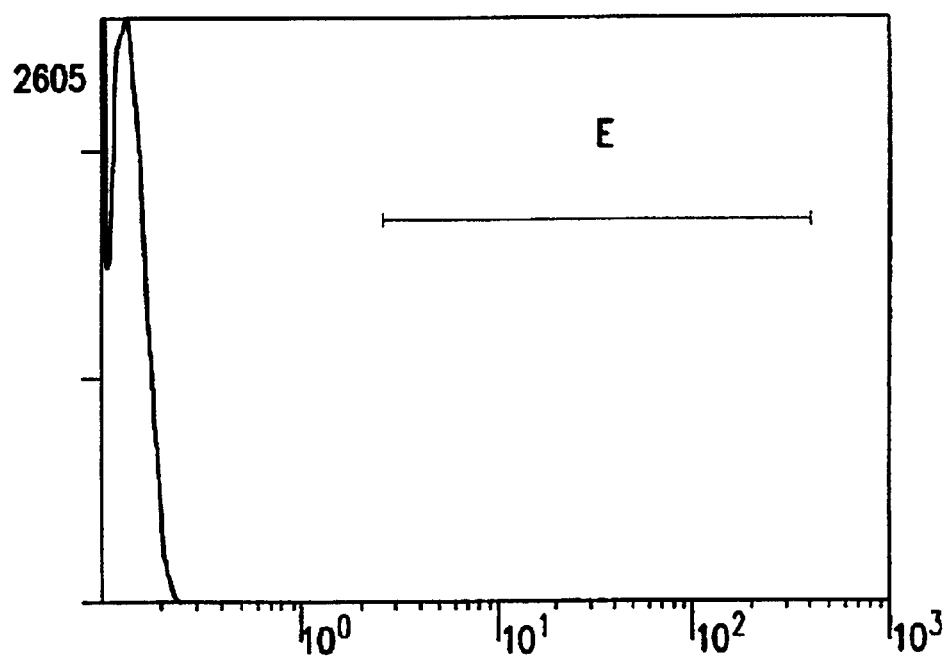
FIG.18B4

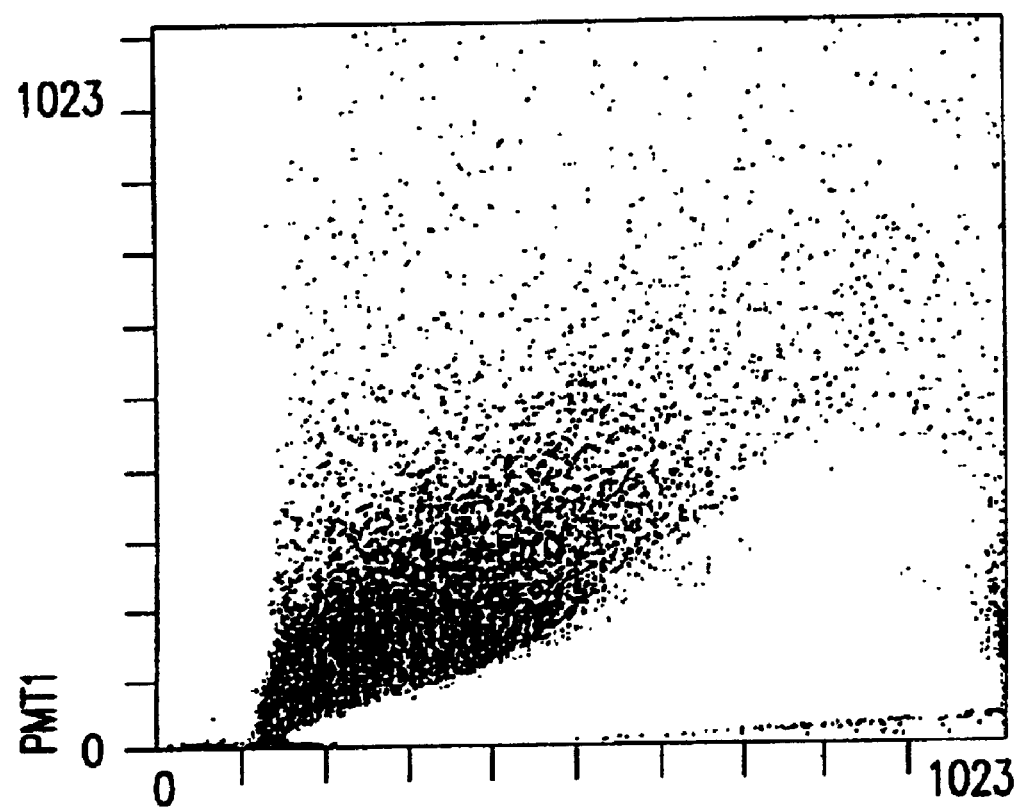
FIG.18B5

| GATE:- UNGATED | | | | |
|---|---|---|---|---|
| FILENAME:- 00001225 119.LMD | | | | |
| MEAN CALCULATION METHOD:- LOG-LOG | | | | |
| REGION | NUMBER | %TOTAL | %GATED | X-MEDIAN |
| B1 | 2 | 0.00 | 0.00 | 0.3 |
| B2 | 0 | 0.00 | 0.00 | 0.1 |
| B3 | 1386992 | 100.00 | 100.00 | 0.1 |
| B4 | 6 | 0.00 | 0.00 | 4.2 |
| C | 6 | 0.00 | 0.00 | 4.2 |
| D | 0 | 0.00 | 0.00 | 0.1 |
| E | 230 | 0.02 | 0.02 | 4.9 |
| F | 1072122 | 77.30 | 77.30 | 429.0 |

FIG.18B6

METHOD OF DETECTION AND INTERPRETATION OF MUTATIONS THROUGH EXPRESSION OR FUNCTION TESTS OF HAPLOID GENES

This application claims priority to U.S. provisional application No. 60/237,471 filed Oct. 2, 2000.

SPECIFICATION

This invention was made with government support under National Institutes of Health Grant No. R01 H37283 and U.S. Army Medical Research and Material Command under contract No. DAMD 17-98-1-8482. Consequently, the United States Government may have certain rights herein.

FIELD OF THE INVENTION

The present invention relates to a method for detection and interpretation of disease related mutations through the combination of haploid gene transfer with functional, immunological or other analysis of the gene product.

BACKGROUND OF INVENTION

Detection of disease-causing mutations is a complex and challenging task in medical and veterinary genetics and research. Unfortunately, loss-of-function mutations, including partial loss-of-function mutation, or gain-of-function mutations, including alteration of function and dominant negative mutations, causing inherited genetic diseases are a common problem for humans and other animals. Complete and effective detection of these mutations presents enormous possibilities as a diagnostic, preventative, or research tool.

Currently genomic sequencing of peripheral blood DNA is widely used for identification of genetic mutations associated with various diseases. In particular, it may be used to detect mutations in individuals for inherited genetic diseases. For example, Myriad Genetics, Inc. (Salt Lake City, Utah) has developed a genetic test for detection of loss-of-function mutations in BRCA1 and BRCA2, genes which have been linked to breast cancer. This test sequences all coding exons of BRCA1 and BRCA2, making it labor-intensive and costly. In addition, it cannot detect deleted exons, inversions, mutations causing loss of transcriptional activity, etc. As a result, many mutations in these two genes cannot be meaningfully detected by genomic sequencing. Table 1 displays the types and frequencies of mutations found in the BRCA1 and BRCA2 genes. Furthermore, when diploid cells that are heterozygous for a loss-of-function or a gain-of-function mutation are tested, the wild type allele can often mask the mutant allele. As a result, this test may not be accurate in detecting single mutant alleles. The usefulness of this and other such tests to the medical and veterinary professions and research scientists is therefore limited by their diagnostic shortcomings and prohibitive costs.

TABLE 1

| Mutation Type | Frequency and Type of Mutations in the BRCA1 and BRCA2 Genes | |
|---|---|---|
| | BRCA1 Gene | BRCA2 Gene |
| Frameshift | 195 (42.5%) | 126 (53.5%) |
| Nonsense | 55 (12%) | 20 (7.8%) |
| Splice | 16 (3.5%) | 4 (1.6%) |
| Missense | 21 (4.6%) | 12 (4.7%) |

TABLE 1-continued

| Mutation Type | Frequency and Type of Mutations in the BRCA1 and BRCA2 Genes | |
|---|---|---|
| | BRCA1 Gene | BRCA2 Gene |
| Large Deletion | 3 (0.7%) | — |
| Polymorphism | 37 (8%) | 6 (2.4%) |
| Yet Unclassified | 132 (28.7%) | 76 (30%) |
| Total Number | 459 (100%) | 254 (100%) |

The Protein Truncation Test (PTT) is another diagnostic test available for the detection of loss-of-function alleles, which involves in vitro transcription and translation of the gene of interest, followed by gel electrophoretic analysis. This test is designed to detect mutations that produce a truncated protein. While this test provides an efficient means of detecting nonsense mutations, it is of no real use for detection of many other common mutations, such as frameshift, missense, inversions, and other mutations that have no detectable effect on the size of the transcribed protein.

Microarrays present another means of detecting mutations. In these assays thousands of specific oligonucleotides complementary to all known base substitutions, insertions and deletions for a gene of interest are bound to glass slides. Fluorescently labeled PCR-amplified fragments from the gene of interest are then hybridized to the microarray and binding to a particular oligonucleotide is detected. Microarrays have high up-front costs and are also not accurate at detecting heterozygous mutations. They are further limited to detection of mutations represented in the oligonucleotides.

A number of indirect methods for molecular detection of mutations exist. These include single-strand conformation polymorphism, denaturing gradient gel electrophoresis, denaturing high-performance liquid chromatography and other electrophoretic or enzymatic-based methods. Each of these methods is limited in the types of mutations it can detect and in its ability to detect heterozygous mutations in general.

To overcome the difficulty in the detection of heterozygote genotypes for inherited genetic disorders, Yan., "Conversion of diploidy to haploidy", Nature 403: 723–724 (February, 2000) (Yan (1)), Yan et al., "Genetic testing-Present and Future", Science 298: 1890–1891 (September, 2000) (Yan (2)), and Zoghbi et al., "Assignment of Autosomal Dominant Spinocerebellar Ataxia (SCA1) Centromeric to the HLA Region on the Short Arm of Chromosome 6, Using Multilocus Linkage Analysis", Am. J. Hum. Genet. 44: 255–263 (1989) have all proposed a method of genetic testing using somatic cell hybrids haploid for a chromosome of interest. This method manipulates the two copies (alleles) of a gene of interest from a donor cell by separating the two chromosomes so that each can be analyzed individually. Detection of heterozygous mutations by these methods is improved in such cells because the wild type allele has been eliminated and cannot mask the mutated allele. However, the method described requires extremely labor intensive and impractical techniques for the isolation and segregation of haploid hybrids bearing the desired chromosome in a haploid state. Further, while the nucleic acid analysis of the haploid cells would facilitate detection of exon deletions, inversions, and transcriptional defects, the approach does not offer a significant advantage over traditional methods.

Yan (2) admit that "[i]t is important to note that Conversion [the Yan et al. approach] is not a substitute for the [traditional] detection methods described above, but rather is an adjunct that provides improved nucleic acid templates that can maximize the sensitivity of conventional methods", *Science* 289, p.1892. Yan (2) further admit that "[d]isadvantages of the Conversion [Yan et al.] approach include the increased time and expense associated with the hybrid generation and screening process", *Science* 289, p.1892. Thus, while the proposed method offers an improvement over the conventional screening methods, reliance on the conventional methods is not abolished and the improvement in detection is slight, especially in light of the dramatic increases in time and expense associated with the method.

Several other methods of transferring one or multiple chromosomes to a host cell have been previously described (U.S. Pat. No. 4,806,476; WO 00/34436; U.S. Pat. No. 6,077,697). This method, microcell-mediated chromosome transfer (MMCT) was first described by Fournier and Ruddle for the transfer of murine chromosomes from one cell to another (PNAS 74: 319–323 (1977)) and by McNeill and Brown for the transfer of single human chromosomes from one cell to another (PNAS 77:5394–5398 1980). MMCT describes a way of generating microcells, by prolonged colcemid and cytochalsin B treatment of donor cells, which contain one or more chromosomes or chromosomal fragments from donor cells, and fusing them using polyethylene glycol (PEG) with target cells to generate microcell hybrids, haploid for the desired chromosome/chromosomal fragment from the donor cell (FIG. 2). While these papers presents an efficient means of generating haploid cells, they fail to describe a method employing easily obtainable donor cells. In the paper of Fournier and Ruddle, mouse embryo fibroblasts were used as donors for microcell-mediated chromosome transfer. McNeill and Brown utilized human foreskin fibroblasts as donors for human chromosome transfer.

Therefore, there is a need for a medically, veterinarily, or scientifically useful method of detecting loss-of-function mutations, including partial loss-of-function mutations, or gain-of-function mutations, including alteration of function and dominant negative mutations, in any of a variety of genes. The present invention addresses the deficiencies of the prior art by providing a method for genetic testing using easily obtainable sources of genetic material that can 1) detect many types of mutations, including nonsense, missense, frameshift, deletions, inversions, etc., 2) easily detect heterozygous and homozygous mutations, and 3) less time-consuming, labor-intensive and cheaper than known methods of genetic testing.

SUMMARY OF THE INVENTION

The present invention relates to a method for detection and interpretation of loss-of-function or gain-of-function mutations for test genes of interest. The present invention involves the process of obtaining a sample of genetic material from an individual in the form of tissue or cells, separation of the genetic material from the cells of the individuals into haploid sets by transferring the individual chromosomal entities into a population of target cells, and monitoring the target cell population for successful transfer and expression of the test genes of interest using various functional, immunological and structural assays (FIG. 1). Preferably, the test gene or genes of interest are associated with known inherited human and animal disorders.

In an embodiment of the invention, the sample of genetic material from an individual with a potential genetic abnormality is in the form of cells or tissue sample. The donor cells from the individual may be any cell type obtained from the individual. In another embodiment of the invention, the individual would provide a blood sample containing peripheral blood cells. In a further embodiment of the invention, donor cells may be lymphoblasts prepared from the individual's blood.

The genetic material comprising the test gene or genes may be located on naked DNA, plasmid, chromosome or chromosomal fragments. In a preferred embodiment of the invention, the test gene is located on a chromosome or chromosomal fragment.

In an embodiment of the invention, the separation of genetic material from donor cells into haploid sets by transfer to a population of target cells can be accomplished using various known methods of gene transfer. In a preferred embodiment of the invention, microcell mediated cell transfer (MMCT) is used to transfer genetic material to target cells.

In a preferred embodiment of the invention, the target cells may be any cell which is capable of accepting genetic material from donor cells, retaining it as a stable entity and expressing the test gene product. In a preferred embodiment of the invention, the test gene product is expressed at detectable levels. Expression of the test gene may occur through endogenous cell machinery or through cellular and molecular manipulation of cells.

In an embodiment of the invention, the presence of the test gene or genes are monitored in the target cells. In a preferred embodiment of the invention, the test gene product is monitored in the target cells. In a most preferred embodiment of the invention, the test protein is monitored. Immunofluorescence may be employed to detect test protein of interest.

In an embodiment of the invention, presence of the test gene or genes is detected by fluorescence in situ hybridization (FISH) or chromosomal painting. In yet another embodiment of the invention, the presence of the test gene is detected by fluorescent-activated cell sorting (FACS) analysis.

In another embodiment of the invention, the test gene or genes are detected though the use of a relevant functional assay for test protein function. This assay is designed based on knowledge of the cellular, immunological, molecular, biochemical, physiological, genetic, structural characteristics of the test gene product or products of interest. It takes into account all relevant functional information to design an appropriate functional assay. Assays which may be employed include, but are limited to, immunofluorescence, FACS, two-hybrid inhibition assay, ion channel activity, mismatch repair assay, and endocytic uptake of labeled LDL (low density lipoprotein).

In another embodiment of the invention, the presence of the test gene is monitored through the presence of a closely linked gene. The target cells may be monitored for either presence of linked gene or gene product, by fluorescence in situ hybridization (FISH), chromosomal painting, or fluorescent-activated cell sorting (FACS) analysis. In a preferred embodiment of the invention, known surface protein markers from specific chromosomes shared by the test gene may be used as the closely linked gene. The use of a relevant functional assay may also be employed to detect the presence of a closely linked gene and its gene products.

In another embodiment of the invention, the genotype of the donor individual may be determined by evaluating the ratio of the number of cells expressing the wild type gene product to the number of cells expressing the test gene product.

BRIEF DESCRIPTION OF THE DRAWINGS

FIGS. 10A–10D show a FACS profile of CHO cells that have taken up Human Chromosome 19 and demonstrating efficient LDL uptake. FIG. 10A highlights the analyzed cell population FIG. 10B shows FL1-control fluorescence. FIG. 10C shows FL2-dil-LDL fluorescence. FIG. 10D is a table showing the acquired measurements for the areas marked in the graphs of FIGS. 10A–C.

FIGS. 11A–11D shows fluorescence in CHO cells incubated with dil-LDL 20% of which did receive Human Chromosome 19 and 80% of which did not receive Human Chromosome 19 evaluated through LDL uptake. FIG. 11A highlights the analyzed cell population FIG. 11B shows FL1-control fluorescence. FIG. 11C shows FL2-dil-LDL fluorescence. FIG. 11D is a table showing the acquired measurements for the areas marked in the graphs of FIGS. 11A–C.

FIGS. 13A1–13A5 show expression of ICAM-1 in mouse L cells through FACS. FIG. 13A1 highlights the analyzed cell population FIG. 13A3 shows FL2-control fluorescence. FIG. 13A4 shows FL1-FITC-anti-ICAM-1 fluorescence. FIG. 13A2 plots FL2-control fluorescence v. FL1-FITC-anti-ICAM-1 fluorescence. FIG. 13A5 is a table showing the acquired measurements for the areas marked in the graphs of FIGS. 13A1–13A4.

FIGS. 13B1–13B5 show that ICAM-1 negative mouse L cells are also distinguishable by FACS. FIG. 13B1 highlights the analyzed cell population. FIG. 13B3 shows FL2-control fluorescence. FIG. 13B4 shows FL1-FITC-anti-ICAM-1 fluorescence. FIG. 13B2 plots FL2-control fluorescence v. FL1-FITC-anti-ICAM-1 fluorescence. FIG. 13B5 is a table showing the acquired measurements for the areas marked in the graphs FIGS. 13B1–13B4.

FIGS. 14A–14E show the FACS analysis detection of ICAM-1 or LDLR in a somatic cell hybrid that originally contained Human Chromosome 19, but in which some cells have undergone spontaneous loss of the chromosome. FIG. 14A highlights the analyzed cell population FIG. 14C shows FL2-dil-LDL fluorescence. FIG. 14D shows FL1-FITC-anti-ICAM-1 fluorescence. FIG. 14B plots FL2-dil-LDL fluorescence v. FL1-FITC-anti-ICAM-1 fluorescence. FIG. 14E is a table showing the acquired measurements for the areas marked in the graphs of FIGS. 14A–14D.

FIGS. 15A1–15A5 show the results of FACS analysis for ICAM-1 and LDLR for a normal individual. FIGS. 15B1–15B5 show the results of FACS analysis for ICAM-1 and LDLR for another normal individual. FIGS. 15A1 and 15B1 highlight the analyzed the cell population. FIGS. 15A4 and 15B4 show FL2-dil-LDL fluorescence. FIGS. 15A3 and 15B3 show FL1-FITC-anti-ICAM-1 fluorescence. FIGS. 15A2 and 15B2 plot FL2-dil-LDL fluorescence v. FL1-FITC-anti-ICAM-1 fluorescence. FIG. 15A5 also shows scatter of cells for the normal individual of FIGS. 15A1–15A4. FIGS. 15A6 and 15B5 show tables listing the acquired measurements for the areas marked in the graphs of FIGS. 15A1–15A3 and 15B1–15B3.

FIGS. 16A1–16A5 show the result of FACS analysis for ICAM-1 and LDLR for an individual heterozygous for a loss-of-function mutation in the LDLR gene. FIG. 16A1 highlights the analyzed the cell population. FIG. 16A4 shows FL2-dil-LDL fluorescence. FIG. 16A3 shows FL1-FITC-anti-ICAM-1 fluorescence. FIG. 16A2 plots FL2-dil-LDL fluorescence v. FL1-FITC-anti-ICAM-1 fluorescence. FIG. 16A5 also shows the scatter of cells for the normal individual of FIGS. 16A1–16A4. FIG. 16A5 is a table showing the acquired measurements for the areas marked in the graphs of FIGS. 16A1–16A4.

FIGS. 16B1 and 16B2 show the result of FACS analysis for ICAM-1 and LDLR for another individual heterozygous for a loss-of-function mutation in the LDLR gene. FIG. 16B1 plots FL2-dil-LDL fluorescence v. FL1-FITC-anti-ICAM-1 fluorescence. FIG. 16B2 is a table showing the acquired measurements for the areas marked in FIG. 16B1.

FIGS. 17A1–17A5 show the result of FACS analysis for ICAM-1 and LDLR for an individual homozygous for a loss-of-function mutation in the LDLR gene. FIGS. 17B1–17B5 show the result of FACS analysis for ICAM-1 and LDLR for another individual homozygous for a loss-of-function mutation in the LDLR gene. FIGS. 17A1 and 17B1 highlight the analyzed cell population FIGS. 17A4 and 17B4 show FL2-dil-LDL fluorescence. FIGS. 17A3 and 17B3 show FL1-FITC-anti-ICAM-1 fluorescence. FIGS. 17A2 and 17B2 plot FL2-dil-LDL fluorescence v. FL1-FITC-anti-ICAM-1 fluorescence. FIGS. 17A5 and 17B5 show tables listing the acquired measurements for the areas marked in the graphs of FIGS. 17A1–17A4 and 17B1–15B4.

FIGS. 18A1–A6 show the result of FACS analysis for ICAM-1 and LDLR for control cells. FIG. 18A1 highlights the analyzed cell population FIG. 18A4 shows FL2-dil-LDL fluorescence. FIG. 18A3 shows FL1-FITC-anti-ICAM-1 fluorescence. FIG. 18A2 plots FL2-dil-LDL fluorescence v. FL1-FITC-anti-ICAM-1 fluorescence. FIG. 18A5 shows a table listing the acquired measurements for the areas marked in the graphs of FIGS. 18A1–18A4.

FIGS. 18B1–18B6 also show the results of FACS analysis for ICAM-1 and LDLR for control cells. FIG. 18B1 highlights the analyzed the cell population. FIG. 18B4 shows FL2-dil-LDL fluorescence. FIG. 18B3 shows FL1-FITC-anti-ICAM-1 fluorescence. FIG. 18B2 volts FL2-dil-LDL fluorescence v. FL1-FITC-anti-ICAM-1 fluorescence. FIG. 18B5 also shows the scatter of cells for the normal individual of FIGS. 16A1–16A4. FIG. 18B6 is a table showing the acquired measurements for the areas marked in the graphs of FIGS. 18B1–18B5.

DETAILED DESCRIPTION OF THE INVENTION

The present invention provides a method for detecting and interpreting loss-of-function or gain-of-function mutations in a variety of genes. Loss-of-function and gain-of-function mutations, including dominant negative mutations, cause many known diseases and disorders in humans, including breast and ovarian cancer, familial hypercholesterolemia, hereditary nonpolyposis colon cancer (HNPCC), neurofibromatosis, polyposis of the colon, Duchenne dystrophy, cystic fibrosis, Li Fraumeni disease, tuberous sclerosis, Gorlin syndrome, Von Hippel-Lindau disease, porphyrias, osteogenesis imperfecta, Marfan's disease, polycystic kidney disease, hemophilia, SCID, Rett syndrome, lysosomal diseases, and ornithine transcarbamylase (OTC) deficiency. Detection of loss-of-function and gain-of-function mutations that can result in these and other diseases may be useful for inter alia, laboratory research, medical diagnosis leading to proper counseling and treatment of those afflicted with the diseases at both the pre and post natal stages of development, and genetic testing for potential carriers of various diseases. The techniques described may also be used to detect loss-of-function or gain-of-function mutations in animals. Humans are not alone in our affliction with diseases resulting from such mutations; animal research, veterinary science and practice, and animal husbandry will also benefit by detecting loss-of-function and gain-of-function mutations in animals and employing that knowledge to better treat and breed animals.

Figure 1:
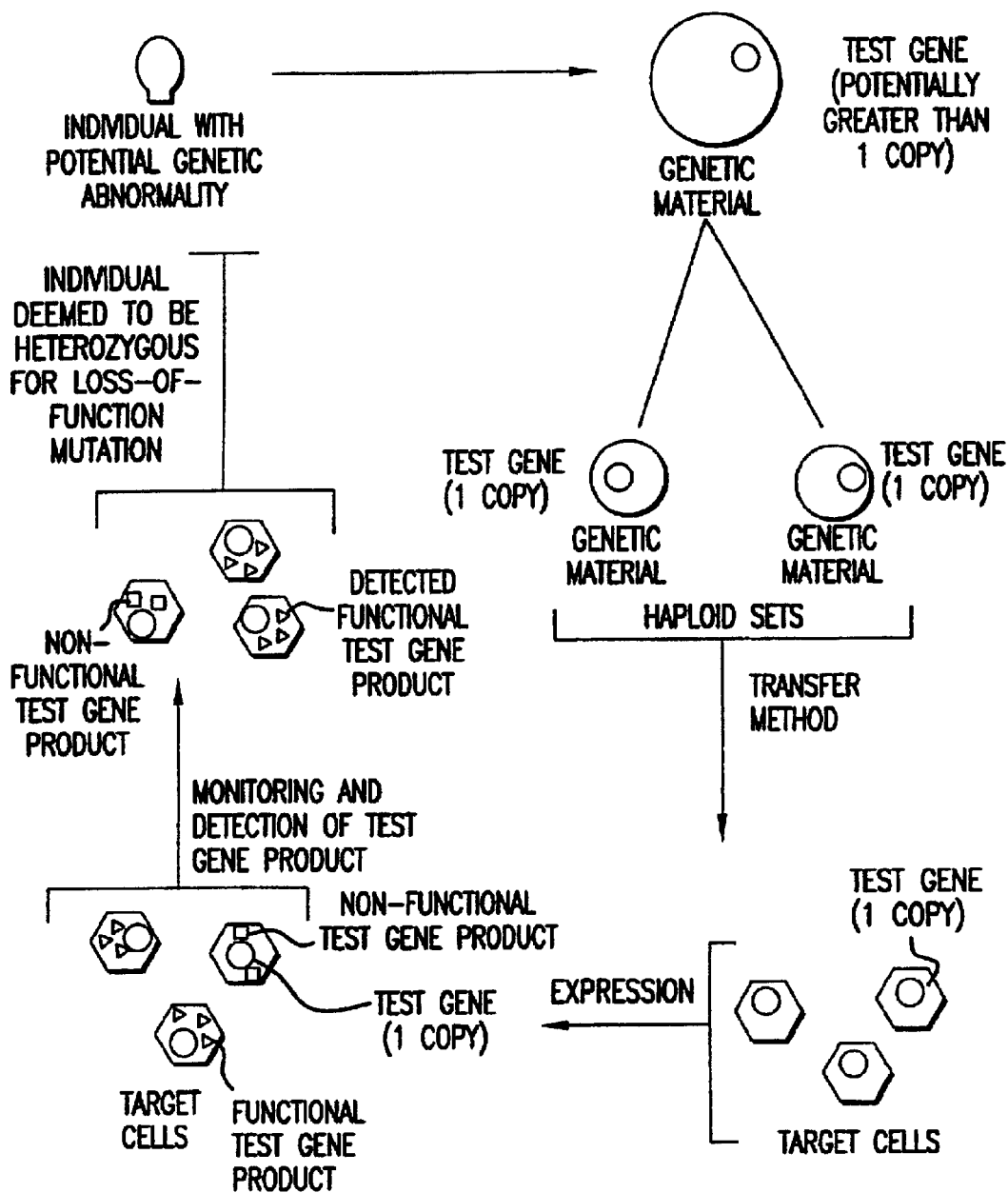
FIG. 1 shows the general steps of the method of the present invention when used to detect a loss-of-function mutation.
Figure 2:
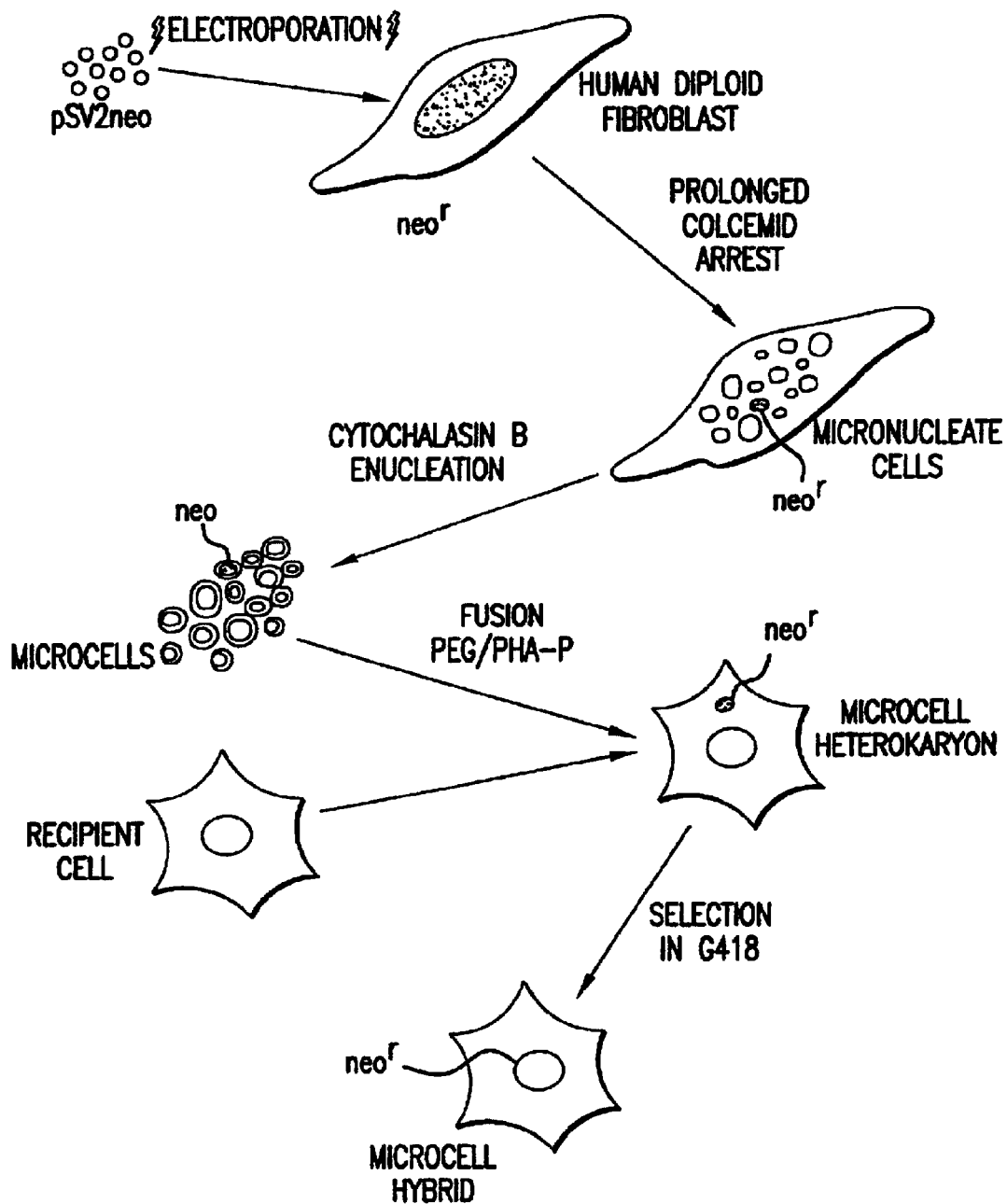
FIG. 2 shows MMCT as described by Killary et al.

The present invention provides a method of detecting loss-of-function or gain-of-function mutations in individuals homozygous or heterozygous for a genetic abnormality by separating the two chromosomes from an individual donor cell so that each copy of the gene from the chromosome can be analyzed individually. The analysis requires the genetic transfer of each chromosome to a target cell population to produce somatic cell hybrids. This allows for haploid analysis of each chromosomal entity. Separation of the two copies of the gene facilitate the detection of heterozygous mutations. The wild type alleles can often mask the effect of the mutant allele in various methods of genetic testing. Individual cells from the hybrid populations can then be scored for presence or absence of the test gene of interest. FIG. 1 shows a schematic of the invention to detect a heterozygous loss-of-function mutation.

The term "test gene" as used here and throughout the specification may refer to the traditional concept of a gene or the gene and its flanking syntenic DNA. The amount of genetic material designated as the "test gene" will vary depending on the location and type of mutation to be detected. For instance, the "test gene" may encompass a large flanking region if a deletion is to be detected. Furthermore, the test gene product may be referred to as the test protein through the specification and claims, as this is the gene product that will most commonly be examined with this method. However, one skilled in the art will appreciate that the test gene product may encompass nucleic acids and protein molecules.

Though the term test gene is used in the above summary and throughout the specification and claims, it will be understood to one skilled in the art that in other embodiments of the invention more than one test gene may be transferred to from the donor cell to the target cell. The target cells may be assayed for the presence of the each test gene separately, or, if the test genes are linked, one assay may confirm the presence of all test genes. Further, different functional or immunological assays may be performed to detect functional or wild type protein expression for each test gene separately or, if the genes function in concert, a single assay that requires functional or wild type expression of each gene may be employed.

Source of Donor Cells

To practice the invention, a sample of genetic material which is collected from an individual with a known potential genetic abnormality is collected as a cell or tissue sample. Blood is a common source of genetic material used for genetic testing. Lymphoblasts are an potential important source of cultured cells and may also be obtained from blood. A mitogen, such as phytohemagglutanin, can be used to induce lymphoblasts from peripheral blood cells. Cells may be obtained from any bodily fluids or tissues, including tissue from biopsies. Other somatic and gamete cells may also be used. Cells such as lymphoblasts and sperm cells have the advantage of being easily obtainable. However, any cell type or mixture of cell types is appropriate, provided that the cells may be obtained in sufficient quantities to allow transfer of the test gene from donor to target cells.

Genetic Transfer

In an embodiment of the invention, the test gene of interest is detected in a hybrid target cell population after genetic transfer to allow for haploid analysis of each copy of the test gene. The transfer of the test gene or genes is accomplished through transfer of genetic material comprising the test gene or genes.

Numerous mechanisms for transferring a gene from one cell to another are known to the art. Any such mechanism presently known or later developed is suitable for the transfer of the test gene so long as the mechanism results in the transfer of only one copy of the test gene to substantially all target cells or a distinguishable portion of target cells that receive the test gene. The transfer may be performed by means yet to be discovered or by mechanisms known to one skilled in the art. Such mechanisms include microcell-mediated chromosome transfer (MMCT), electroporation, liposome-mediated gene transfer, somatic cell fusion, gamete cell fusion, injection of gamete cells into target cells, biolistic transfer and other known transfection protocols. See Killary, A., et al., "Functional Studies to Identify Tumor Suppressor Genes", *Methods: A Companion to Methods in Embryology* 8: 234–246 (1995); Yan, H., "Conversion of Diploidy to Haploidy", *Nature* 403, 723–724 (Feb. 17, 2000); WO 00/34436, "FACS Assisted Methods for Introducing Individual Chromosomes Into Cells" to Nolan, E. et al. (Jun. 15, 2000); U.S. Pat. No. 6,077,697, "Artificial Chromosomes, Uses Thereof and Methods for Preparing Artificial Chromosomes", to Hadlaczky, G. et al. (Jun. 20, 2000); U.S. Pat. No. 4,806,476, "Efficient Cell Fusion Process" to Coons, T. et al. (1989); Aslam, I., et al., "Evaluation of the fertilization potential of freshly isolated, in-vitro cultured and cryopreserved human spermatids by injection into hamster oocytes", *Hum. Reprod.* 14: 1528 (1999); U.S. Pat. No. 4,806,476; WO 00/34436; U.S. Pat No. 6,077,692; Yan et al. (2000); Johnston, S. A. and Tang, D. C., "The use of microparticle injection to introduce genes into animal cells in vitro and in vivo", *Genet. Eng.* (N.Y.) 15: 225–236 (1993); Sanford, J. C., et al., "Optimizing the biolistic process for different biological applications", *Methods Enzymol.* 217: 483–509 (1993), incorporated herein by reference, for examples of some potential transfer methods.

To practice the invention, many techniques for gene transfer may be applied as indicated above. These mechanisms can apply since the test gene may be a located on an excised piece of native DNA, on a plasmid, on a chromosome or chromosomal fragment. Depending on the desired comprehensiveness of the assay, the test gene may comprise the entire native gene with most regulatory elements or it may comprise fewer elements down to a portion of an exon artificially located in a construct that will allow its expression in the target cells. In a preferred embodiment of the invention, use of the entire gene and its regulatory elements, as will be possible with MMCT, will encompass a greater range of possible loss-of-function or gain-of-function mutations. However, for many research, diagnostic and other purposes, only mutations in a portion of the gene and its regulatory elements may be of interest.

Target Cells

To practice the invention, the target cell must be carefully chosen to ensure that cells are susceptible to desired methods for gene transfer. The cells must be amenable to DNA transfer techniques described above. These target cells may include but not be limited to the following primary and transformed cell lines, mammalian, murine, insect, yeast cells and Chinese Hamster ovary (CHO) cells.

The target cells must also be chosen to ensure optimal detection of test gene or test gene products. In a preferred embodiment of the invention, the presence of the test gene is evaluated through detection of the test gene products. As a result, the target cell must possess gene-specific machinery required for expression of test gene. For detection of a test gene that is ubiquitously expressed, nearly any cell type may serve as target cells. Some ubiquitously expressed genes that may be assayed by the present invention include those encoding the low density lipoprotein receptor (LDLR) (associated with familial hypercholsterolemia), BRCA1, BRCA2 (associated with breast and ovarian cancer), NF1, NF2 (associated with neurofibromatosis), APC (associated with polyposis of the colon), and various genes associated with hereditary nonpolyposis colon cancer. Test genes which are not ubiquitously expressed will require a target cell that can express the test gene. This may involve using a tissue-specific cell type that can endogenously express the gene product or manipulation of the target cells to achieve expression of the test gene in the hybrid cell population. One skilled in the art will be aware of various cell, molecular, immunological, biochemical, pharmacological methods commonly used in the art to produce such a cell line.

In a preferred embodiment of the invention, the presence of the test gene will be evaluated through detection of the translated test protein. In this scenario, the target cell must be chosen to provide an environment in which the test protein expression or test protein function of the test gene can be assayed. In particular, the target cell should not express orthologs or other proteins that may interfere with the chosen assays for expression or function of the test protein. To overcome problems resulting from interfering proteins expressed endogenously by the target cell, one may apply various cell, molecular, immunological, biochemical, pharmacological methods commonly used in the art to prevent this expression. For example, the target cell may be induced to inhibit expression of ortholog or other protein. In addition, one may alter the assay in order to only detect the test protein of interest. An antibody that does not cross react with the endogenous protein may be used.

In addition, one may choose a target cell that lacks the ortholog or other protein which interferes with the detection assay. These cells may be either a genetically or functional knockout cell line. For example, Chinese Hamster Ovary (CHO) cells are appropriate for assays involving the low density lipoprotein receptor (LDLR), since CHO cells do not express LDLR, but have been shown capable of expressing the fully funtional protein in Corsetti, et al (1991). Such a cell line would then allow functional analysis of the test gene product. Examples of such potential target cells include human or mouse cell lines with homozygous mutations leading to complete deficiency of the human or mouse BRCA1 or BRCA2 gene product. Other examples would be human or rodent cell lines genetically deficient for mismatch repair enzymes such as MSH2, MLH1, PMS1 or PMS2, such that the target cells could be analyzed for function of a human mismatch repair gene. Such analysis might comprise testing the target cells for microsatellite instability using a test system introduced after gene transfer. As mentioned above, yeast cells have great potential as target cells because of the presence of many mutant strains. They are additionally valuable because of the ease with which deficiencies may be induced.

Detection of Target Gene Transfer

Following the successful transfer of the test gene from the donor cells to the target cells, it becomes necessary to detect the presence of absence of the gene in the target cells. This can be accomplished in multiple ways and the optimal strategy depends on the method for overall analysis of the cells. The assay need only detect that transfer of the test gene occurred. It need not detect the number of copies of the test gene, as only transfer methods that rarely result in transfer of more than one copy of the test gene to any target cell are suitable for this method.

Detection of DNA or Chromosome

FISH (fluorescence in situ hybridization) may be used to determine the presence or absence of a copy of the test gene in a target cell using various cloned DNA fragments such as YACs, BACs, or PACs and the standard techniques. FISH may be accomplished by many methods depending on the test gene and cell types, but some possible methods may be found in the Savage, J. R. and Tucker, J. D., "Nomenclature systems for FISH-painted chromosome aberrations", *Mutat. Res.* 366(2): 153–156 (1996) and Bickmore, W., "Fluorescence in situ hybridization of chromosome and chromatin structure", *Methods Enzymol.* 304: 650–662 (1999), incorporated herein by reference. FISH is most suitable for analysis on microscope slides, but it may be possible to use this approach in combination with fluorescence activated cell sorting (FACS).

Chromosome paint is another alternative for detecting the presence or absence of the test gene. Chromosome paint may be performed as described in Lichter, P. et al., "Detection of chromosomal aberrations by means of molecular cytogenetics: painting of chromosomes and chromosomal subregions and comparative genomic hybridization", *Methods in Enzymology* 254: 334–359 (1995); and Tucker, J. D., et al., "PAINT: A proposed nomenclature for structural aberrations detected by whole chromosome painting", *Mutat. Res.* 347 (1): 21–24 (1995), incorporated herein by reference. If a method that transfers most or all of a chromosome, such as MMCT, is used, chromosome paint detection may be efficient. Although the chromosome may become fragmented in a small number of the cells, this should not interfere with the analysis. Like FISH, chromosome paint is most suitable for analysis on microscopic slides. However, chromosome paint may also be coupled with FACS for easier detection and would prove more effective with FACS than would FISH with a single copy probe.

Detection of Protein Gene Product

In a most preferred embodiment, the hybrid target cell population is evaluated for presence or absence of the test gene by detection of protein gene product. The functional protein may be detected by immunological analysis designed to detect primarily functional or wild type proteins. Commercial antibodies are available for various epitopes of the protein. Thus, one may test with one or more antibodies to assess the presence of the protein. The antibodies used for detection must be able to distinguish the mutant test protein from the wild type functional protein. In the scenario of a test gene that expresses a missense mutation, an antibody which recognizes an epitope specific to the full length protein may be used. An immunological test could be performed as immunostaining of target cells on slides or with FACS. Analysis could also be performed using western blots to detect any protein products of abnormal size. One example of immunological detection is provided in Marcus, V. A., et al., "Immunohistochemistry for hMLH1 and hMLH2: a practical test for DNA mismatch repair-deficient tumors", *Am. J Surg. Pathol.* 23: 1248 (1999), incorporated by reference herein.

Linked Genes

Figure 3:
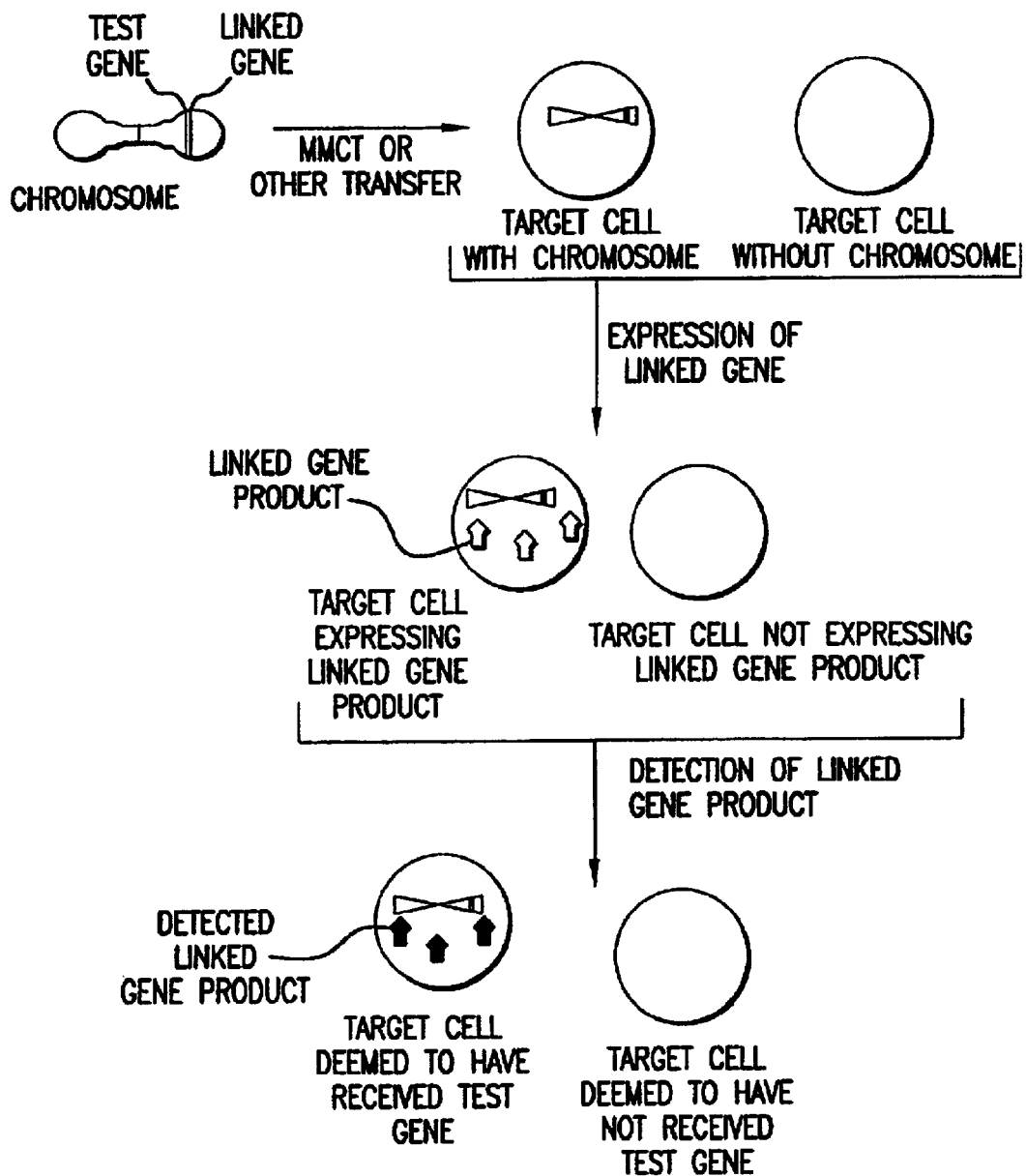
FIG. 3 shows an assay that may be used to detect the gene product of a gene linked to the test gene. Detection of a linked gene indicate which target cells have received the target gene.

In another embodiment of the invention, the presence of the test gene is monitored through the presence of a closely linked gene. For some test genes, an assay for a closely linked gene may prove to be a more efficient means of detecting target cells that have received the test gene. (See FIG. 3 for a basic description of such an assay.) Use of this analysis requires that the form of genetic material and method of transfer employed allow transfer of the linked gene to the target cell. Transfer of a chromosome or chromosome fragment by MMCT is an appropriate method for genetic transfer of a test gene and its linked gene. The linked gene should be chosen so that recombination or chromosomal degradation are unlikely to result in its separation from the test gene before or after transfer to the target cell.

This type of analysis has the added advantage of excluding any cells that received the test gene, but are incapable of expressing the test gene product properly for reasons unrelated to the allele present. However, when employing this type of assay one must take care to choose target cells capable of expressing the linked gene product and that do not express orthologs or other protein which may interfere with a functional assay.

The detection of the linked gene may occur through fluorescence in situ hybridization (FISH), or chromosome paint methods. Further, FISH and chromosome paint methods may also be coupled with FACS (fluorescence activated cell sorting) to separate target cells that have received the test gene from those that have not.

Similarly, the detection of the linked gene may occur through detection of the translated protein. Immunodetection, FACS analysis and functional assay may be applied to locate the subset of the target population that expresses the translated protein for the linked gene. The linked gene may also encode a surface protein, which can be detected through immunodetection or FACS analysis.

Known surface antigens and their human chromosome location are listed in Tables 2–25. Each of these surface antigens, as well as those not listed and not yet discovered may serve as an appropriate linked genes in an assay to determine whether a particular test gene has been received by the target cell.

TABLE 2

Surface Antigens of Human Chromosome 1

| Long Name | Abbreviation |
| --- | --- |
| MEMBRANE COMPONENT, CHROMOSOME 1, SURFACE MARKER 1 | M1S1 |
| PHOSPHODIESTERASE I/INCLEOTIDE PYROPHOSPHATES 1 | PDNP1 |
| FLOTILLIN 2 | FLOT2 |
| MUSCULAR DYSTROPHY, PSEUDOHYPERTROPHIC PROGRESSIVE, DUCHENNE AND BECKER TYPES | |
| TRANSMEMBRANE 4 SUPERFAMILY, MEMBER 1 | TM4SF1 |
| HEMOGLOBIN--BETA LOCUS | HBB |
| LETHAL ANTIGEN--Al | AL-A1 |
| HEMOPHILIA A | |
| WILMS TUMOR 1 | WT1 |
| ATP-BINDING CASSETTE, SUBFAMILY B, MEMBER 2 | ABCB2 |
| MEMBRANE COMPONENT, CHROMOSOME 4, SURFACE MARKER 1 | M4S1 |
| LEUKOCYTE ADHESION DEFICIENCY TYPE I | LAD |
| THY-1 T-CELL ANTIGEN | THY1 |
| ATAXIA-TELANGIECTASIA | AT |
| INTERFERON, GAMMA, RECEPTOR 1 | IFNGR1 |
| INTERCELLULAR ADHESION MOLECULE 1 | ICAM1 |
| INTEGRIN, BETA-3 | ITGB3 |
| CD80 ANTIGEN | CD80 |
| T-LYMPHOCYTE SURFACE CD2 ANTIGEN | CD2 |
| RETINOBLASTOMA | RB1 |
| RHESUS BLOOD GROUP, CcEe ANTIGENS | RHCE |
| SOLUTE CARRIER FAMILY 4, ANION EXCHANGER, MEMBER 1 | SLC4A1 |
| TUMOR NECROSIS FACTOR RECEPTOR SUPERFAMILY, MEMBER 6 | TNFRSF6 |
| CYSTIC FIBROSIS TRANSMEMBRANE CONDUCTANCE REGULATOR | CFTR |
| BRUTON AGAMMAGLOBULINEMIA TYROSINE KINASE | BTK |
| KANGAI 1 | KAI1 |
| PROTEIN-TYROSINE PHOSPHATASE, NONRECEPTOR TYPE, SUBSTRATE 1 | PTPNS1 |
| THYMOCYTE ANTIGEN CD1A | CD1A |
| CHEDIAK-HIGASHI SYNDROME | CHS1 |
| HEMOCHROMATOSIS | HFE |
| LUPUS ERYTHEMATOSUS, SYSTEMIC | SLE |
| T-LYMPHOCYTE SURFACE ANTIGEN LY-9 | LY9 |
| FACTOR V DEFICIENCY | |
| ALZHEIMER DISEASE | AD |
| INTEGRIN, BETA-2 | ITGB2 |
| ANTITHROMBIN III DEFICIENCY | |
| BULLOUS PEMPHIGOID ANTIGEN 1 | BPAG1 |
| SELECTIN | SELL |

TABLE 2-continued

Surface Antigens of Human Chromosome 1

| Long Name | Abbreviation |
| --- | --- |
| TUMOR PROTEIN p53 | TP53 |
| SOLUTE CARRIER FAMILY 3, MEMBER 1 | SCLC3A1 |
| PROTEIN-TYROSINE PHOSPHATASE, RECEPTOR-TYPE, C | PTPRC |
| INTEGRIN, BETA-1 | ITGB1 |
| HEPATOCELLULAR CARCINOMA | |
| PREGNANCY-SPECIFIC BETA-1-GLYCOPROTEIN 2 | PSG2 |
| INTEGRIN, ALPHA-L | ITGAL |
| TUMOR NECROSIS FACTOR LIGAND SUPERFAMILY, MEMBER 6 | TNFSF6 |
| DECAY-ACCELERATING FACTOR FOR COMPLEMENT | DAF |
| TUMOR NECROSIS FACTOR RECEPTOR SUPERFAMILY, MEMBER 4 | TNFRSF4 |
| AGGRECAN 1 | AGC1 |
| MAJOR HISTOCOMPATIBILITY COMPLEX, CLASS I, A | HLA-A |

TABLE 3

Surface Antigens of Human Chromosome 2

| Long Name | Abbreviation |
| --- | --- |
| MEMBRANE COMPONENT, CHROMOSOME 4, SURFACE MARKER 1 | M4S1 |
| HEMOGLOBIN--BETA LOCUS | HBB |
| HEMOPHILIA A | |
| FLOTILLIN 2 | FLOT2 |
| MEMBRANE COMPONENT, CHROMOSOME 17, SURFACE MARKER 2 | M17S2 |
| MUSCULAR DYSTROPHY, PSEUDOHYPERTROPHIC PROGRESSIVE, DUCHENNE AND BECKER TYPES | |
| ATAXIA-TELANGIECTASIA | AT |
| WISKOTT-ALDRICH SYNDROME | WAS |
| RETINOBLASTOMA | RBI |
| DIPEPTIDYLPEPTIDASE IV | DPP4 |
| INTEGRIN, BETA-2 | ITGB2 |
| CD86 ANTIGEN | CD86 |
| HEMOCHROMATOSIS | HFE |
| ITEGRIN, ALPHA-2 | ITGA2 |
| SOLUTE CARRIER FAMILY 3, MEMBER 2 | SLC3A2 |
| WILMS TUMOR 1 | WT1 |
| CD8 ANTIGEN, ALPHA POLYPEPTIDE | CD8A |
| V-ERB-B2 AVIAN ERYTHROBLASTIC LEUKEMIA VIRAL ONCOGENE HOMOLOG 2 | ERBB2 |
| CYSTIC FIBROSIS TRANSMEMBRANE CONDUCTANCE REGULATOR | CFTR |
| BETA-2MICROGLOBULIN | B2M |
| ITERLEUKIN 2 RECEPTOR, ALPHA | IL2RA |
| ALZHEIMER DISEASE | AD |
| MAJOR HISTOCOMPATABILITY COMPLEX, CLASS I, A | HLA-A |
| DIABETES INSIPIDUS, NEPHROGENIC, X-LINKED | |
| TUMOR PROTEIN p53 | TP53 |
| MEMBRANE COMPONENT, CHROMOSOME 6, POLYPEPTIDE 2 | M6P2 |
| ANTIGEN DEFINED BY MONOCLONAL ANTIBODY F10.44.2 | |
| INTERLEUKIN 2 RECEPTOR, GAMMA | IL2RG |
| ADENOSINE DEAMINASE | ADA |
| MEMBRANE-SPANNING 4 DOMAINS, SUBFAMILY A, MEMBER 2 | MS4A2 |
| PREGNANCY-SPECIFIC BETA-1-GLYCOPROTEIN 2 | PSG2 |
| ATP-BINDING CASSETTE, SUBFAMILY B, MEMBER 2 | ABCB2 |
| VON WILLEBRAND DISEASE | |
| INSULIN-LIKE GROWTH FACTOR 2 RECEPTOR | IGF2R |
| BRUTON AGAMMAGLOBULINEMIA TYROSINE KINASE | BTK |
| ANTIGEN CD28 | CD28 |
| LEUKOCYTE ADHESION DEFICIENCY, TYPE 1 | LAD |
| RHESUS BLOOD GROUP, CcEe ANTIGENS | RHCE |
| MEMBRANE COMPONENT, CHROMOSOME 1, SURFACE MARKER 1 | M1S1 |
| LOW DENSITY LIPOPROTEIN RECEPTOR-RELATED PROTEIN-ASSOCIATED PROTEIN | LRPAP1 |
| INTEGRIN, BETA-3 | ITGB3 |
| SOLUTE CARRIER FAMILY 3, MEMBER 1 | SLC3A1 |
| IMMUNODEFICIENCY, PARTIAL COMBINED, WITH ABSENCE OF HLA DETERMINANTS AND BETA-2-MICROGLOBULIN FROM LYMPHOCYTES | |
| ZETA-CHAIN-ASSOCIATED PROTEIN KINASE | ZAP70 |
| IMMUNODEFICIENCY WITH HYPER-IgM | |
| THROMBASTHENIA OF GLANZMANN AND NAEGELI | |
| ANTITHROMBIN III DEFICIENCY | |
| T-CELL ANTIGEN RECEPTOR, GAMMA SUBUNIT | TCRG |

TABLE 3-continued

Surface Antigens of Human Chromosome 2

| Long Name | Abbreviation |
| --- | --- |
| INTERLEUKIN 2 RECEPTOR, BETA | IL2RB |
| ANTIGEN DEFINED BY MONOCLONAL ANTIBODY TRA-2-10 | M1C10 |

TABLE 4

Surface Antigens of Human Chromosome 3

| Long Name | Abbreviation |
| --- | --- |
| TRANSMEMBRANE 4 SUPERFAMILY, MEMBER 1 | TM4SF1 |
| HEMOGLOBIN--BETA LOCUS | HBB |
| ATAXIA-TELANGIECTASIA | AT |
| HEMOPHILIA A | |
| SOLUTE CARRIER FAMILY 4, ANION EXCHANGER, MEMBER 1 | SLC4A1 |
| INTEGRIN, BETA-3 | ITGB3 |
| MUSCULAR DYSTROPHY, PPSEUDOHYPERTROPHIC PROGRESSIVE, DUCHENNE AND BECKER TYPES | |
| IMMUNODEFICIENCY WITH HYPER-IgM | |
| RETINOBLASTOMA | RB1 |
| SOLUTE CARRIER FAMILY 3, MEMBER 2 | SLC3A2 |
| FUCOSYLTRANSFERASE 4 | FUT4 |
| WILMS TUMOR 1 | WT1 |
| CD80 ANTIGEN | CD80 |
| CYSTIC FIBROSIS TRANSMEMBRANE CONDUCTANCE REGULATOR | CFTR |
| TRANSFERRIN | TF |
| HEMOCHROMATOSIS | HFE |
| CD47 ANTIGEN | CD47 |
| MAJOR HISTOCOMPATIBILITY COMPLEX, CLASS 1, A | HLA-A |
| TRANSFERRIN RECEPTOR | TFRC |
| DISACCHARIDE INTOLERANCE 1 | |
| CD86 ANTIGEN | CD86 |
| DESMOGLEIN 3 | DSG3 |
| LYMPHOCYTE FUNCTION-ASSOCIATED ANTIGEN, TYPE 3 | LFA3 |
| MELANOMA-ASSOCIATED ANTIGEN p97 | MF12 |
| TUMOR PROTEIN p53 | TP53 |
| ALZHEIMER DISEASE | AD |
| BRUTON AGAMMAGLOBULINEMIA TYROSINE KINASE | BTK |
| VON WILLEBRAND DISEASE | |
| THROMBASTHENIA OF GLANZMANN AND NAEGELI | |
| SOLUTE CARRIER FAMILY 3, MEMBER 1 | SLC3A1 |
| MEMBRANE METALLOENDOPEPTIDASE | MME |
| WISKOTT-ALDRICH SYNDROME | WAS |
| LEUKOCYTE ADHESION DEFICIENCY, TYPE 1 | LAD |
| RHESUS BLOOD GROUP, CcEe ANTIGENS | RHCE |
| FLAUJEAC FACTOR DEFICIENCY | |
| CD151 ANTIGEN | CD151 |
| ADENOSINE DEAMINASE | ADA |
| INTEGRIN, ALPHA-M | ITGAM |
| T-CELL ANTIGEN RECEPTOR, ALPHA SUBUNIT | TCRA |
| TUMOR NECROSIS FACTOR RECEPTOR SUPERFAMILY, MEMBER 6 | TNFRSF6 |
| T-LYMPHOCYTE SURFACE CD2 ANTIGEN | CD2 |
| V-HA-RAS HARVEY RAT SARCOMA VIRAL ONCOGENE HOMOLOG | HRAS |
| ANTITHROMBIN III DEFICIENCY | |
| CHEDIAK-HIGASHI SYNDROME | CHS1 |
| FACTOR V DEFICIENCY | |
| SEVERE COMBINED IMMUNODEFICIENCY, X-LINKED | SCIDX1 |
| GOLGI AUTOANTIGEN, GOLGIN SUBFAMILY A, 4 | GOLGA4 |
| SIALYLTRANSFERASE 1 | SIAT1 |
| PHOSPHODIESTERASE I/NUCLEOTIDE PYROPHOSPHATASE 1 | PDNP1 |
| INTEGRIN, BETA-2 | ITGB2 |

TABLE 5

Surface Antigens of Human Chromosome 4

| Long Name | Abbreviation |
| --- | --- |
| MEMBRANE COMPONENT, CHROMOSOME 4, SURFACE MARKER 1 | M4S1 |
| TRANSMEMBRANE 4 SUPERFAMILY, MEMBER 1 | TM4SF1 |

TABLE 5-continued

Surface Antigens of Human Chromosome 4

| Long Name | Abbreviation |
| --- | --- |
| INTEGRIN, BETA-3 | ITGB3 |
| HEMOPHILIA A | |
| SOLUTE CARRIER FAMILY 4, ANION EXCHANGER, MEMBER 1 | SLC4A1 |
| HEMOGLOBIN--BETA LOCUS | HBB |
| FUCOSYLTRANSFERASE 4 | FUT4 |
| ATAXIA-TELANGIECTASIA | AT |
| MUSCULAR DYSTROPHY, PSEUDOHYPERTROPHIC PROGRESSIVE, DUCHENNE AND BECKER TYPES | |
| SEVERE COMBINED IMMUNODEFICIENCY, X-LINKED | SCIDX1 |
| BLOOD GROUP--MN LOCUS | MN |
| RETINOBLASTOMA | RB1 |
| CYSTIC FIBROSIS TRANSMEMBRANE CONDUCTANCE REGULATOR | CFTR |
| WILMS TUMOR 1 | WT1 |
| INTERLEUKIN 4 RECEPTOR | IL4R |
| ALZHEIMER DISEASE | AD |
| HEMOCHROMATOSIS | HFE |
| ANTIGEN CD38 OF ACUTE LYMPHOBLASTIC LEUKEMIA CELLS | CD38 |
| MEMBRANE-SPANNING 4 DOMAINS, SUBFAMILY A, MEMBER 2 | MS4A2 |
| CENTROMERIC PROTEIN C1 | CENPC1 |
| MEMBRANE-SPANNING 4 DOMAINS, SUBFAMILY A, MEMBER 1 | MS4A1 |
| TUMOR PROTEIN p53 | TP53 |
| SIGNAL TRANSDUCER AND ACTIVATOR OF TRANSCRIPTION 6 | STAT6 |
| LOW DENSITY LIPOPROTEIN RECEPTOR-RELATED PROTEIN-ASSOCIATED PROTEIN 1 | LRPAP1 |
| WISKOTT-ALDRICH SYNDROME | WAS |
| TUMOR NECROSIS FACTOR RECEPTOR SUPERFAMILY, MEMBER 4 | TNFRSF4 |
| TUMOR NECROSIS FACTOR LIGAND SUPERFAMILY, MEMBER 4 | TNFSF4 |
| BLOOD GROUP--Ss LOCUS | Ss |
| IMMUNODEFICIENCY WITH HYPER-IgM | |
| MEMBRANE COMPONENT, CHROMOSOME 1, SURFACE MARKER 1 | M1S1 |
| BRUTON AGAMMAGLOBULINEMIA TYROSINE KINASE | BTK |
| VON WILLEBRAND DISEASE | |
| MAJOR HISTOCOMPATIBILITY COMPLEX, CLASS I, A | HLA-A |
| LEUKOCYTE ADHESION DEFICIENCY, TYPE I | LAD |
| RHESUS BLOOD GROUP, CcEe ANTIGENS | RHCE |
| FACTOR V DEFICIENCY | |
| NEURITE OUTGROWTH INHIBITOR | |
| GOGLI AUTOANTIGEN, GOLGIN SUBFAMILY A, 4 | GOLGA4 |
| ADENOSINE DEAMINASE | ADA |
| INTERFERON, GAMMA, RECEPTOR 1 | IFNGR1 |
| THROMBASTHENIA OF GLANZMANN AND NAEGELI | |
| CHEDIAK-HIGASHI SYNDROME | CHS1 |
| ANTITHROMBIN III DEFICIENCY | |
| V-HA-RAS HARVEY RAT SARCOMA VIRAL ONCOGENE HOMOLOG | HRAS |
| INTEGRIN, BETA-2 | ITGB2 |
| PHOSPHODIESTERASE I/NUCLEOTIDE PYROPHOSPHATASE 1 | PDNP1 |
| TUMOR NECROSIS FACTOR RECEPTOR SUPERFAMILY, MEMBER 6 | TNFSRSF6 |
| DIABETES INSIPIDUS, NEPHROGENIC, X-LINKED | |
| CD59 ANTIGEN P18-20 | CD59 |
| T-CELL ANTIGEN RECEPTOR, ALPHA SUBUNIT | TCRA |

TABLE 6

Surface Antigens of Human Chromosome 5

| Long Name | Abbreviation |
| --- | --- |
| HEMOGLOBIN--BETA LOCUS | HBB |
| HEMOPHILIA A | |
| MUSCULAR DYSTROPHY, PSEUDOHYPERTROPHIC PROGRESSIVE, DUCHENNE AND BECKER TYPES | |
| IMMUNODEFICIENCY WITH HYPER-IgM | |
| ATAXIA-TELANGIECTASIA | AT |
| RETINOBLASTOMA | RB1 |
| CYSTIC FIBROSIS TRANSMEMBRANE CONDUCTANCE REGULATOR | CFTR |
| HEMOCHROMATOSIS | HFE |
| INTEGRIN, ALPHA-2 | ITGA2 |
| WILMS TUMOR 1 | WT1 |
| MONOCYTE DIFFERENTIATION ANTIGEN CD 14 | CD14 |
| TUMOR PROTEIN p53 | TP53 |
| SURFACE ANTIGEN 5 | S5 |
| ALZHEIMER DISEASE | AD |

TABLE 6-continued

Surface Antigens of Human Chromosome 5

| Long Name | Abbreviation |
| --- | --- |
| LEUKOCYTE ANTIGEN GROUP FIVE | LAG5 |
| BRUTON AGAMMAGLOBULINEMIA TYROSINE KINASE | BTK |
| ADENOSINE DEAMINASE | ADA |
| ANTIGEN MSK39 IDENTIFIED BY MONOCLONAL ANTIBODY 5.1H11 | MSK39 |
| TUMOR NECROSIS FACTOR RECEPTOR SUPERFAMILY, MEMBER 5 | TNFRSF5 |
| LYMPHOCYTE ANTIGEN 64, RADIOPROTECTIVE, 105-KD | LY64 |
| WISKOTT-ALDRICH SYNDROME | WAS |
| VON WILLEBRAND DISEASE | |
| RHESUS BLOOD GROUP CcEe ANTIGENS | RHCE |
| SOLUTE CARRIER FAMILY 7, MEMBER 5 | SLC7A5 |
| MAJOR HISTOCOMPATIBILITY COMPLEX, CLASS I, A | HLA-A |
| PHOSPHODIESTERASE I/NUCLEOTIDE PYROPHOSPHATASE 1 | PDNP1 |
| T-LYMPHOCYTE SURFACE CD2 ANTIGEN | CD2 |
| CHEDIAK-HIGASHI SYNDROME | CHS1 |
| INTEGRIN, BETA-3 | ITGB3 |
| PROTEIN-TYROSINE PHOSPHATASE, RECEPTOR-TYPE, C | PTPRC |
| SEVERE COMBINED IMMUNODEFICIENCY, X-LINKED | SCIDX1 |
| V-HA-RAS HARVEY RAT SARCOMA VIRAL ONCOGENE HOMOLOG | HRAS |
| SOLUTE CARRIER FAMILY 3, MEMBER 2 | SLC3A2 |
| FLOTILLIN 2 | FLOT2 |
| THROMBASTHENIA OF GLANZMANN AND NAEGELI | |
| BLOOD GROUP--MN LOCUS | MN |
| BULLOUS PEMPHIGOID ANTIGEN 1 | BPAG1 |
| TUMOR NECROSIS FACTOR RECEPTOR SUPERFAMILY, MEMBER 6 | TNFRSF6 |
| KILLER CELL IMMUNOGLOBULIN-LIKE RECEPTOR, TWO DOMAINS, SHORT CYTOPLASMIC TAIL, 2 | KIR2DS2 |
| MEMBRANE COMPONENT, CHROMOSOME 17, SURFACE MARKER 2 | M17S2 |
| TYROSINE HYDROXYLASE | TH |
| FACTOR V DEFICIENCY | |
| L1 CELL ADHESION MOLECULE | L1CAM |
| LEUKOCYTE ADHESION DEFICIENCY, TYPE I | LAD |
| SOLUTE CARRIER FAMILY 4, ANION EXCHANGER, MEMBER 1 | SLC4A1 |
| INTERCELLULAR ADHESION MOLECULE 1 | ICAM1 |
| HYPOPHOSPHATEMIA, X-LINKED | |
| DIABETES INSIPIDUS, NEPHROGENIC, X-LINKED | |
| ANTITHROMBIN III DEFICIENCY | |
| BLOOD GROUP--LUTHERAN SYSTEM | LU |

TABLE 7

Surface Antigens of Human Chromosome 6

| Long Name | Abbreviation |
| --- | --- |
| PHOSPHODIESTERASE I/NUCLEOTIDE PYROPHOSPHATASE 1 | PDNP1 |
| MAJOR HISTOCOMPATIBILITY COMPLEX, CLASS I, A | HLA-A |
| HEMOCHROMATOSIS | HFE |
| HEMOPHILIA A | |
| MEMBRANE COMPONENT, CHROMOSOME 6, POLYPEPTIDE 2 | M6P2 |
| HEMOGLOBIN--BETA LOCUS | HBB |
| TUMOR NECROSIS FACTOR RECEPTOR SUPERFAMILY, MEMBER 6 | TNFRSF6 |
| KANGAI 1 | DAII1 |
| MUSCULAR DYSTROPHY, PSEUDOHYPERTROPHIC PROGRESSIVE, DUCHENNE AND BECKER TYPES | |
| INTERFERON, GAMMA, RECEPTOR 1 | IFNGR1 |
| SURFACE ANTIGEN 6 | S6 |
| INSULIN-LIKE GROWTH FACTOR 2 RECEPTOR | IGF2R |
| BULLOUS PEMPHIGOID ANTIGEN 1 | BPAG1 |
| ATAXIA-TELANGIECTASIA | AT |
| CD59 ANTIGEN P18-20 | CD59 |
| CD83 ANTIGEN | CD83 |
| ATP-BINDING CASSETTE, SUBFAMILY B, MEMBER 2 | ABCB2 |
| RETINOBLASTOMA | RB1 |
| CD24 ANTIGEN | CD24 |
| CYSTIC FIBROSIS TRANSMEMBRANE CONDUCTANCE REGULATOR | CFTR |
| WILMS TUMOR 1 | WT1 |
| SIGNAL TRANSDUCER AND ACTIVATOR OF TRANSCRIPTION 6 | STAT6 |
| TUMOR PROTEIN p53 | TP53 |
| RH-NULL, REGULATOR TYPE | RHN |
| TUMOR NECROSIS FACTOR LIGAND SUPERFAMILY, MEMBER 6 | TNFSF6 |
| RHESUS BLOOD GROUP-ASSOCIATED GLYCOPROTEIN | RHAG |
| WISKOTT-ALDRICH SYNDROME | WAS |

TABLE 7-continued

Surface Antigens of Human Chromosome 6

| Long Name | Abbreviation |
|---|---|
| LYMPHOCYTE ANTIGEN 6 COMPLEX, LOCUS E | LY6E |
| ALZHEIMER DISEASE | AD |
| INTEGRIN, BETA-3 | ITGB3 |
| TAP-BINDING PROTEIN | TAPP |
| LYMPHOCYTE ANTIGEN 6 COMPLEX, LOCUS H | LY6H |
| ADENOSINE DEAMINASE | ADA |
| SIALYLTRANSFERASE 1 | SIAT1 |
| VON WILLEBRAND DISEASE | |
| SEVERE COMBINED IMMUNODEFICIENCY, X-LINKED | SCIDX1 |
| THROMBASTHENIA OF GLANZMANN AND NAEGELI | |
| IMMUNODEFICIENCY WITH HYPER-IgM | |
| SOLUTE CARRIER FAMILY 4, ANION EXCHANGER, MEMBER 1 | SLC4A1 |
| BRUTON AGAMMAGLOBULINEMIA TYROSINE KINASE | BTK |
| RHESUS BLOOD GROUP, CcEe | RHCE |
| FACTOR V DEFICIENCY | |
| CD9 ANTIGEN | CD9 |
| ANTITHROMBIN III DEFICIENCY | |
| INTEGRIN, BETA-2 | ITGB2 |
| TROPHOBLAST GLYCOPROTEIN | TPBG, M6P1 |
| DIABETES INSIPIDUS, NEPHROGENIC, X-LINKED | |
| LEUKOCYTE ADHESION DEFICIENCY, TYPE I | LAD |
| V-ERB-B2 AVIAN ERYTHROBLASTIC LEUKEMIA VIRAL ONCOGENE HOMOLOG 2 | ERBB2 |
| L1 CELL ADHESION MOLECULE | L1CAM |

TABLE 8

Surface Antigens of Human Chromosome 7

| Long Name | Abbreviation |
|---|---|
| CYSTIC FIBROSIS TRANSMEMBRANE CONDUCTANCE REGULATOR | CFTR |
| EPIDERMAL GROWTH FACTOR RECEPTOR | EGFR |
| HEMOPHILIA A | |
| HEMOGLOBIN--BETA LOCUS | HBB |
| T-CELL ANTIGEN RECEPTOR, GAMMA SUBUNIT | TCRG |
| HEPATOCELLULAR CARCINOMA | |
| CD36 ANTIGEN | CD36 |
| RETINOBLASTOMA | RB1 |
| ATAXIA-TELANGIECTASIA | AT |
| MUSCULAR DYSTROPHY, PSEUDOHYPERTROPHIC PROGRESSIVE, DUCHENNE AND BECKER TYPES | |
| BLOOD GROUP-KELL-CELLANO SYSTEM | KEL |
| HEMOCHROMATOSIS | HFE |
| TUMOR PROTEIN p53 | TP53 |
| WILMS TUMOR 1 | WT1 |
| ALZHEIMER DISEASE | AD |
| HOMEO BOX GENE HB9 | HLXB9 |
| AMPHIPHYSIN | AMPH |
| SIX-TRANSMEMBRANE EPITHELIAL ANTIGEN OF THE PROSTATE | STEAP |
| SOLUTE CARRIER FAMILY 7, MEMBER 5 | SLC7A5 |
| WISKOTT-ALDRICH SYNDROME | WAS |
| ADENOSINE DEAMINASE | ADA |
| VON WILLEBRAND DISEASE | |
| PHOSPHODIESTERASE I/NUCLEOTIDE PYROPHOSPHATASE 1 | PDNP1 |
| FACTOR DEFICIENCY | |
| RHESUS BLOOD GROUP, CcEe ANTIGENS | RHCE |
| MAJOR HISTOCOMPATIBILITY COMPLEX, CLASS I, A | HLA-A |
| LEUKOCYTE ADHESION DEFICIENCY, TYPE 1 | LAD |
| SOLUTE CARRIER FAMILY 4, ANION EXCHANGER, MEMBER 1 | SLC4A1 |
| SURFACE ANTIGEN 6 | S6 |
| LETHAL ANTIGEN--ALL-A1 | |
| BRUTON AGAMMAGLOBULINEMIA TYROSINE KINASE | BTK |
| V-HA-RAS HARVEY RAT SARCOMA VIRAL ONCOGENE HOMOLOG | HRAS |
| INTERLEUKIN 2 RECEPTOR, GAMMA | IL2RG |
| CHEDIAK-HIGASHI SYNDROME | CHS1 |
| SEVERE COMBINED IMMUNODEFICIENCY, X-LINKED | SCIDX1 |
| DIABETES INSIPIDUS, NEPHROGENIC, X-LINKED | |
| IMMUNODEFICIENCY WITH HYPER-IgM | |
| TYROSINE HYDROXYLASE | TH |

TABLE 8-continued

Surface Antigens of Human Chromosome 7

| Long Name | Abbreviation |
|---|---|
| V-ERB-B2 AVIAN ERYTHROBLASTIC LEUKEMIA VIRAL ONCOGENE HOMOLOG 2 | ERBB2 |
| ANTITHROMBIN III DEFICIENCY | |
| L1 CELL ADHESION MOLECULE | L1CAM |
| MEMBRANE COMPONENT, CHROMOSOME 1, SURFACE MARKER 1 | M1S1 |
| INTERLEUKIN 4 RECEPTOR | IL4R |
| TUMOR NECROSIS FACTOR RECEPTOR SUPERFAMILY, MEMBER 6 | TNFRSF6 |
| MEMBRANE-SPANNING 4 DOMAINS, SUBFAMILY A, MEMBER 1 | MS4A1 |
| INTERFERON, GAMMA, RECEPTOR 1 | IFNGR1 |
| LUPUS ERYTHEMATOSUS, SYSTEMIC | SLE |
| INTERCELLULAR ADHESION MOLECULE 1 | ICAM1 |
| INTEGRIN, ALPHA-E | ITGAE |
| AGGRECAN 1 | AGC1 |

TABLE 9

Surface Antigens of Human Chromosome 8

| Long Name | Abbreviation |
|---|---|
| HEMOPHILIA A | |
| HEMOGLOBIN--BETA LOCUS | HBB |
| PLASMINOGEN ACTIVATOR, TISSUE | PLAT |
| ATAXIA-TELANGIECTASIA | AT |
| HEPATOCELLULAR CARCINOMA | |
| WILMS TUMOR 1 | WT1 |
| MUSCULAR DYSTROPHY, PSEUDOHYPERTROPHIC PROGRESSIVE, DUCHENNE AND BECKER TYPES | |
| CYSTIC FIBROSIS TRANSMEMBRANE CONDUCTANCE REGULATOR | CFTR |
| RETINOBLASTOMA | RB1 |
| HEMOCHROMATOSIS | HFE |
| A DISINTEGRIN AND METALLOPROTEINASE DOMAIN 8 | ADAM8 |
| TUMOR PROTEIN p53 | TP53 |
| LYMPHOCYTE ANTIGEN 6 COMPLEX, LOCUS E | LY6E |
| ALZHEIMER DISEASE | AD |
| SURFACE ANTIGEN 8 | S8 |
| INTEGRIN, BETA-3 | ITGB3 |
| WISKOTT-ALDRICH SYNDROME | WAS |
| BRUTON AGAMMAGLOBULINEMIA TYROSINE KINASE | BTK |
| VON WILLEBRAND DISEASE | |
| LYMPHOCYTE ANTIGEN 6 COMPLEX, LOCUS H | LY6H |
| MAJOR HISTOCOMPATIBILITY COMPLEX, CLASS I, A | HLA-A |
| FACTOR V DEFICIENCY | |
| T-CELL ANTIGEN RECEPTOR, ALPHA SUBUNIT | TCRA |
| ADENOSINE DEAMINASE | ADA |
| THROMBASTHENIA OF GLANZMANN AND NAEGELI | |
| TUMOR NECROSIS FACTOR LIGAND SUPERFAMILY, MEMBER 8 | TNFSF8 |
| CD59 ANTIGEN P18-20 | CD59 |
| RHESUS BLOOD GROUP, CcEe ANTIGENS | RHCE |
| SOLUTE CARRIER FAMILY 4, ANION EXCHANGER, MEMBER 1 | SLCA4A1 |
| TUMOR NECROSIS FACTOR RECEPTOR SUPERFAMILY, MEMBER 6, | TNFRSF6 |
| DIABETES INSIPIDUS, NEPHROGENIC, X-LINKED | |
| IMMUNODEFICIENCY WITH HYPER-IgM | |
| V-ERB-B2 AVIAN ERYTHROBLASTIC LEUKEMIA VIRAL ONCOGENE HOMOLOG 2 | ERBB2 |
| CD44 ANTIGEN | CD44 |
| L1 CELL ADHESION MOLECULE | L1CAM |
| ANTITHROMBIN III DEFICIENCY | |
| SOLUTE CARRIER FAMILY 3, MEMBER 2 | SLC3A2 |
| INTEGRIN, BETA-2 | ITGB2 |
| PHOSPHODIESTERASE I/NUCLEOTIDE PYROPHOSPHATASE 1 | PDNP1 |
| INTERFERON, GAMMA, RECEPTOR 1 | IFNGR1 |
| CD8 ANTIGEN, ALPHA POLYPEPTIDE | CD8A |
| SURFACE ANTIGEN MIC2 | MIC2 |
| THYMOCYTE ANTIGEN CD1A | CD1A |
| LETHAL ANTIGEN--A1 | ALL-A1 |
| TYROSINE HYDROXYLASE | TH |
| CD9 ANTIGEN | CD9 |
| DIPEPTIDYLPEPTIDASE IV | DPP4 |
| BETA-2 MICROGLOBULIN | B2M |
| XG BLOOD GROUP SYSTEM | XG; PBDX |
| LUPUS ERYTHEMATOSUS, SYSTEMIC | SLE |

TABLE 10

Surface Antigens of Human Chromosome 9

| Long Name | Abbreviation |
|---|---|
| T-LYMPHOCYTE SURFACE sLY-9 | LY9 |
| HEMOPHILIA A | |
| WILMS TUMOR 1 | WT1 |
| HEMOGLOBIN-BETA LOCUS | HBB |
| ATAXIA-TELANGIECTASIA | AT |
| CYSTIC FIBROSIS TRANSMEMBRANE CONDUCTANCE REGULATOR | CFTR |
| MUSCULAR DYSTROPHY, PSEUDOHYPERTROPHIC PROGRESSIVE, DUCHENNE AND BECKER TYPES | |
| RETINOBLASTOMA | RB1 |
| ALZHEIMER DISEASE | AD |
| HEMOCHROMATOSIS | HFE |
| TUMOR PROTEIN p53 | TP53 |
| PHOSPHODIESTERASE I/NUCLEOTIDE PYROPHOSPHATASE 1 | PDNP1 |
| INTEGRIN, BETA-3 | ITGB3 |
| VON WILLEBRAND DISEASE | |
| THROMBASTHENIA OF GLANZMANN AND NAEGELI | |
| ADENOSINE DEAMINASE | ADA |
| CD59 ANTIGEN P18-20 | CD59 |
| WISKOTT-ALDRICH SYNDROME | WAS |
| TUMOR NECROSIS FACTOR LIGAND SUPERFAMILY, MEMBER 8 | TNFSF8 |
| MEMBRANE COMPONENT, CHROMOSOME 4, SURFACE MARKER 1 | M4S1 |
| IMMUNODEFICIENCY WITH HYPER-IgM | |
| BRUTON AGAMMAGLOBULINEMIA TYROSINE KINASE | BTK |
| INTERFERON, GAMMA, RECEPTOR 1 | IFNGR1 |
| FACTOR V DEFICIENCY | |
| MAJOR HISTOCOMPATIBILITY COMPLEX, CLASS I, A | HLA-A |
| SOLUTE CARRIER FAMILY 4, ANION EXCHANGER, MEMBER 1 | SLC4A1 |
| SEVERE COMBINED IMMUNODEFICIENCY, X-LINKED | SCIDX1 |
| T-CELL ANTIGEN RECEPTOR, GAMMA SUBUNIT | TCRG |
| MEMBRANE COMPONENT, CHROMOSOME 1, SURFACE MARKER 1 | M1S1 |
| DIABETES INSIPIDUS, NEPHROGENIC, X-LINKED | |
| CHEDIAK-HIGASHI SYNDROME | CHS1 |
| THY-1 T-CELL ANTIGEN | THY1 |
| T-LYMPHOCYTE SURFACE CD2 ANTIGEN | CD2 |
| INTERCELLULAR ADHESION MOLECULE 1 | ICAM1 |
| TUMOR NECROSIS FACTOR RECEPTOR SUPERFAMILY, MEMBER 6 | TNFRSF6 |
| SOLUTE CARRIER FAMILY 3, MEMBER 2 | SLC3A2 |
| CD9 ANTIGEN | CD9 |
| INTERLEUKIN 2 RECEPTOR, ALPHA | IL2RA |
| XG BLOOD GROUP SYSTEM | XG; PBDX |
| LUPUS ERYTHEMATOSUS, SYSTEMIC | SLE |
| INTERLEUKIN 2 RECEPTOR, GAMMA | IL2RG |
| DIPEPTIDYLPEPTIDASE IV | DPP4 |
| TRANSFERRIN RECEPTOR | TFRC |
| V-ERB-B2 AVIAN ERYTHROBLASTIC LEUKEMIA VIRAL ONCOGENE HOMOLOG 2 | ERBB2 |
| BULLOUS PEMPHIGOID ANTIGEN 1 | BPAG1 |
| TRANSFERRIN | TF |
| ANTITHROMBIN III DEFICIENCY | |
| V-HA-RAS HARVEY RAT SARCOMA VIRAL ONCOGENE HOMOLOG | HRAS |
| L1 CELL ADHESION MOLECULE | L1CAM |
| HYPOPHOSPHATEMIA, X-LINKED | |

TABLE 11

Surface Antigens of Human Chromosome 10

| Long Name | Abbreviation |
|---|---|
| HEMOPHILIA A | A |
| TUMOR NECROSIS FACTOR RECEPTOR SUPERFAMILY, MEMBER 6 | TNFRSF6 |
| INTERLEUKIN 2 RECEPTOR, ALPHA | IL2RA |
| INTEGRIN, BETA-1 | RB1 |
| RETINOBLASTOMA | RB1 |
| HEMOGLOBIN-BETA LOCUS | HBB |
| MUSCULAR DYSTROPHY, PSEUDOHYPERTROPHIC PROGRESSIVE, DUCHENNE AND BECKER TYPES | |
| CYSTIC FIBROSIS TRANSMEMBRANE CONDUCTANCE REGULATOR | CFTR |
| ATAXIA-TELANGIECTASIA | AT |
| HEMOCHROMATOSIS | HFE |
| WILMS TUMOR 1 | WT1 |
| A DISINTEGRIN AND METALLOPROTEINASE DOMAIN 8 | ADAM8 |
| CD39 ANTIGEN | CD39 |
| TUMOR PROTEIN p53 | TP53 |
| WISKOTT-ALDRICH SYNDROME | WAS |
| ALZHEIMER DISEASE | AD |
| ANTIGEN DEFINED BY MONOCLONAL ANTIBODY TRA-2-10 | MIC10 |
| INTERFERON, GAMMA, RECEPTOR 1 | IFNGR1 |

TABLE 11-continued

Surface Antigens of Human Chromosome 10

| Long Name | Abbreviation |
|---|---|
| PHOSPHODIESTERASE I/NUCLEOTIDE PYROPHOSPHATASE 1 | PDNP1 |
| NEUROPILIN 1 | NRP1 |
| ADENOSINE DEAMINASE | ADA |
| SOLUTE CARRIER FAMILY 4, ANION EXCHANGER, MEMBER 1 | SLC4A1 |
| T-CELL ANTIGEN RECEPTOR, ALPHA SUBUNIT | TCRA |
| DIABETES INSIPIDUS, NEPHROGENIC, X-LINKED | |
| VON WILLEBRAND DISEASE | |
| MAJOR HISTOCOMPATIBILITY COMPLEX, CLASS I, A ANTITHROMBIN III DEFICIENCY | HLA-A |
| IMMUNODEFICIENCY WITH HYPER-IgM | |
| FACTOR V DEFICIENCY | |
| INTEGRIN, BETA-3 | ITGB3 |
| RHESUS BLOOD GROUP, CcEe ANTIGENS | RHCE |
| THY-1 T-CELL ANTIGEN | THY1 |
| CD44 ANTIGEN | CD44 |
| V-HA-RAS HARVEY RAT SARCOMA VIRAL ONCOGENE HOMOLOG | HRAS |
| PLASMINOGEN ACTIVATOR, TISSUE | PLAT |
| CD59 ANTIGEN P18-20 | CD59 |
| T-CELL ANTIGEN RECEPTOR, DELTA SUBUNIT | TCRD |
| BRUTON AGAMMAGLOBULINEMIA TYROSINE KINASE | BTK |
| SEVERE COMBINED IMMUNODEFICIENCY, X-LINKED | SCIDX1 |
| T-CELL ANTIGEN RECEPTOR, GAMMA SUBUNIT | TCRG |
| SOLUTE CARRIER FAMILY 3, MEMBER 2 | SLC3A2 |
| INTEGRIN, BETA-2 | ITGB2 |
| EPIDERMAL GROWTH FACTOR RECEPTOR | EGFR |
| MEMBRANE COMPONENT, CHROMOSOME 1, SURFACE MARKER 1 | M1SI |
| LEUKOCYTE ADHESION DEFICIENCY, TYPE 1 | LAD |
| XG BLOOD GROUP SYSTEM | SG; PBDX |
| THYMOCYTE ANTIGEN CD1A | CD1A |
| INTERCELLULAR ADHESION MOLECULE 1 | ICAM1 |
| CD36 ANTIGEN | CD36 |
| SURFACE ANTIGEN | MIC2 |

TABLE 12

Surface Antigens of Human Chromosome 11

| Long Name | Abbreviation |
|---|---|
| WILMS TUMOR 1 | WT1 |
| HEMOGLOBIN-BETA LOCUS | HBB |
| ATAXIA-TELANGIECTASIA | AT |
| LETHAL ANTIGEN-A1 | AL-A1 |
| CD59 ANTIGEN P18-20 | CD59 |
| THY-1 T-CELL ANTIGEN | THY1 |
| CD44 ANTIGEN | CD44 |
| SOLUTE CARRIER FAMILY 3, MEMBER 2 | SLC3A2 |
| V-HA-RAS HARVEY RAT SARCOMA VIRAL ONCOGENE HOMOLOG | HRAS |
| FUCOSYLTRANSFERASE 4 | FUT4 |
| KANGAI 1 | KAI1 |
| HEMOPHILIA A | |
| MEMBRANE-SPANNING 4 DOMAINS, SUBFAMILY A, MEMBER 2 | MS4A2 |
| LYMPHOCYTE ANTIGEN CD5 | CD5 |
| TYROSINE HYDROXYLASE | TH |
| HEPATOCELLULAR CARCINOMA | |
| MUSCULAR DYSTROPHY, PSEUDOHYPERTROPHIC PROGRESSIVE, DUCHENNE AND BECKER TYPES | |
| MEMBRANE-SPANNING 4 DOMAINS, SUBFAMILY A, MEMBER 1 | MS4A1 |
| CYSTIC FIBROSIS TRANSMEMBRANE CONDUCTANCE REGULATOR | CFTR |
| RETINOBLASTOMA | RB1 |
| CD151 ANTIGEN | CD151 |

TABLE 12-continued

Surface Antigens of Human Chromosome 11

| Long Name | Abbreviation |
|---|---|
| ANTIGEN MSK39 IDENTIFIED BY MONOCLONAL ANTIBODY 5.1H11 | MSK39 |
| HEMOCHROMATOSIS | HFE |
| INTEGRIN, BETA-3 | IGB3 |
| RED BLOOD CELL ANTIGEN MER 2 | MER2 |
| TUMOR PROTEIN p53 | TP53 |
| VON WILLEBRAND DISEASE | |
| PHOSPHODIESTERASE I/NUCLEOTIDE PYROPHOSPHATASE 1 | PDNP1 |
| WISKOTT-ALDRICH SYNDROME | WAS |
| ADENOSINE DEAMINASE | ADA |
| BRUTON AGAMMAGLOBULINEMIA TYROSINE KINASE | BTK |
| T-CELL ANTIGEN RECEPTOR, ALPHA SUBUNIT | TCRA |
| ALZHEIMER DISEASE | AD |
| MAJOR HISTOCOMPATIBILITY COMPLEX, CLASS I, AA | HLA-A |
| FLOTILLIN 2 | FLOT2 |
| ANTIGEN DEFINED BY MONOCLONAL ANTIBODY F10.44.2 | |
| SOLUTE CARRIER FAMILY 4, ANION EXCHANGER, MEMBER 1 | SLC4A1 |
| THROMBASTHENIA OF GLANZMANN AND NAEGELI | |
| INTERCELLULAR ADHESION MOLECULE 1 | ICAM1 |
| SURFACE ANTIGEN, GLYCOPROTEIN 75 | |
| EPIDERMAL GROWTH FACTOR RECEPTOR | EGFR |
| LEUKOCYTE ADHESION DEFICIENCY, TYPE I | LAD |
| DIABETES INSIPIDUS, NEPHROGENIC, X-LINKED | |
| INTERFERON, GAMMA, RECEPTOR 1 | IFNGR1 |
| T-CELL ANTIGEN RECEPTOR, DELTA SUBUNIT | TCRD |
| INTEGRIN, BETA-2 | IGB2 |
| FACTOR V DEFICIENCY | |
| CD4 ANTIGEN | CD4 |
| TUMOR NECROSIS FACTOR RECEPTOR SUPERFAMILY, MEMBER 6 | TNFRSF6 |
| SURFACE ANTIGEN MIC2 | MIC2 |

TABLE 13

Surface Antigens of Human Chromosome 12

| Long Name | Abbreviation |
|---|---|
| VON WILLEBRAND DISEASE | |
| CD9 ANTIGEN | CD9 |
| CD4 ANTIGEN | CD4 |
| SURFACE ANTIGEN OF ACTIVATED B CELLS, BB1 | BB1 |
| HEMOPHILIA A | |
| CYSTIC FIBROSIS TRANSMEMBRANE CONDUCTANCE REGULATOR | CFTR |
| RETINOBLASTOMA | RB1 |
| MUSCULAR DYSTROPHY, PSEUDOHYPERTROPHIC PROGRESSIVE, DUCHENNE AND BECKER TYPES | |
| CD69 ANTIGEN | CD69 |
| SIGNAL TRANSDUCER AND ACTIVATOR OF TRANSCRIPTION 6 | STAT6 |
| COMPLEMENT COMPONENT C1r DEFICIENCY | |
| TUMOR REJECTION ANTIGEN 1 | TRA1 |
| ATAXIA-TELANGIECTASIA | AT |
| WISKOTT-ALDRICH SYNDROME | WAS |
| WILMS TUMOR | WT1 |
| V-HA-RAS HARVEY RAT SARCOMA VIRAL ONCOGENE HOMOLOG | HRAS |
| HEMOGLOBIN-BETA LOCUS | HBB |
| ALZHEIMER DISEASE | AD |
| TUMOR PROTEIN p53 | TP53 |
| TYRO PROTEIN TYROSINE KINASE-BINDING PROTEIN | TYROBP |
| BRUTON AGAMMAGLOBULINEMIA TYROSINE KINASE | BTK |
| INTEGRIN, BETA-2 | ITGB2 |

TABLE 13-continued
Surface Antigens of Human Chromosome 12

| Long Name | Abbreviation |
|---|---|
| HEMOCHROMATOSIS | HFE |
| FLOTILLIN 2 | FLOT2 |
| INTEGRIN, BETA-3 | ITGB3 |
| INTERFERON, GAMMA, RECEPTOR 1 | INFNGR1 |
| CD44 ANTIGEN | CD44 |
| THY-1 T-CELL ANTIGEN | THY1 |
| CENTROMERIC PROTEIN C1 | CENPC1 |
| ADENOSINE DEAMINASE | ADA |
| DIABETES INSIPIDUS, NEPHROGENIC, X-LINKED | |
| THROMBASTHENIA OF GLANZMANN AND NAEGELI | |
| T-CELL ANTIGEN RECEPTOR, ALPHA SUBUNIT | TCRA |
| SOLUTE CARRIER FAMILY 4, ANION EXCHANGER, MEMBER 1 | SLC4A1 |
| BLOOD GROUP-LUTHERAN SYSTEM | LU |
| SURFACE ANTIGEN MIC2 | MIC2 |
| PHOSPHODIESTERASE 1/NUCLEOTIDE PYROPHOSPHATASE 1 | PDNP1 |
| LETHAL ANTIGEN-A1 | AL-A1 |
| XG BLOOD GROUP SYSTEM | XG; PBDX |
| ANTITHROMBIN III DEFICIENCY | |
| TUMOR NECROSIS FACTOR RECEPTOR SUPERFAMILY, MEMBER 6 | TNFRSF6 |
| HYPOPHOSPHATEMIA, X-LINKED | |
| FACTOR V DEFICIENCY | |
| MAJOR HISTOCOMPATIBILITY COMPLEX, CLASS I, A | HLA-A |
| CD59 ANTIGEN P18-20 | CD59 |
| SOLUTE CARRIER FAMILY 3, MEMBER 2 | SLC3A2 |
| CD36 ANTIGEN | CD36 |
| EPIDERMAL GROWTH FACTOR RECEPTOR | EGFR |
| IMMUNODEFICIENCY WITH HYPER-IgM | |

TABLE 14
Surface Antigens of Human Chromosome 13

| Long Name | Abbreviation |
|---|---|
| RETINOBLASTOMA | RB1 |
| MUSCULAR DYSTROPHY, PSEUDOHYPERTROPHIC PROGRESSIVE, DUCHENNE AND BECKER TYPES | |
| HEMOPHILIA A | |
| CYSTIC FIBROSIS TRANSMEMBRANE CONDUCTANCE REGULATOR | CFTR |
| HEMOGLOBIN-BETA LOCUS | HBB |
| BARE LYMPHOCYTE SYNDROME, TYPE 11 | |
| HEMOCHROMATOSIS | HFE |
| ATAXIA-TELANGIECTASIA | AT |
| ALZHEIMER DISEASE | AD |
| WISKOTT-ALDRICH SYNDROME | WAS |
| TUMOR PROTEIN p53 | TP53 |
| IMMUNODEFICIENCY WITH HYPERI-IgM | |
| WILMS TUMOR 1 | WT1 |
| INTEGRIN, BETA-3 | ITGB3 |
| CHEDIAK-HIGASHI SYNDROME | CHS1 |
| FACTOR V DEFICIENCY | |
| BRUTON AGAMMAGLOBULINEMIA TYROSINE KINASE | BTK |
| THROMBASTHENIA OF GLANZMANN AND NAEGELI | |
| TUMOR NECROSIS FACTOR RECEPTOR SUPERFAMILY, MEMBER 6 | TNFRSF6 |
| CD59 ANTIGEN P18-20 | CD59 |
| BLOOD GROUP-LUTHERAN SYSTEM | LU |
| INTEGRIN, BETA-2 | ITGB2 |
| BLOOD GROUP-MN LOCUS | MN |
| ADENOSINE DEAMINASE | ADA |
| SEVERE COMBINED IMMUNODEFICIENCY, X-LINKED | SCIDX1 |
| INTERLEUKIN 2 RECEPTOR, GAMMA | IL2RG |
| VON WILLEBRAND DISEASE | |

TABLE 14-continued
Surface Antigens of Human Chromosome 13

| Long Name | Abbreviation |
|---|---|
| SOLUTE CARRIER FAMILY 3, MEMBER 2 | SLC3A2 |
| THY-1 T-CELL ANTIGEN | THY1 |
| PHOSPHODIESTERASE I/NUCLEOTIDE PYROPHOSPHATASE 1 | PDNP1 |
| THYMOCYTE ANTIGEN CD1A | CD1A |
| LUPUS ERYTHEMATOSUS, SYSTEMIC | SLE |
| LETHAL ANTIGEN- A1 | AL-A1 |
| MAJOR HISTOCOMPATIBILITY COMPLEX, CLASS I, A | HLA-A |
| SOLUTE CARRIER FAMILY 4, ANION EXCHANGER, MEMBER 1 | SLC4A1 |
| RHESUS BLOOD GROUP, CcEe ANTIGENS | RHCE |
| V-HA-RAS HARVEY RAT SARCOMA VIRAL ONCOGENE HOMOLOG | HRAS |
| T-CELL ANTIGEN RECEPTOR, ALPHA SUBUNIT | TCRA |
| HISTOCOMPATIBILITY Y ANTIGEN | HY |
| SURFACE ANTIGEN MIC2 | MIC2 |
| CD44 ANTIGEN | CD44 |
| T-CELL ANTIGEN RECEPTOR, GAMMA SUBUNIT | TCRG |
| INTERCELLULAR ADHESION MOLECULE 1 | ICAM1 |
| ANTITHROMBIN III DEFICIENCY | |
| LEUKOCYTE ADHESION DEFICIENCY, TYPE I | LAD |
| CD ANTIGEN | CD |
| V-ERB-B2 AVIAN ERYTHROBLASTIC LEUKEMIA VIRAL ONCOGENE HOMOLOG 2 | ERBB2 |
| SOLUTE CARRIER FAMILY 3, MEMBER 1 | SLC3A1 |
| INTERLEUKIN 4 RECEPTOR | IL4R |
| TYROSINE HYDROXYLASE | TH |

TABLE 15
Surface Antigens of Human Chromosome 14

| Long Name | Abbreviation |
|---|---|
| T-CELL ANTIGEN RECEPTOR, ALPHA SUBUNIT | TCRA |
| ATAXIA-TELANGIECTASIA | AT |
| HEMOPHILIA A | |
| T-CELL ANTIGEN RECEPTOR, DELTA SUBUNIT | TCRD |
| HEMOGLOBIN-BETA LOCUS | HBB |
| MUSCULAR DYSTROPHY, PSEUDOHYPERTROPHIC PROGRESSIVE, DUCHENNE AND BECKER TYPES | |
| RETINOBLASTOMA | RB1 |
| BRUTON AGAMMAGLOBULINEMIA TYROSINE KINASE | BTK |
| ALZHEIMER DISEASE | AD |
| CYSTIC FIBROSIS TRANSMEMBRANE CONDUCTANCE REGULATOR | CFTR |
| WISKOTT-ALDRICH SYNDROME | WAS |
| HEMOCHROMATOSIS | HFE |
| BONE MARROW STROMAL CELL ANTIGEN | BST1 |
| WILMS TUMOR 1 | WT1 |
| TUMOR PROTEIN p53 | TP53 |
| T-CELL ANTIGEN RECEPTOR, GAMMA SUBUNIT | TCRG |
| VON WILLEBRAND DISEASE | |
| FACTOR V DEFICIENCY | |
| INTEGRIN, BETA-2 | ITGB2 |
| MAJOR HISTOCOMPATIBILITY COMPLEX, CLASS I, A | HLA-A |
| ADENOSINE DEAMINASE | ADA |
| CD8 ANTIGEN, ALPHA POLYPEPTIDE | CD8A |
| LEUKOCYTE ADHESION DEFICIENCY, TYPE I | LAD |
| V-ERB-B2 AVIAN ERYTHROBLASTIC LEUKEMIA VIRAL ONCOGENE HOMOLOG 2 | ERBB2 |
| INTEGRIN, BETA-3 | ITGB3 |
| SOLUTE CARRIER FAMILY 4, ANION EXCHANGER, MEMBER 1 | SLC4A1 |
| MEMBRANE-SPANNING 4 DOMAINS, SUBFAMILY A, MEMBER 2 | MS4A2 |
| INTERFERON, GAMMA, RECEPTOR 1 | IFNGR1 |
| INTERLEUKIN 2 RECEPTOR, ALPHA | IL2RA |
| LETHAL ANTIGEN-A1 | AL-A1 |

TABLE 15-continued

Surface Antigens of Human Chromosome 14

| Long Name | Abbreviation |
|---|---|
| SEVERE COMBINED IMMUNODEFICIENCY, X-LINKED | SCIDX1 |
| EPIDERMAL GROWTH FACTOR RECEPTOR | EGFR |
| CD59 ANTIGEN P18-20 | CD59 |
| LUPUS ERYTHEMATOSUS, SYSTEMIC | SLE |
| INTERCELLULAR ADHESION MOLECULE 1 | ICAM1 |
| SOLUTE CARRIER FAMILY 3, MEMBER 2 | SLC3A2 |
| CD44 ANTIGEN | CD44 |
| TYROSINE HYDROXYLASE | TH |
| IMMUNODEFICIENCY WITH HYPER-IgM | |
| L1 CELL ADHESION MOLECULE | L1CAM |
| DIPEPTIDYLPEPTIDASE IV | DPP4 |
| XG BLOOD GROUP SYSTEM | XG; PBDX |
| CD9 ANTIGEN | CD9 |
| INTERLEUKIN 2 RECEPTOR, GAMMA | IL2RG |
| TUMOR NECROSIS FACTOR RECEPTOR SUPERFAMILY, MEMBER 6 | TNFRSF6 |
| BLOOD GROUP-MN LOCUS | MN |
| V-HA-RAS HARVEY RAT SARCOMA VIRAL ONCOGENE HOMOLOG | HRAS |
| CD4 ANTIGEN | CD4 |
| RHESUS BLOOD GROUP, CcEe ANTIGENS | RHCE |
| BLOOD GROUP-KELL-CELLANO SYSTEM | KEL |

TABLE 16

Surface Antigens of Human Chromosome 15

| Long Name | Abbreviation |
|---|---|
| ALANYL AMINOPEPTIDASE | ANPEP |
| BETA-2-MICROGLOBULIN | B2M |
| HEMOGLOBIN-BETA LOCUS | HBB |
| HEMOPHILIA A | |
| RETINOBLASTOMA | RB1 |
| ATAXIA-TELANGIECTASIA | AT |
| CYSTIC FIBROSIS TRANSMEMBRANE CONDUCTANCE REGULATOR | CFTR |
| AGGRECAN 1 | AGC1 |
| MUSCULAR DYSTROPHY, PSEUDOHYPERTROPHIC PROGRESSIVE, DUCHENNE AND BECKER TYPES | |
| HEMOCHROMATOSIS | HFE |
| TUMOR PROTEIN p53 | TP53 |
| CD59 ANTIGEN P18-20 | CD59 |
| MAJOR HISTOCOMPATIBILITY COMPLEX, CLASS I, A | HLA-A |
| ALZHEIMER DISEASE | AD |
| WILMS TUMOR 1 | WT1 |
| BRUTON AGAMMAGLOBULINEMIA TYROSINE KINASE | BTK |
| V-ERB-B2 AVIAN ERYTHROBLASTIC LEUKEMIA VIRAL ONCOGENE HOMOLOG 2 | ERBB2 |
| INTERLEUKIN 15 | IL15 |
| ADENOSINE DEAMINASE | ADA |
| THROMBASTHENIA OF GLANZMANN AND NAEGELI | |
| CD44 ANTIGEN | CD44 |
| INTERCELLULAR ADHESION MOLECULE 1 | ICAM1 |
| T-CELL ANTIGEN RECEPTOR, ALPHA SUBUNIT | TCRA |
| WISKOTT-ALDRICH SYNDROME | WAS |
| IMMUNODEFICIENCY WITH HYPER IgM | |
| LEUKOCYTE ADHESION DEFICIENCY, TYPE I | LAD |
| SEVERE COMBINED IMMUNODEFICIENCY, X-LINKED | SCIDX1 |
| INTERLEUKIN 2 RECEPTOR, GAMMA | IL2RG |
| L1 CELL ADHESION MOLECULE | L1CAM |
| VON WILLEBRAND DISEASE | |
| INTEGRIN, BETA-2 | ITGB2 |
| BLOOD GROUP-MN LOCUS | MN |
| TRANSFERRIN | TF |
| LETHAL ANTIGEN-A1 | ALL-A1 |

TABLE 16-continued

Surface Antigens of Human Chromosome 15

| Long Name | Abbreviation |
|---|---|
| SOLUTE CARRIER FAMILY 4, ANION EXCHANGER, MEMBER 1 | SLC4-A1 |
| HYPOPHOSPHATEMIA, X-LINKED | |
| FACTOR V DEFICIENCY | |
| CENTROMERIC PROTEIN C1 | CENPC1 |
| RHESUS BLOOD GROUP, CcEe ANTIGENS | RHCE |
| T-CELL ANTIGEN RECEPTOR, DELTA SUBUNIT | TCRD |
| EPIDERMAL GROWTH FACTOR RECEPTOR | EGFR |
| LYMPHOCYTE ANTIGEN CD5 | CD5 |
| T-LYMPHOCYTE SURFACE CD ANTIGEN | CD2 |
| INTEGRIN, BETA-3 | ITGB3 |
| BLOOD GROUP-LUTHERAN SYSTEM | LU |
| ANTITHROMBIN III DEFICIENCY | |
| CD4 ANTIGEN | CD4 |
| CHEDIAK-HIGASHI SYNDROME | CHS1 |
| MEMBRANE COMPONENT, CHROMOSOME 6, POLYPEPTIDE 2 | M6P2 |
| T-CELL ANTIGEN RECEPTOR, GAMMA SUBUNIT | TCRG |

TABLE 17

Surface Antigens of Human Chromosome 16

| Long Name | Abbreviation |
|---|---|
| CD59 ANTIGEN -18-20 | CD59 |
| HEMOPHILIA A | |
| HEPATOCELLULAR CARCINOMA | |
| CD19 ANTIGEN | CD19 |
| MUSCULAR DYSTROPHY, PSEUDOHYPERTROPHIC PROGRESSIVE, DUCHENNE AND BECKER TYPES | |
| INTEGRIN, ALPHA-L | ITGAL |
| INTEGRIN, ALPHA-X | ITGAX |
| HEMOGLOBIN-BETA LOCUS | HBB |
| INTERLEUKIN 4 RECEPTOR | IL4R |
| SIALOPHORIN | SPN |
| ALZHEIMER DISEASE | AD |
| CYSTIC FIBROSIS TRANSMEMBRANE CONDUCTANCE REGULATOR | CFTR |
| BARE LYMPHOCYTE SYNDROME, TYPE II | |
| ATAXIA-TELANGIECTASIA | AT |
| INTEGRIN, ALPHA-M | ITGAM |
| HEMOCHROMATOSIS | HFE |
| INTERFERON-GAMMA-INDUCIBLE PROTEIN 16 | IFI16 |
| SOLUTE CARRIER FAMILY 7, MEMBER 5 | SLC7A5 |
| RETINOBLASTOMA | RB1 |
| WISKOTT-ALDRICH SYNDROME | WAS |
| BRUTON AGAMMAGLOBULINEMIA TYROSINE KINASE | BTK |
| TUMOR PROTEIN p53 | TP53 |
| WILMS TUMOR 1 | WT1 |
| TUMOR NECROSIS FACTOR RECEPTOR SUPERFAMILY, MEMBER 6 | TNFRSF6 |
| ADENOSINE DEAMINASE | ADA |
| ANTITHROMBIN III DEFICIENCY | |
| FACTOR V DEFICIENCY | |
| VON WILLEBRAND DISEASE | |
| T-CELL ANTIGEN RECEPTOR, GAMMA SUBUNIT | TCRG |
| SEVERE COMBINED IMMUNODEFICIENCY, X-LINKED | SCIDX1 |
| T-CELL ANTIGEN RECEPTOR, ALPHA SUBUNIT | TCRA |
| EPIDERMAL GROWTH FACTOR RECEPTOR | EGFR |
| LEUKOCYTE ADHESION DEFICIENCY, TYPE 1 | LAD |
| INTERFERON, GAMMA, RECEPTOR 1 | IFNGR1 |
| IMMUNODEFICIENCY WITH HYPER-IgM | |
| CD80 ANTIGEN | CD80 |
| LETHAL ANTIGEN-A1 | AL-A1 |
| SOLUTE CARRIER FAMILY 4, ANION EXCHANGER, MEMBER 1 | SLC4A1 |
| CD86 ANTIGEN | CD86 |
| ANTIGEN DEFINED BY MONOCLONAL ANTIBODY F10.44.2 | |

TABLE 17-continued

Surface Antigens of Human Chromosome 16

| Long Name | Abbreviation |
|---|---|
| INTERLEUKIN 2 RECEPTOR, ALPHA | IL2RA |
| CD4 ANTIGEN | CD4 |
| INTEGRIN, BETA-3 | ITGB3 |
| THY-1 T-CELL ANTIGEN | THY1 |
| PLASMINOGEN ACTIVATOR, TISSUE | PLAT |
| DIABETES INSIPIDUS, NEPHROGENIC, X-LINKED | |
| SURFACE ANTIGEN MIC2 | MIC2 |
| LUPUS ERYTHEMATOSUS, SYSTEMIC | SLE |
| CD44 ANTIGEN | CD44 |
| CHEDIAK-HIGASHI SYNDROME | CHS1 |

TABLE 18

Surface Antigens of Human Chromosome 17

| Long Name | Abbreviation |
|---|---|
| FLOTILLIN 2 | FLOT2 |
| MEMBRANE COMPONENT, CHROMOSOME 17, SURFACE MARKER 2 | M17S2 |
| ALZHEIMER DISEASE | AD |
| TUMOR PROTEIN p53 | TP53 |
| INTEGRIN, BETA-3 | ITGB3 |
| THROMBASTHENIA OF GLANZMANN AND NAEGELI | |
| V-ERB-B2 AVIAN ERYTHROBLASTIC LEUKEMIA VIRAL ONCOGENE HOMOLOG 2 | ERBB2 |
| HEMOPHILIA A | |
| SOLUTE CARRIER FAMILY 4, ANION EXCHANGER, MEMBER 1 | SLC4A1 |
| T-CELL ANTIGEN CD7 | CD7 |
| HEMOGLOBIN-BETA LOCUS | HBB |
| HUMAN T-CELL LEUKEMIA VIRUS RECEPTOR | HTLVR |
| SURFACE ANTIGEN 17 | SA17; S9 |
| MUSCULAR DYSTROPHY, PSEUDOHYPERTROPHIC PROGRESSIVE, DUCHENNE AND BECKER TYPES | |
| PLATELET-ENDOTHELIAL CELL ADHESION MOLECULE | PECAM1 |
| BLOOD GROUP SYSTEM SWANN | |
| RETINOBLASTOMA | RB1 |
| BLOOD GROUP SYSTEM FROESE | |
| HEMOCHROMATOSIS | HFE |
| ATAXIA-TELANGIECTASIA | AT |
| WILMS TUMOR 1 | WT1 |
| WISKOTT-ALDRICH SYNDROME | WAS |
| BRUTON AGAMMAGLOBULINEMIA TYROSINE KINASE | BTK |
| VON WILLEBRAND DISEASE | |
| ADENOSINE DEAMINASE | ADA |
| CYSTIC FIBROSIS TRANSMEMBRANE CONDUCTANCE REGULATOR | CFTR |
| MAJOR HISTOCOMPATABILITY COMPLEX, CLASS I, A | HLA-A |
| DIABETES INSIPIDUS, NEPHROGENIC, X-LINKED | |
| CD59 ANTIGEN -18-20 | CD59 |
| LEUKOCYTE ADHESION DEFICIENCY, TYPE I | LAD |
| TUMOR NECROSIS FACTOR RECEPTOR SUPERFAMILY, MEMBER 6 | TNFRSF6 |
| CD4 ANTIGEN | CD4 |
| CD8 ANTIGEN, ALPHA POLYPEPTIDE | CD8A |
| INTEGRIN, BETA-2 | ITGB2 |
| INTERFERON, GAMMA, RECEPTOR 1 | IFNGR1 |
| IMMUNODEFICIENCY WITH HYPER-IgM | |
| RHESUS BLOOD GROUP, CcEe ANTIGENS | RHCE |
| SURFACE ANTIGEN 6 | S6 |
| T-CELL ANTIGEN RECEPTOR, GAMMA SUBUNIT | TCRG |
| TYROSINE HYDROXYLASE | TH |
| HEPATOCELLULAR CARCINOMA | |
| SURFACE ANTIGEN MIC2 | MIC2 |
| BETA-2-MICROGLOBULIN | B2M |

TABLE 18-continued

Surface Antigens of Human Chromosome 17

| Long Name | Abbreviation |
|---|---|
| EPIDERMAL GROWTH FACTOR RECEPTOR | EGFR |
| FACTOR V DEFICIENCY | |
| CD44 ANTIGEN | CD44 |
| LYMPHOCYTE ANTIGEN CD5 | CD5 |
| LUPUS ERYTHEMATOSUS, SYSTEMIC | SLE |
| TRANSFERRIN RECEPTOR | TFRC |
| INSULIN-LIKE GROWTH FACTOR 2 RECEPTOR | IGF2R |

TABLE 19

Surface Antigens of Human Chromosome 18

| Long Name | Abbreviation |
|---|---|
| HEMOPHILIA A | |
| DESMOGLEIN 3 | DSG3 |
| HEMOGLOBIN-BETA LOCUS | HBB |
| MUSCULAR DYSTROPHY, PSEUDOHYPERTROPHIC PROGRESSIVE, DUCHENNE AND BECKER TYPES | |
| NUCLEAR FACTOR OF ACTIVATED T CELLS, CYTOPLASMIC, 1 | NFATC1 |
| TUMOR PROTEIN p53 | TP53 |
| RETINOBLASTOMA | RB1 |
| CYSTIC FIBROSIS TRANSMEMBRANE CONDUCTANCE REGULATOR | CFTR |
| ATAXIA-TELANGIECTASIA | AT |
| CD59 ANTIGEN P18-20 | CD59 |
| WILMS TUMOR 1 | WT1 |
| VON WILLEBRAND DISEASE | |
| WISKOTT-ALDRICH SYNDROME | WAS |
| INTERFERON, GAMMA, RECEPTOR 1 | IFNGR1 |
| ALZHEIMER DISEASE | AD |
| MAJOR HISTOCOMPATIBILITY COMPLEX, CLASS I, A | HLA-A |
| HEMOCHROMATOSIS | HFE |
| BRUTON AGAMMAGLOBULINEMIA TYROSINE KINASE | BTK |
| CHEDIAK-HIGASHI SYNDROME | CHS1 |
| INTEGRIN, BETA-2 | ITGB2 |
| BLOOD GROUP-MN LOCUS | MN |
| IMMUNODEFICIENCY WITH HYPER-IgM | |
| INTERCELLULAR ADHESION MOLECULE 1 | ICAM1 |
| LEUKOCYTE ADHESION DEFICIENCY, TYPE I | LAD |
| INTEGRIN, BETA-3 | ITGB3 |
| SEVERE COMBINED IMMUNODEFICIENCY, X-LINKED | SCIDX1 |
| LUPUS ERYTHEMATOSUS, SYSTEMIC | SLE |
| HYPOPHOSPHATEMIA, X-LINKED | |
| PLASMINOGEN ACTIVATOR, TISSUE | PLAT |
| SOLUTE CARRIER FAMILY 4, ANION EXCHANGER, MEMBER 1 | SLC4A1 |
| XG BLOOD GROUP SYSTEM | XG; PBDX |
| TYROSINE HYDROXYLASE | TH |
| V-HA-RAS HARVEY RAT SARCOMA VIRAL ONCOGENE HOMOLOG | HRAS |
| CD4 ANTIGEN | CD4 |
| CD44 ANTIGEN | CD44 |
| ADENOSINE DEAMINASE | ADA |
| THY-1 T-CELL ANTIGEN | THY1 |
| FACTOR V DEFICIENCY | |
| V-ERB-B2 AVIAN ERYTHROBLASTIC LEUKEMIA VIRAL ONCOGENE HOMOLOG 2 | ERBB2 |
| T-CELL ANTIGEN RECEPTOR, GAMMA SUBUNIT | TCRG |
| L1 CELL ADHESION MOLECULE | L1CAM |
| DISACCHARIDE INTOLERANCE I | |
| HISTOCOMPATIBILITY Y ANTIGEN | HY |
| THROMBASTHENIA OF GLANZMANN AND NAEGELI | |
| INTERLEUKIN 2 RECEPTOR, GAMMA | IL2RG |
| TUMOR NECROSIS FACTOR RECEPTOR SUPERFAMILY, MEMBER 6 | TNFRSF6 |

TABLE 19-continued

Surface Antigens of Human Chromosome 18

| Long Name | Abbreviation |
|---|---|
| RHESUS BLOOD GROUP, CcEe ANTIGENS | RHCE |
| BARE LYMPHOCYTE SYNDROME, TYPE II | |
| CD36 ANTIGEN | CD36 |
| TRANSFERRIN | TF |

TABLE 20

Surface Antigens of Human Chromosome 19

| Long Name | Abbreviation |
|---|---|
| INTERCELLULAR ADHESION MOLECULE 1 | ICAM1 |
| BLOOD GROUP-LUTHERAN SYSTEM | LU |
| PREGNANCY-SPECIFIC BETA-1-GLYCOPROTEIN 2 | PSG2 |
| MUSCULAR DYSTROPHY, PSEUDOHYPERTROPHIC PROGRESSIVE, DUCHENNE AND BECKER TYPES | |
| CYSTIC FIBROSIS TRANSMEMBRANE CONDUCTANCE REGULATOR | CFTR |
| POLIO VIRUS RECEPTOR | PVR |
| HEMOGLOBIN-BETA LOCUS | HBB |
| ALZHEIMER DISEASE | AD |
| HEMOPHILIA A | |
| FUCOSYLTRANSFERASE 1 | FUT1 |
| CD79A ANTIGEN | DC79A |
| BARE LYMPHOCYTE SYNDROME TYPE II | |
| RETINOBLASTOMA | RB1 |
| TUMOR PROTEIN p53 | TP53 |
| HEMOCHROMATOSIS | HFE |
| WILMS TUMOR 1 | WT1 |
| BASIGIN | BSG |
| KILLER CELL IMMUNOGLOBULIN-LIKE RECEPTOR, TWO DOMAINS, SHORT CYTOPLASMIC TAIL, 1 | KIR2DS1 |
| PLASMINOGEN ACTIVATOR RECEPTOR, UROKINASE-TYPE | PLAUR |
| TYRO PROTEIN TYROSINE KINASE-BINDING PROTEIN | TYROBP |
| BLOOD GROUP-OK | OK |
| WISKOTT-ALDRICH SYNDROME | AS |
| L1 CELL ADHESION MOLECULE | L1CAM |
| BRUTON AGAMMAGLOBULINEMIA TYROSINE KINASE | BTK |
| INTEGRIN, BETA-3 | ITGB3 |
| TUMOR NECROSIS FACTOR RECEPTOR SUPERFAMILY, MEMBER 6 | TNFRSF6 |
| INTEGRIN, BETA-1 | ITGB1 |
| CD59 ANTIGEN P18-20 | CD59 |
| VON WILLEBRAND DISEASE | |
| SOLUTE CARRIER FAMILY 3, MEMBER 2 | SLC3A2 |
| IMMUNODEFICIENCY WITH HYPER-IgM | |
| CD44 ANTIGEN | CD44 |
| LEUKOCYTE ADHESION DEFICIENCY, TYPE I | LAD |
| SOLUTE CARRIER FAMILY 4, ANION EXCHANGER, MEMBER 1 | SLC4A1 |
| ATAXIA-TELANGIECTASIA | AT |
| ANTITHROMBIN III DEFICIENCY | |
| MAJOR HISTOCOMPATIBILITY COMPLEX, CLASS I, A | HLA-A |
| T-CELL ANTIGEN RECEPTOR, ALPHA SUBUNIT | TCRA |
| INTERFERON, GAMMA, RECEPTOR 1 | IFNGR1 |
| CHEDIAK-HIGASHI SYNDROME | CHS1 |
| DIABETES INSIPIDUS, NEPHROGENIC, X-LINKED | |
| THY-1 T-CELL ANTIGEN | THY1 |
| TRANSFERRIN | TF |
| MEMBRANE-SPANNING 4 DOMAINS, SUBFAMILY A, MEMBER 1 | MS4A1 |
| RHESUS BLOOD GROUP, CcEe ANTIGENS | RHCE |
| T-CELL ANTIGEN RECEPTOR, GAMMA SUBUNIT | TCRG |
| TRANSFERRIN RECEPTOR | TFRC |
| V-ERB-B2 AVIAN ERYTHROBLASTIC LEUKEMIA VIRAL ONCOGENE HOMOLOG 2 | ERBB2 |
| FUCOSYLTRANSFERASE 4 | FUT4 |
| ADENOSINE DEAMINASE | ADA |

TABLE 21

Surface Antigens of Human Chromosome 20

| Long Name | Abbreviation |
|---|---|
| CD59 ANTIGEN P18-20 | CD59 |
| ADENOSINE DEAMINASE | ADA |
| HEMOGLOBIN—BETA LOCUS | HBB |
| RETINOBLASTOMA | RB1 |
| CYSTIC FIBROSIS TRANSMEMBRANE CONDUCTANCE REGULATOR | CFTR |
| MUSCULAR DYSTROPHY, PSEUDOHYPERTROPHIC PROGRESSIVE, DUCHENNE AND BECKER TYPES | |
| PROTEIN-TYROSINE PHOSPHATASE, NONRECEPTOR TYPE, SUBSTRATE 1 | PTPNS1 |
| TUMOR NECROSIS FACTOR RECEPTOR SUPERFAMILY, MEMBER 5 | TNFRSF5 |
| CENTROMERIC PROTEIN B | CENPB |
| ATAXIA-TELANGIECTASIA | AT |
| HEMOPHILIA A | |
| HEMOCHROMATOSIS | HFE |
| WILMS TUMOR 1 | WT1 |
| VON WILLEBRAND DISEASE | |
| TUMOR PROTEIN p53 | TP53 |
| SOLUTE CARRIER FAMILY 4, ANION EXCHANGER, MEMBER 1 | SLC4A1 |
| INTEGRIN, BETA-3 | ITGB3 |
| PHOSPHODIESTERASE I/ NUCLEOTIDE PYROPHOSPHATASE 1 | PDNP1 |
| LEUKOCYTE ADHESION DEFICIENCY, TYPE I | LAD |
| ALZHEIMER DISEASE | AD |
| FACTOR V DEFICIENCY | |
| WISKOTT-ALDRICH SYNDROME | WAS |
| BRUTON AGAMMAGLOBULINEMIA TYROSINE KINASE | BTK |
| T-CELL ANTIGEN RECEPTOR, ALPHA SUBUNIT | TCRA |
| MEMBRANE COMPONENT, CHROMOSOME 1, SURFACE MARKER 1 | M1S1 |
| CD44 ANTIGEN | CD44 |
| TUMOR NECROSIS FACTOR RECEPTOR SUPERFAMILY, MEMBER 6 | TNFRSF6 |
| IMMUNODEFICIENCY WITH HYPER-IgM | |
| MAJOR HISTOCOMPATIBILITY COMPLEX, CLASS I | HLA-A |
| FUCOSYLTRANSFERASE 4 | FUT4 |
| ANTITHROMBIN III DEFICIENCY | |
| INTERFERON, GAMMA, RECEPTOR 1 | IFNGR1 |
| SEVERE COMBINED IMMUNODEFICIENCY, X-LINKED | SCIDX1 |
| RHESUS BLOOD GROUP, CcEe ANTIGENS | RHCE |
| INTERCELLULAR ADHESION MOLECULE 1 | ICAM1 |
| EPIDERMAL GROWTH FACTOR RECEPTOR | EGFR |
| PLASMINOGEN ACTIVATOR, TISSUE | PLAT |
| BLOOD GROUP—MN LOCUS | MN |
| THY-1-CELL ANTIGEN | THY1 |
| 0TRANSFERRIN | TF |
| DIABETES INSIPIDUS, NEPHROGENIC, X-LINKED | |
| INTERLEUKIN 2 RECEPTOR, GAMMA | IL2RG |
| XG BLOOD GROUP SYSTEM | XG; PBDX |
| V-ERB-B2 AVIAN ERYTHROBLASTIC LEUKEMIA VIRAL ONCOGENE HOMOLOG2 | ERBB2 |
| V-HA-RAS HARVEY RAT SARCOMA VIRAL ONCOGENE HOMOLOG | HRAS |
| INTERLEUKIN 4 RECEPTOR | IL4R |
| INSULIN-LIKE GROWTH FACTOR 2 RECEPTOR | IGF2R |
| CENTROMERIC PROTEIN C1 | CENPC1 |
| DIPEPTIDYLPEPTIDASE IV | DPP4 |
| LUPUS ERYTHEMATOSUS, SYSTEMIC | SLE |

TABLE 22

Surface Antigens of Human Chromosome 21

| Long Name | Abbreviation |
|---|---|
| ALZHEIMER DISEASE | AD |
| LEUKOCYTE ADHESION DEFICIENCY, TYPE I | LAD |

TABLE 22-continued

Surface Antigens of Human Chromosome 21

| Long Name | Abbreviation |
|---|---|
| INTEGRIN, BETA-2 | INTGB2 |
| MUSCULAR DYSTROPHY, PSEUDOHYPERTROPHIC PROGRESSIVE, DUCHENNE AND BECKER TYPES | |
| CYSTIC FIBROSIS TRANSMEMBRANE CONDUCTANCE REGULATOR | CFTR |
| RETINOBLASTOMA | RB1 |
| SURFACE ANTIGEN 21 | S14 |
| HEMOPHILIA A | |
| HEMOGLOBIN—BETA LOCUS | HBB |
| ATAXIA-TELANGIECTASIA | AT |
| HEMOCHROMATOSIS | HFE |
| IMMUNODEFICIENCY WITH HYPER-IgM | |
| TUMOR PROTEIN p53 | TP53 |
| BRUTON AGAMMAGLOBULINEMIA TYROSINE KINASE | BTK |
| INTERFERON, GAMMA, RECEPTOR 1 | IFNGR1 |
| XG BLOOD GROUP SYSTEM | XG; PBDX |
| V-HA-RAS HARVEY RAT SARCOMA VIRAL ONCOGENE HOMOLOG | HRAS |
| VON WILLEBRAND DISEASE | |
| WILMS TUMOR 1 | WT1 |
| SEVERE COMBINED IMMUNODEFICIENCY, X-LINKED | SCIDX1 |
| V-ERB-B2 AVIAN ERYTHROBLASTIC LEUKEMIA VIRAL ONCOGENE HOMOLOG 2 | ERBB2 |
| THY-1 T-CELL ANTIGEN | THY1 |
| PLASMINOGEN ACTIVATOR, TISSUE | PLAT |
| MAJOR HISTOCOMPATIBILITY COMPLEX, CLASS I, A | HLA-A |
| TUMOR NECROSIS FACTOR RECEPTOR SUPERFAMILY, MEMBER 6 | HLA-A |
| T-CELL ANTIGEN RECEPTOR, ALPHA SUBUNIT | TCRA |
| EPIDERMAL GROWTH FACTOR RECEPTOR | EGFR |
| T-CELL ANTIGEN RECEPTOR, GAMMA SUBUNIT | TCRG |
| INTEGRIN, BETA-3 | ITGB3 |
| TRANSFERRIN | TF |
| CD59 ANTIGEN P18-20 | CD59 |
| WISKOTT-ALDRICH SYNDROME | WAS |
| RHESUS BLOOD GROUP, CcEe ANTIGENS | RHCE |
| BLOOD GROUP—MN LOCUS | MN |
| CD9 ANTIGEN | CD9 |
| ADENOSINE DEAMINASE | ADA |
| THROMBASTHENIA OF GLANZMANN AND NAEGELI | |
| CHEDIAK-HIGASHI SYNDROME | CHS1 |
| CD83 ANTIGEN | CD83 |
| DISACCHARIDE INTOLERANCE I | |
| FACTOR V DEFICIENCY | |
| FLAUJEAC FACTOR DEFICIENCY | |
| TYROSINE HYDROXYLASE | TH |
| DIABETES INSIPIDUS, NEPHROGENIC, X-LINKED | |
| CD36 ANTIGEN | CD36 |
| ANTITHROMBIN III DEFICIENCY | |
| L1 CELL ADHESION MOLECULE | L1CAM |
| SOLUTE CARRIER FAMILY 4, ANION EXCHANGER, MEMBER 1 | SLC4A1 |
| PLATELET-ENDOTHELIAL CELL ADHESION MOLECULE | PECAM1 |
| INTEGRIN, ALPHA-L | ITGAL |

TABLE 23

Surface Antigens of Human Chromosome 22

| Long Name | Abbreviation |
|---|---|
| HEMOPHILIA A | |
| HEMOGLOBIN—BETA LOCUS | HBB |
| CYSTIC FIBROSIS TRANSMEMBRANE CONDUCTANCE REGULATOR | CFTR |
| INTERLEUKIN 2 RECEPTOR, BETA | IL2RB |
| RETINOBLASTOMA | RB1 |

TABLE 23-continued

Surface Antigens of Human Chromosome 22

| Long Name | Abbreviation |
|---|---|
| ALZHEIMER DISEASE | AD |
| ATAXIA-TELANGIECTASIA | AT |
| WISKOTT-ALDRICH SYNDROME | WAS |
| HEMOCHROMATOSIS | HFE |
| TUMOR PROTEIN p53 | TP53 |
| BRUTON AGAMMAGLOBULINEMIA TYROSINE KINASE | BTK |
| MUSCULAR DYSTROPHY, PSEUDOHYPERTROPHIC PROGRESSIVE, DUCHENNE AND BECKER TYPES | |
| WILMS TUMOR 1 | WT1 |
| MAJOR HISTOCOMPATABILITY COMPLEX, CLASS I, A | HLA-A |
| BETA-2 MICROGLOBULIN | B2M |
| FLOTILLIN 2 | FLOT2 |
| CD59 ANTIGEN P18-20 | CD59 |
| IMMUNODEFICIENCY WITH HYPER-IgM | |
| VON WILLEBRAND DISEASE | |
| ADENOSINE DEAMINASE | ADA |
| V-HA-RAS HARVEY RAT SARCOMA VIRAL ONCOGENE HOMOLOG | HRAS |
| INTEGRIN, BETA-3 | ITGB3 |
| LETHAL ANTIGEN-A1 | AL-A1 |
| INTERFERON, GAMMA, RECEPTOR 1 | IFNGR1 |
| T-CELL ANTIGEN RECEPTOR, ALPHA SUBUNIT | TCRA |
| XG BLOOD GROUP SYSTEM | XG; PBDX |
| L1 CELL ADHESION MOLECULE | L1CAM |
| THROMBASTHENIA OF GLANZMANN AND NAEGELI | |
| FACTOR V DEFICIENCY | |
| PLASMINOGEN ACTIVATOR, TISSUE | PLAT |
| T-CELL ANTIGEN RECEPTOR, GAMMA SUBUNIT | TCRG |
| INTEGRIN, BETA-2 | ITGB2 |
| LEUKOCYTE ADHESION DEFICIENCY, TYPE I | LAD |
| LUPUS ERYTHEMATOSUS, SYSTEMIC | SLE |
| SOLUTE CARRIER FAMILY 4, ANION EXCHANGER, MEMBER 1 | SLC4A1 |
| TYROSINE HYDROXYLASE | TH |
| HYPOPHOSPHATEMIA, X-LINKED | |
| BLOOD GROUP—MN LOCUS | MN |
| TUMOR NECROSIS FACTOR RECEPTOR SUPERFAMILY, MEMBER 6 | TNFRSF6 |
| BARE LYMPHOCYTE SYNDROME, TYPE II | |
| SEVERE COMBINED IMMUNODEFICIENCY, X-LINKED | SCIDX1 |
| TRANSFERRIN RECEPTOR | TFRC |
| RHESUS BLOOD GROUP, CcEe ANTIGENS | RHCE |
| SURFACE ANTIGEN 21 | S14 |
| CD86 ANTIGEN | CD86 |
| DIABETES INSIPIDUS, NEPHROGENIC, X-LINKED | |
| BLOOD GROUP—LUTHERAN SYSTEM | LU |
| CD36 ANTIGEN | CD36 |
| BULLOUS PEMPHIGOID ANTIGEN 1 | BPAG1 |
| FLAUJEAC FACTOR DEFICIENCY | |

TABLE 24

Surface Antigens of Human Chromosome X

| Long Name | Abbreviation |
|---|---|
| BRUTON AGAMMAGLOBULINEMIA TYROSINE KINASE | BTK |
| MUSCULAR DYSTROPHY, PSEUDOHYPERTROPHIC PROGRESSIVE, DUCHENNE AND BECKER TYPE | |
| SEVERE COMBINED IMMUNODEFICIENCY, X-LINKED | SCIDX1 |
| IMMUNODEFICIENCY WITH HYPER-IgM | |
| WISKOTT-ALDRICH SYNDROME | WAS |
| HYPOPHOSPHATEMIA, X-LINKED | |
| DIABETES INSIPIDUS, NEPHROGENIC, X-LINKED | |
| HEMOPHILIA A | |

TABLE 24-continued

Surface Antigens of Human Chromosome X

| Long Name | Abbreviation |
|---|---|
| XG BLOOD GROUP SYSTEM | XG; PBDX |
| SURFACE ANTIGEN, X-LINKED | SAX |
| ATAXIA-TELANGIECTASIA | AT |
| INTEGRIN, ALPHA-X | ITGAX |
| RETINOBLASTOMA | RB1 |
| INTERLEUKIN 2 RECEPTOR, GAMMA | IL2RG |
| L1 CELL ADHESION MOLECULE | L1CAM |
| HEMOGLOBIN—BETA LOCUS | HBB |
| SURFACE ANTIGEN MIC2 | MIC2 |
| V-HA-RAS HARVEY RAT SARCOMA VIRAL ONCOGENE HOMOLOG | HRAS |
| TUMOR PROTEIN p53 | TP53 |
| VON WILLEBRAND DISEASE | |
| MIC2 SURFACE ANTIGEN, Y-CHROMOSOMAL | MIC2Y |
| LEUKOCYTE ADHESION DEFICIENCY, TYPE 1 | LAD |
| WILMS TUMOR 1 | WT1 |
| INTEGRIN, BETA-2 | ITGB2 |
| CYSTIC FIBROSIS TRANSMEMBRANE CONDUCTANCE REGULATOR | CFTR |
| SHORT STATURE | SS |
| HISTOCOMPATIBILITY Y ANTIGEN | HY |
| HOMEO BOX GENE HB9 | HLXB9 |
| CENTROMERIC PROTEIN C1 | CENPC1 |
| BLOOD GROUP-KELL-CELLANO SYSTEM | KEL |
| FUCOSYLTRANSFERASE 4 | FUT4 |
| DIPEPTIDYLPEPTIDASE IV | DPP4 |
| BARE LYMPHOCYTE SYNDROME, TYPE II | |
| ADENOSINE DEAMINASE | ADA |
| LEUKOCYTE ADHESION DEFICIENCY, TYPE II | |
| SIALOPHORIN | SPN |
| CATHEPSIN E | CTSE |
| ANTITHROMBIN II DEFICIENCY | |
| FUCOSYLTRANSFERASE 1 | FUT1 |
| INTEGRIN, ALPHA-L | ITGAL |
| TUMOR NECROSIS FACTOR RECEPTOR SUPERFAMILY, MEMBER 5 | TNFRSF5 |
| SOLUTE CARRIER FAMILY 3, MEMBER 1 | SLC3A1 |
| XG REGULATOR | XGR |
| Fc FRAGMENT OF IgE, HIGH AFFINITY I, RECEPTOR FOR, ALPHA SUBUNIT | FCER1A |

TABLE 25

Surface Antigens of Human Chromosome Y

| Long Name | Abbreviation |
|---|---|
| HISTOCOMPATABILITY Y ANTIGEN | HY |
| XG BLOOD GROUP SYSTEM | XG; PBDX |
| MIC2 SURFACE ANTIGEN MIC2 | MIC2 |
| ATAXIA-TELANGIECTASIA | AT |
| HEMOPHILIA A | |
| SOLUTE CARRIER FAMILY 3, MEMBER 2 | SLC3A2 |
| HEMOGLOBIN—BETA LOCUS | HBB |
| RETINOBLASTOMA | RB1 |
| CYSTIC FIBROSIS TRANSMEMBRANE CONDUCTANCE REGULATOR | CFTR |
| HEMOCHROMATOSIS | HFE |
| IMMUNODEFICIENCY WITH HYPER-IgM | |
| CHEDIAK-HIGASHI SYNDROME | CHS1 |
| RHESUS BLOOD GROUP-ASSOCIATED GLYCOPROTEIN | RHAG |
| DIPEPTIDYLPEPTIDASE IV | DPP4 |
| SHORT STATURE | SS |
| DIABETES INSIPIDUS, NEPHROGENIC, X-LINKED | |
| FACTOR V DEFICIENCY | |
| CD36 ANTIGEN | CD36 |
| LUPUS ERYTHEMATOSUS, SYSTEMIC | SLE |
| CD24 ANTIGEN | CD24 |
| BASIGIN | BSG |

Examples of non-surface antigen proteins that may also be used as a linked gene with this method are thymidine kinase, encoded by a gene on Human Chromosome 17 and HRPT, encoded by a gene on Human Chromosome X. Selection of cells expressing these and similar linked genes could be accomplished through antibody analysis, but it might also be accomplished through simple cell culture in selective medium.

Separation of Cells Expressing Linked Genes

After genetic transfer of the test gene, it would be optimal to separate the cells which have taken up the DNA from those which have not. The mixed population may be isolated through known selection processes or through the expression of the linked gene. This ensures that the cell used for the following functional assays actually contains copy of the test gene.

If the linked gene encodes a surface antigen, target cells may be identified by incubation with fluorescently labeled antibodies. These cells may be detected through microscopy or FACS analysis. Additionally, they may be sorted from a non-expressing population of cells.

Panning and immunoprecipitation or precipitation through magnetic beads may serve as alternatives to FACS for separating cells that have received the test gene. These methods might be used as described in Small, M., et al., "Isolation of CD3-, CD4-, CD8-, IL-2R+ thymocyte precursors by panning", J. Immunol. Methods 167 (1–2): 103–107 (1994); Hoogenboom, H. R., et al., "Selection-dominant and nonaccessible epitopes on cell-surface receptors revealed by cell-panning with a large phage antibody library", Eur. J. Biochem. 260(3): 774–84 (1999); Wysocki, L. J. and Sato, V. L. "'Panning' for lymphocytes: a method for cell selection", Proc. Natl. Acad. Sci. U.S.A. 75(6): 2844–2848 (1978); and Maryanski, J. L., et al., "A simple panning method for the selection of cell surface antigen transfectants", J. Immunol. Methods 79(1): 159–163 (1985), incorporated by reference herein. Briefly, in the panning method a glass or plastic surface might be coated with a substance, such as an antibody, that will bind with a linked surface gene. Thus, cells expressing the linked surface gene could be separated from those that did not. After panning one could examine the target cells microscopically for the target gene. It may additionally be possible to use one linked gene for the panning analysis and a second linked gene for the microscopic assay.

For separation by immunoprecipitation or magnetic beads, the beads may be coated with a ligand, antigen or antibody so that only cells positive for a particular surface marker will be bound to the beads. Cells expressing the linked surface marker may then be isolated from other target cells through separation of the beads into new medium. The target cells could then be further examined for receipt of the test gene or expression of the test protein on the beads or after separation from the beads. Some potential techniques of this nature are described in Jurman, M. E., et al., "Visual identification of individual transfected cells for electrophysiology using antibody-coated beads", Biotechniques 17(5): 876–881 (1994); Thomas, T. E. et al., "Specific binding and release of cells from beads using cleavable tetrameric antibody complexes", J. Immunol. Methods 120(2): 221–231 (1989); Partington, K. M., "A novel methods of cell separation based on dual parameter immunomagnetic cell selection", J. Immunol. Methods 223(2): 195–205 (1999); Patel, D. and Rickwood, D., "Optimization of conditions for specific binding of antibody-coated beads to cells", J. Immunol. Methods 184(1): 71–80 (1995); Pilling, D., et al., "The kinetics of interaction between lymphocytes and magnetic polymer particles", *J. Immunol. Methods* 122(2): 235–41 (1989); Widjojoatmodjo, M. N., et al., "Comparison of immunmagnetic beads coated with protein A, protein G, or goat anti-mouse immunoglobulins. Applications in enzyme immunoassays and immunomagnetic separations", *J. Immunol. Methods*. 165(1): 11–19 (1993); and Vaccare, D. E., "Applications of magnetic separation: cell sorting", *Am. Biotechnol. Lab*. 8(5): 32–35 (1990), incorporated by reference herein.

Fluorescently labeled antibodies may also be used to detect linked genes which are expressed intracellularly. However, such proteins may be more readily detectable by functional assays. Such assays will vary as greatly as the linked proteins. However, useful assays similar to those described below for detection of the test protein will be appropriate. Functional assays may also be useful in combination with surface antigens. Any assay, whether functional or antigen-based is appropriate so long as it detects expression of the linked gene.

Functional Assays for Test Gene Products

In a most preferred embodiment of the invention, the hybrid target cell population is evaluated for presence of the test gene by analysis of the function of the test protein. This testing may also be accomplished by a functional assay that allows functional protein to be distinguished from mutant forms that may be non-functional or partially functional if a loss-of-function mutation, including a partial loss-of-function mutation, an alteration of function mutation or a dominant negative mutation is present or additionally functional if a gain-of-function mutation is present. Functional analysis of the expressed protein may also be accomplished by an assay which detects the restoration of a function in target cells which are deficient in that function.

Assays currently in development may also be used with the method of this invention to detect cells that have received the test gene. These assays may also prove useful for detection of expression of a functional test gene product. Some such assays include those described in Bildiriel, L. and Rickwood, D., "Fractionation of differentiating cells using density perturbation", *J. Immunol. Methods* 240(1–2): 93–99 (June, 2000); Perrin, A. et al., "Immunomagnetic concentration of antigens and detection based on a scanning force microscopic immunoassay", *J. Immunol. Methods* 224(1–2): 77–87 (1999); and Schmitz, B., et al., "Magnetic activated cell sorting (MACS)—a new immunomagnetic method for megakaryocytic cell isolation: comparison of different separation techniques", *Eur. J. Immunol*. 52(5): 267–275 (1994), incorporated herein by reference for use in detection of both cells that received the test gene and cells in which a functional test gene product is expressed.

This invention provides a more economical or efficient means of detecting heterozygous loss-of-function or gain-of-function mutations than other methods presently available. It additionally may be adapted in many ways to optimize its utility for detecting a particular heterozygous loss-of-function or gain-of-function mutation including partial loss-of-function, alteration of function and dominant negative mutations based on the function of the wild type and/or mutant proteins. The sensitivity and specificity of any particular test can be determined by how well the method of detection of the test protein mimics or parallels the function of the gene in vivo.

In a preferred embodiment of the invention, target cells are analyzed not only for presence of the test gene, but also for its expression and the function of the expressed protein. The optimal goal of such analysis is to detect the function of the expressed test protein in a manner as analogous to the in vivo situation as possible. For some test genes, it may be more appropriate to distinguish between wild type or functional mutant alleles and loss-of-function or gain-of-function mutant alleles using immunological analysis. Table 26 lists diseases related to loss-of-function or gain-of-function mutations, appropriate target cells for such disease, and appropriate assays. More detailed descriptions of some assays are provided below. Table 26 and the descriptions below are not intended to describe all assays that may be used to detect expression or function of a test protein. Many other functional or expression-based assays may be more appropriate for other test genes, as will be appreciated by one skilled in the art.

TABLE 26

Potential Target Diseases, Related Genes and Mutations and Assays

| Disorder | Gene(s) and Known Mutations | Target Cells | Assays |
| --- | --- | --- | --- |
| Familial hypercholsterolemia | LDLR; loss-of-function | LDLR deficient CHO cells | Uptake of fluorescent LDL |
| HNPCC | MSH1, MSH2, PMS1, PMS2; loss-of-function | MSH1, MSH2, PMS1, PMS2 deficient mouse or human cells; mismatch repair deficient mouse, human or yeast cells | Mismatch repair functional assay |
| Breast or ovarian cancer | BRCA1; BRCA2; loss-of-function | BRCA1/ BRCA2 deficient mouse or human cells | 2-hybrid inhibition or immunological assay |
| Neurofibromatosis | NF1; NF2; loss-of-function | NF1, NF2 deficient mouse or human cells | 2-hybrid inhibition or immunological assay |
| Polyposis of the colon | APC; loss-of-function | APC deficient mouse or human cells | 2-hybrid inhibition or immunological assay |
| Duchenne dystrophy | Dystrophin genes; loss-of-function | Dystrophin deficient myoblasts | immunodetection of dystrophin complex or functional assay; in vivo assay |
| Cystic fibrosis | CFTR; loss-of-function | CFTR deficient cells; CFPAC-1 | Ion channel activity assay |
| Li Fraumenti | loss-of-function; possible gain-of-function | | 2-hybrid inhibition or immunological assay |
| Tuberous sclerosis | loss-of-function | | 2-hybrid inhibition or immunological assay |
| Gorlin syndrome | loss-of-function | | 2-hybrid inhibition or immunological assay |
| Von Hippel-Lindau | loss-of-function | | 2-hybrid inhibition or immunological assay |
| Porphyrias | loss-of-function | | Histochemistry or 2-hybrid inhibition or immunological assay |
| Osteogenesis imperfecta | loss-of-function; gain-of-function possible | | 2-hybrid inhibition or immunological assay |
| Marfan | loss-of-function; -gain of-function | | 2-hybrid inhibition or immunological assay |
| Hemophilia | loss-of-function | | Coagulant activity of 2-hybrid inhibition or immunological assay |

TABLE 26-continued

Potential Target Diseases, Related Genes and Mutations and Assays

| Disorder | Gene(s) and Known Mutations | Target Cells | Assays |
| --- | --- | --- | --- |
| SCID | loss-of-function | | 2-hybrid inhibition or immunological assay |

Functional Assay: Endocytic Uptake of Ligand

For test genes encoding a receptor, functional analysis may comprise an assay to detect normal interaction of that receptor with its ligand. If a fluorescently labeled ligand is used, cells may then be examined for its binding or uptake via microscopy or FACS. For example, to detect a defect in the LDLR (low density lipoprotein receptor), target cells containing the test gene may be incubated with commercially available, fluorescently labeled LDL (low density lipoprotein). (See Corsetti, J. P. et al., "The labeling of lipoproteins for studies of cellular binding with a fluorescent lipophilic dye", Anal. Biochem. 195: 122 (1991), incorporated by reference herein, for a description of this technique.) Target cells in which the test protein is expressed and functions normally will internalize the labeled LDL while those with loss-of-function mutations will not. (This is demonstrated in the Examples below.) Cells that have internalized the LDL are visible through microscopy. For the protein to carry out this function, it must be synthesized, stable, properly processed and capable of ligand binding and it must be able to carry out the normal internalization function. Rare mutations that permit ligand binding but block internalization might also be detectable by this technique, as cells expressing such mutant alleles will show LDL staining at the plasma membrane, but not in the cytoplasm.

One surface antigen, ICAM-1 (intercellular adhesion molecule-1) is known to be linked to test gene, LDLR. In a more preferred embodiment, microcell-mediated chromosome transfer (MMCT) is used to transfer Human Chromosome 19 from lymphoblast donor cells to Chinese Hamster Ovary (CHO) target cells. Chromosome 19 comprises the test gene which encodes human LDLR and the gene that encodes ICAM-1. The ICAM-1 gene is naturally linked to the LDLR gene such that separation by recombination or chromosome damage is unlikely. After genetic transfer, target cells are incubated with fluorescently labeled LDL under conditions that allow LDL binding to wild type or functional LDLR and endocytic uptake by the cells. Cells in which the LDLR gene is functional exhibited cytoplasmic staining whereas those with a LDLR loss-of-function mutation are not labeled. Cells with an LDLR partial loss-of-function mutation may exhibit reduced cytoplasmic staining, only surface staining or no staining. In addition, target cells can be labeled with an anti-ICAM-1 antibody. Positively stained ICAM cells may be sorted from unlabelled cells. Slides of the target cells are then prepared and fluorescent microscopy used to visualize cells labeled with the ICAM-1 antibody and those labeled by uptake of fluorescent LDL such that the ratio of cells that express functional LDLR to the total number of cells that received the test gene and express ICAM-1 may be calculated. LDLR linkage to ICAM-1 allows the application of both immunodetection of linked surface antigen and a functional assay of the test gene (endocytic LDL uptake).

Functional Assay: Ion Channel Activity

The CFTR (Cystic Fibrosis Transmembrane Conductance Regulator Protein) gene is another potential test gene in this method. Loss-of-function mutations in the CFTR gene can lead to cystic fibrosis in individuals homozygous for such mutations. Early and efficient detection of these individuals can lead to more effective treatment of the disease. Additionally, detection of individuals heterozygous for a CFTR loss-of-function mutation is useful for medical and research purposes and especially for genetic counseling. Since CFTR encodes a chloride channel, a relevant functional assay must measure ion transport through electrophysiological techniques. One such functional assay is described in Mansoura, M. K. et al., "Fluorescent chloride indicators to assess the efficacy of CFTR cDNA delivery", Hum. Gene Ther. 10(6): 861–75 (1999), incorporated herein by reference.

Functional Assay: Mismatch Repair

Figure 4:
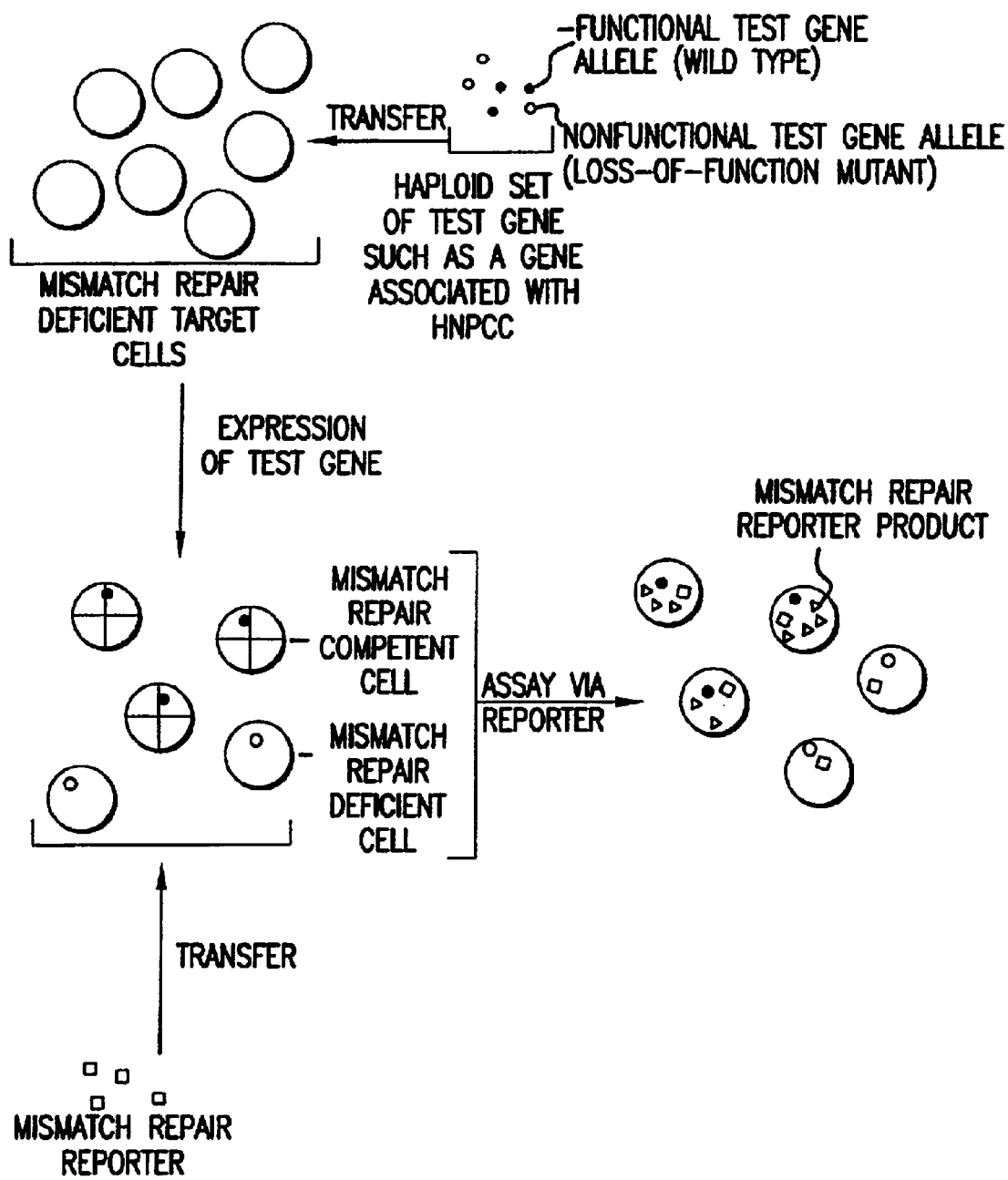
FIG. 4 depicts a potential assay for loss-of-function mutations in mismatch repair-related test genes, such as those associated with HNPCC, using mismatch repair deficient target cells.

HNPCC (hereditary nonpolyposis colon cancer) is caused by mutations in DNA mismatch repair genes, e.g. MLH1, MSH1, PMS1, PMS2. Any of these mutations may be detected through the use of a mismatch repair functional assay. The chosen target cells must be mismatch repair deficient. If a test gene, associated with HNPCC, encodes for a functional mismatch repair protein, its expression in the target cells should restore mismatch repair. Cells, which incorporated a mutant allele of an HNPCC associated gene, will continue to be defective in mismatch repair. Restoration of function may be detected through the use of various reporter gene system known in the art. FIG. 4 depicts one potential mismatch repair assay. A variety of other tests which analyze for mismatch repair are described in Corrette-Bennet, S. E. and Lahue, R. S., "Mismatch Repair Assay", Methods Mol Biol. 113: 121 (1999); Bill, C. A. et al., "Efficient repair of all types of single-base mismatched in recombination intermediates in Chinese hamster ovary cells. Competition between long-patch and G-T glycosylase-mediated repair of G-T mismatches", Genetics 149: 1935 (1998); Varlet, I., et al., "DNA mismatch repair in Xenopus egg extracts; repair efficiency and DNA repair synthesis for all single base-pair mismatches", Proc. Natl. Acad. Sci. U.S.A. 87: 7883 (1990); and Shimodaira, H. et al., Nat. Genet. 19: 384 (1998), incorporated herein by reference. Yeast cells might prove particularly attractive for this type of testing. An exemplary mismatch repair assay in yeast cells is described in Shimodaira, H., et al., "Functional Analysis of Human MLH1 mutations in Saccharomyces cervisiae", Nat. Genet. 19: 384 (1998), published erratum in Nat. Genet. 21(2): 241 (1999), incorporated herein by reference. As for other genes, functional analysis assays might incorporate a variety of detection formats including microscopy, FACS, or perhaps inspection for yeast colonies on culture plates.

Functional Assay: Two Hybrid System

Since many genes associated with inherited genetic disorders have undergone extensive biochemical analysis, they have known binding partners. Thus, functional assays incorporating two hybrid analysis may be applied to practice the invention. The target cell can be analyzed for the presence of a functional copy of the test gene, if the test protein demonstrates a successful protein-protein interaction with a known binding partner. For a description of a 2-hybrid system useful in the present invention see, e.g. Bartel, P. L. and Fields, S., "Analyzing protein-protein interactions using a two-hybrid system", Methods Enzymol. 254: 241 (1995); Schwartz, H. et al., "Mutation detection by a two-hybrid assay", Hum. Mol. Genet. 7: 1029 (1998; and Germino, F. J. and Moskowitz, N. K., "Screening for protein-protein interactions", *Methods Enzymol.* 303: 422–50 (1999), incorporated herein by reference. The use of a standard or inhibition two-hybrid assay must be designed to comprise a test system and a reporter system. The reporter system must not interfere with the test system and allow for assay of either positive or negative interactions.

Figure 5:
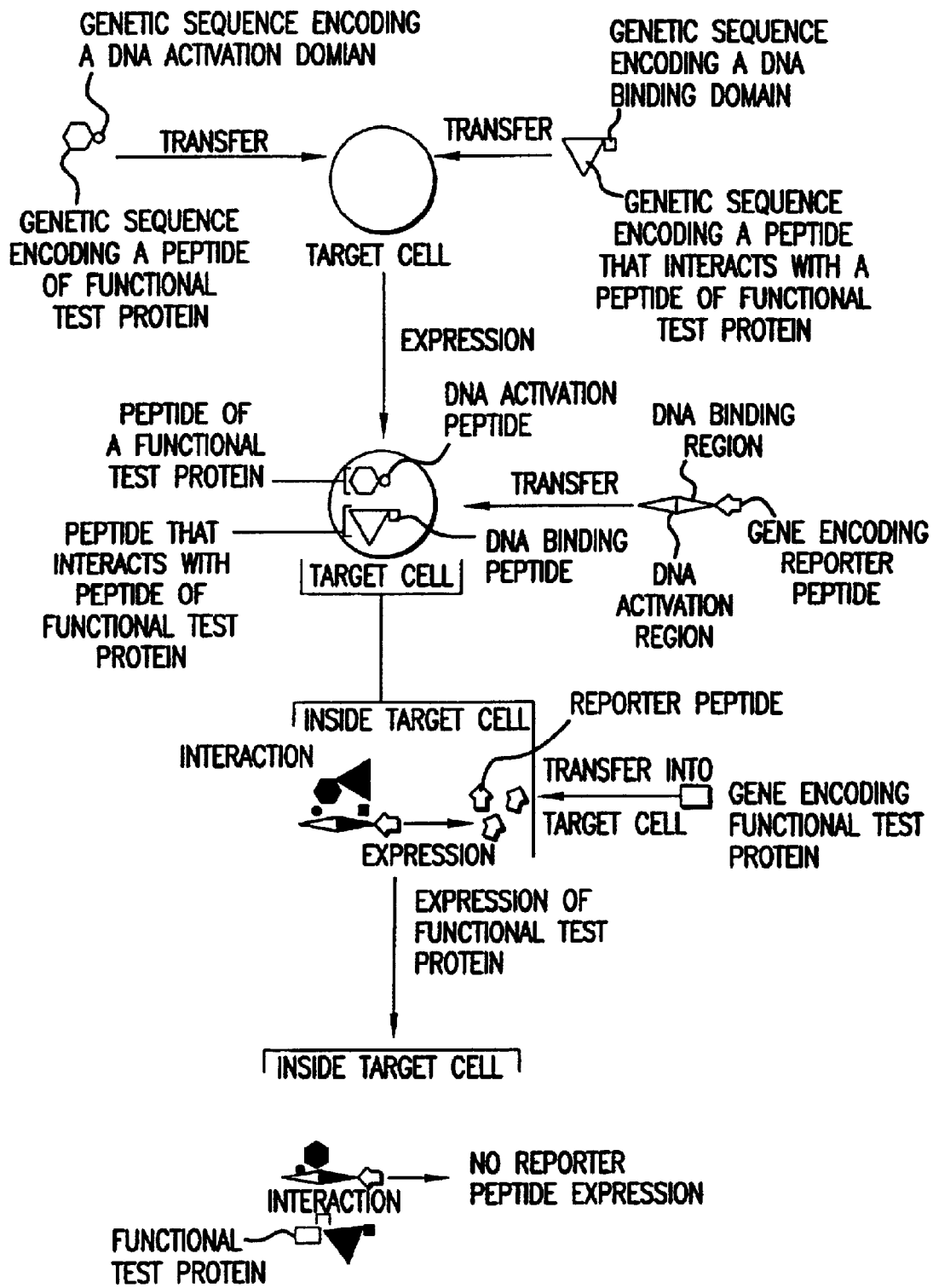
FIG. 5 shows an inhibition two-hybrid inhibition assay that may be used to detect functional test protein.

More specifically, an appropriate two-hybrid assay might be developed by expressing in the hybrid target cells a fragment of the test gene fused to a DNA binding domain under the control of a constitutive promoter. The fragment of the test gene should encode at least the interactive portion the test protein for which capacity to interact with another protein is to be assayed. The target cells would also be provided with another construct that expresses at least the interactive portion of the protein with which the test protein is to interact fused with a DNA activation domain perhaps under the control of a tetracycline-regulated promoter. These two constructs comprise the test system. The target cells should be further provided with a reporter system such that a detectable product such as GFP, luciferase, or secreted a-fetoprotein is produced only if the test protein interacts with the reporter gene product. Further, for more sensitive interference-competition assays, the fragment of the gene of interest could be chosen so as to have a somewhat weaker interaction than the full length, functional or wild type protein. In addition, the ratio of the test protein to the interacting protein could be controlled through the tetracycline promoter. FIG. 5 describes a 2-hybrid assay of this type that may be used with the present invention.

While establishment of a target cell line with the appropriate test and reporter systems might require a moderate amount of time, the techniques should be routine to one skilled in the art for most potential target cells and assays. Further, the single target cell line would be useful for all individuals regarding analysis of the test gene and possibly the target disease. After establishment of the target cell line, the test gene might be delivered to is by any of the methods described above. Function of the test gene may be measured by its ability to compete with the DNA binding/protein fragment of the test system and thereby decrease expression of the reporter gene. For a test protein to compete in this type of assay, it would have to be synthesized, stable, and capable of interaction with its physiological partner, the interacting protein (reporter gene product).

Functional Assay: GFP Fusion Protein

Another assay might test for the ability of the test protein to interact with a known fluorescently tagged binding partner. If the interacting protein were expressed in the target cell as a GFP fusion protein and this binding interaction resulted in a known subcellular translocation, one would be able to detect any known changes in subcellular localization that result from a protein-protein interaction. This strategy relies on the targeting of proteins to specific subcellular locations upon a protein binding, e.g. cytoplasm to nucleus, cytoplasm to plasma membrane, nucleus to cytoplasm, etc. This assay might be developed by expanding upon the description in Sakai, N. et al., "Direct visualization of the translocation of the gamma-subspecies of protein kinase C in living cells using fusion protein with green fluorescent protein", *J. Cell. Biol.* 139: 1465 (1997), incorporated herein by reference. While Sakai et al. used cloned genetic material, their methods should be adaptable for use with chromosomes or large genomic DNA fragments without undue experimentation.

Functional Assay: in vivo

Figure 6:
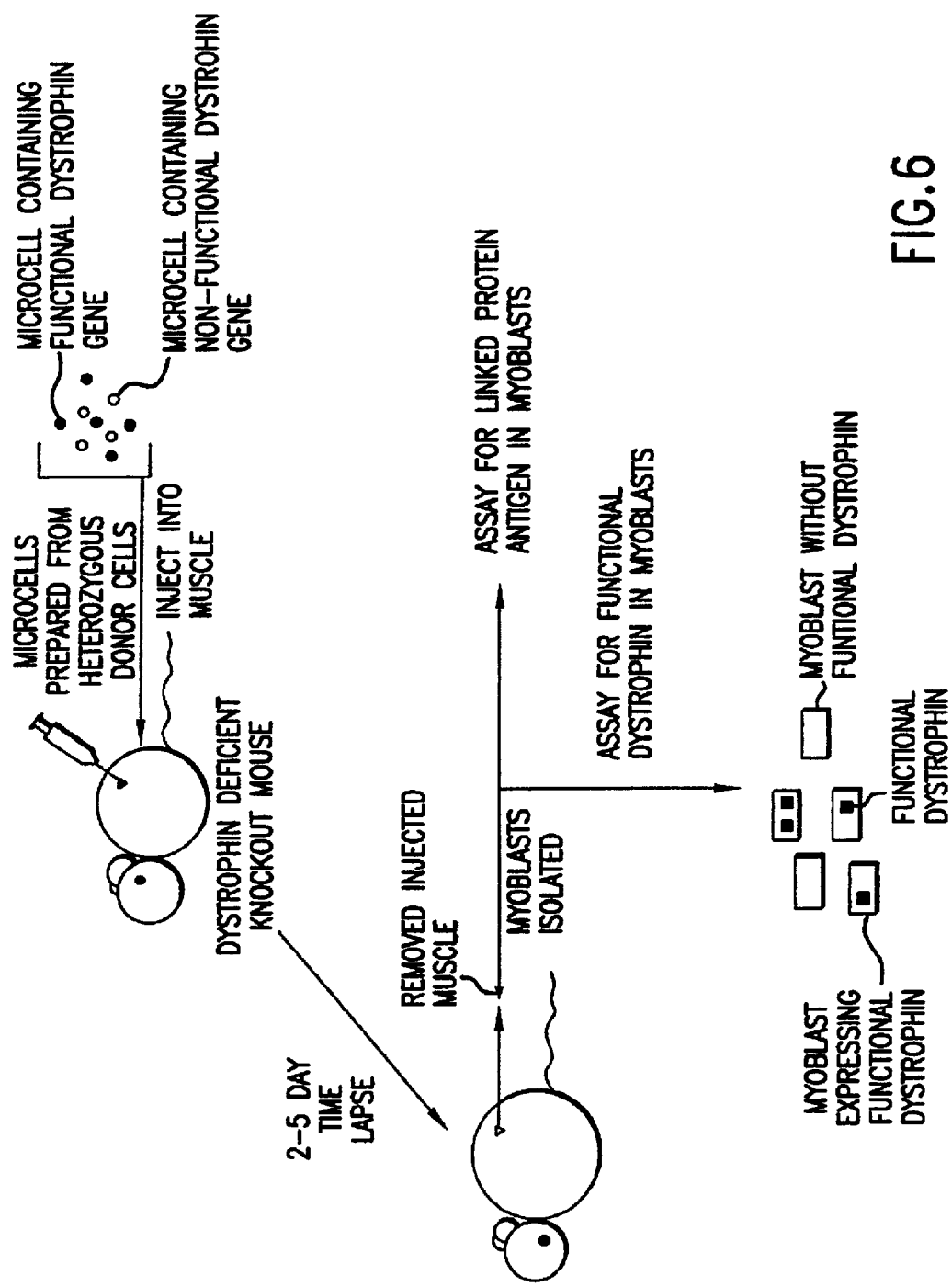
FIG. 6 depicts an in vivo assay that may be used to detect functional test protein.

Functional assays need not always be carried out in vitro. An assay to detect Duchenne dystrophy, ornithine transcarbamylase deficiency, or other disease might be performed in vivo. For such an assay, the target cells would be located inside a living organism. These target cells might be naturally deficient cells or cells rendered deficient through knockout techniques. The living organism might then be, for instance, a deficient strain of mice or a knockout mouse. Preparation of a knockout mouse for a test gene of interest may be accomplished through techniques currently employed in the art. In the case of Duchenne dystrophy the knockout mice would lack a dystrophin gene and the target cell would likely be a myoblast or hepatocyte. The transfer of the test gene to the target cells might be accomplished by injecting microcells prepared as in MMCT into an organ or tissue of the mouse such that the target cells would likely contact the microcells. After a few, approximately 2–5, days, the organ or tissue containing the target cell might be removed and immunohistochemistry employed to detect the functional expression product of the test gene and also a linked antigen from the same chromosome as the test gene. See FIG. 6 for a description of an embodiment of this assay.

A variety of other functional assays may also be developed around the properties of individual genes using techniques known in the art. These might include assays for the ability to carry out an enzymatic activity, or assays for the ability to be modified (e.g. phosphorylated) by another protein.

Functional Assays: Gain of Function Mutants

Figure 7:
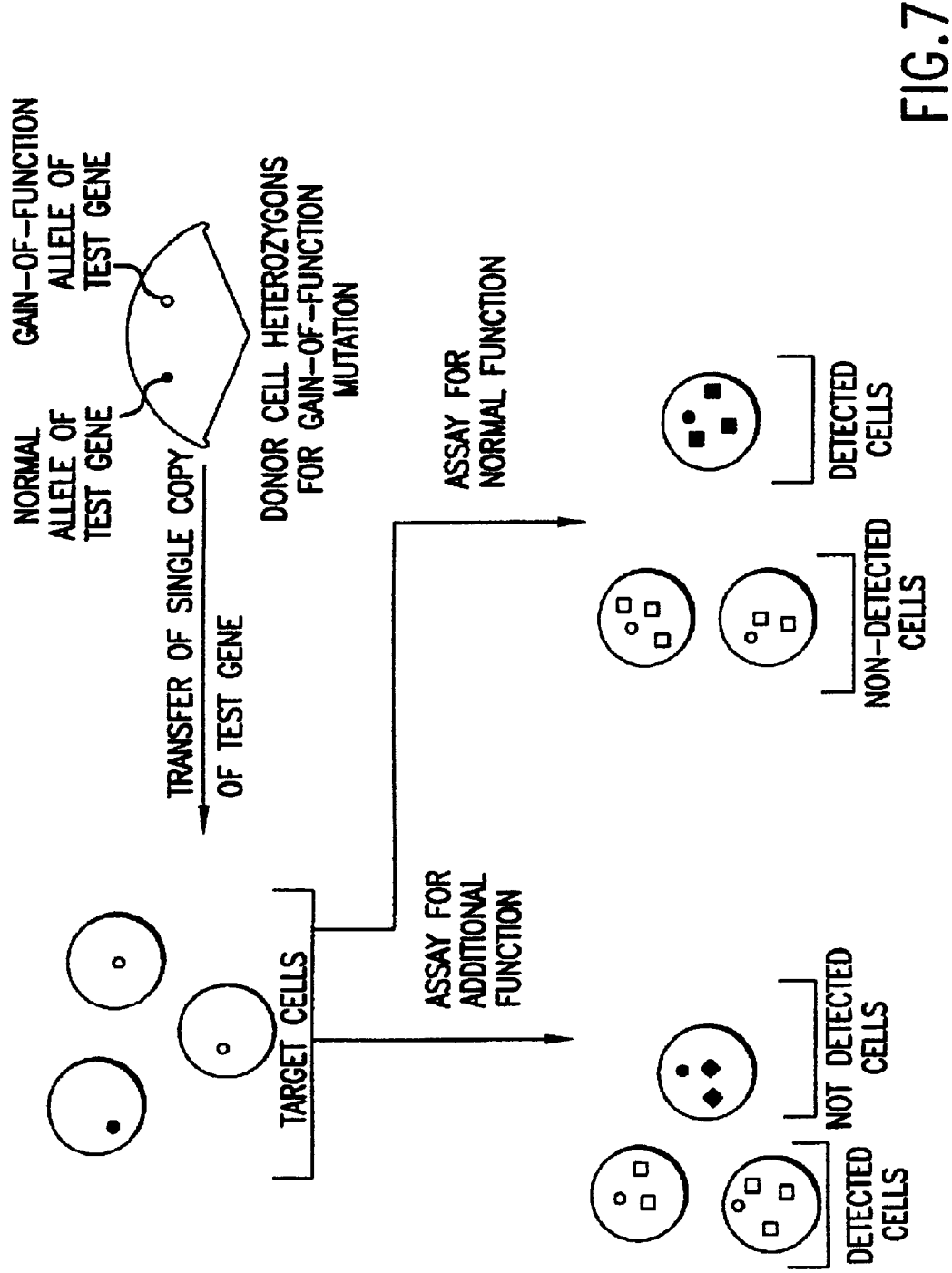
FIG. 7 shows two embodiments of the invention for gain-of-function mutations.
Figure 8:
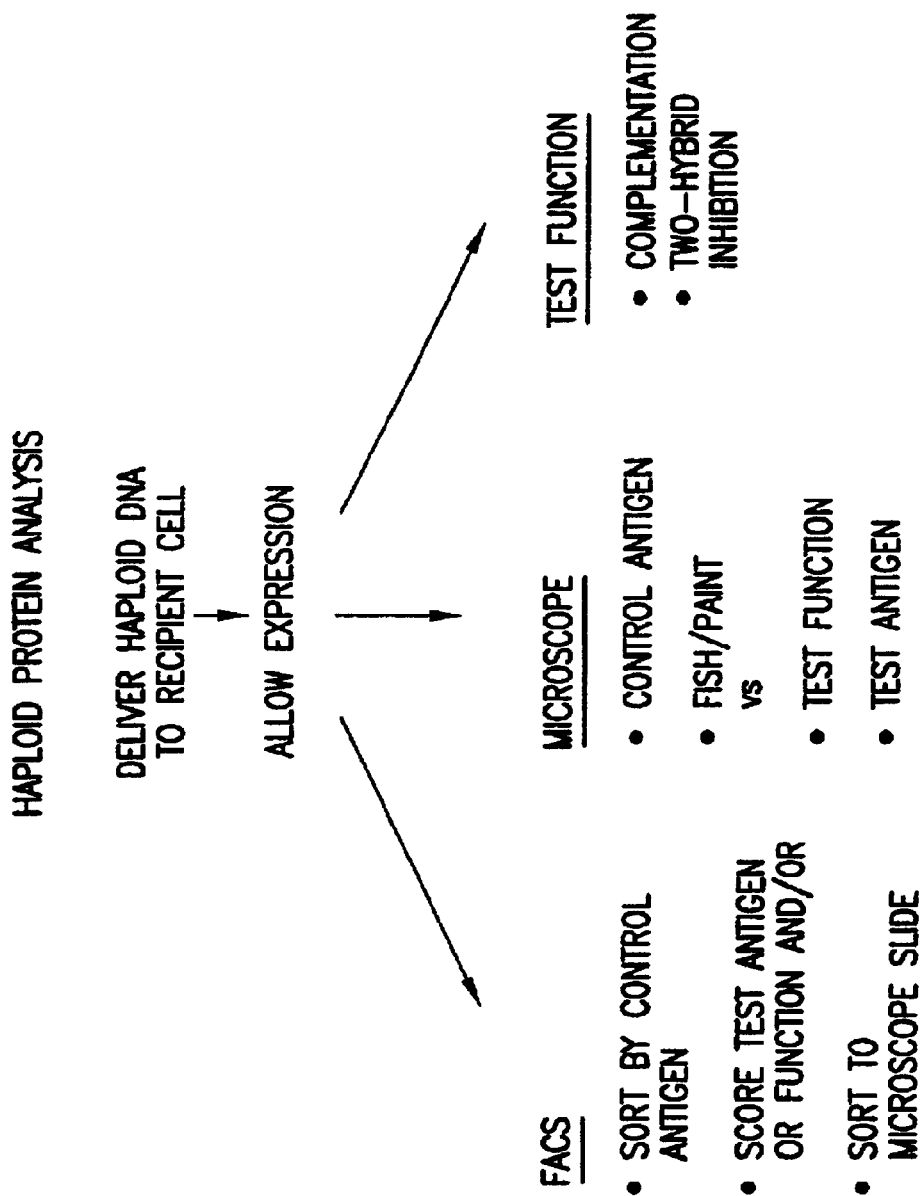
FIG. 8 shows several possible embodiments of the invention.
Figure 10A:
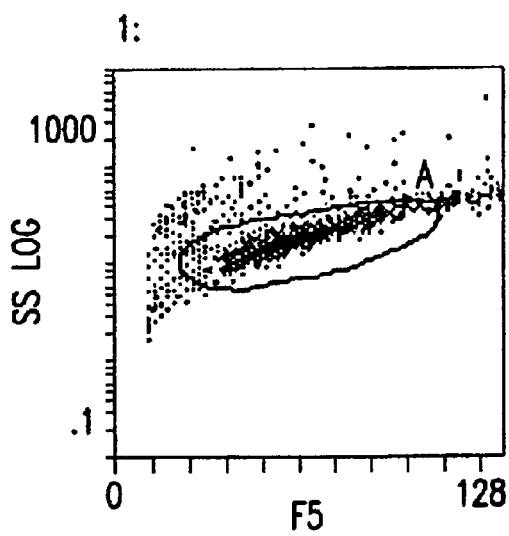
Figure 10B:
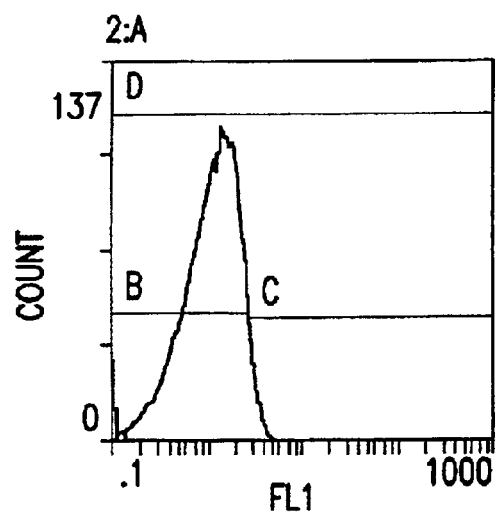
Figure 10C:
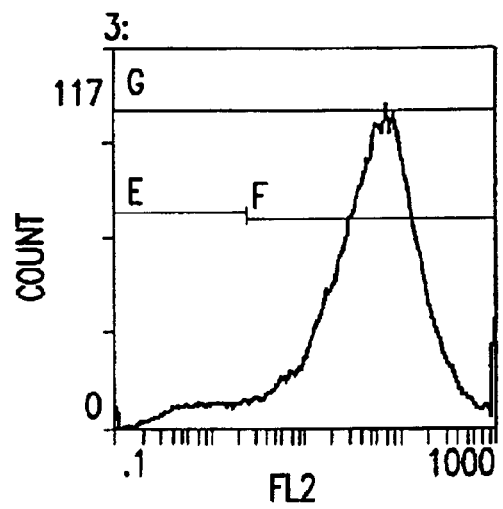
Figure 11A:
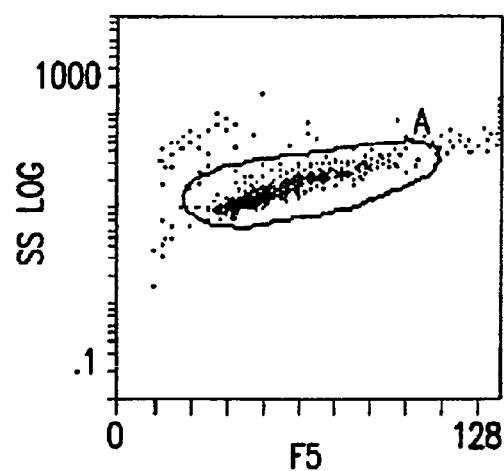
Figure 11B:
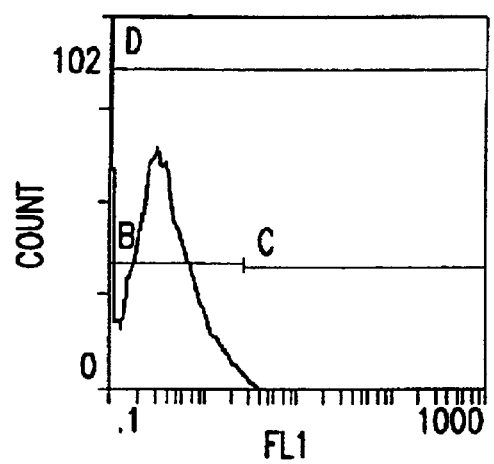
Figure 11C:
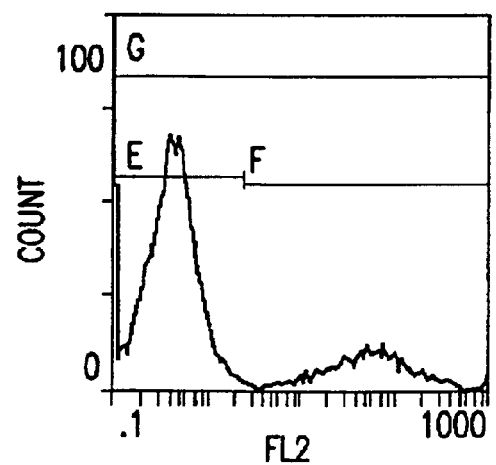

Though the functional assays described above focus on detection of loss-of-function mutations, adaptations appropriate to detect gain-of-function mutations will be understood to one skilled in the art. For example, one such assay might involve the use of target cells deficient in a particular function that may be conferred by a gain-of-function mutation. Thus, target cells in which this function is observed must have received a gain-of-function allele of the test gene while target cells in which the function is not observed must have received a wild type or functional allele of the test gene. (See FIG. 7 for a gain-of-function example.) In general, assays for gain-of-function alleles may be very similar to those for loss-of-function alleles except that expression of a protein with a particular function will indicate the presence of a mutated, rather than a wild type or functional allele of the test gene. FIG. 10 presents a general description of several of the embodiments of the present invention described above.

Heterozygous vs. Homozygous

In an embodiment of the invention, the genotype of the individual may be determined by evaluating the ratio of the number of cells expressing the wild type gene product to the number of cells expressing the test gene product. Though a variety of methods may be used to introduce a test gene into a target cell and to detect the presence of the test gene and its expression or protein function, ultimately two measurements must be made and compared to determine the genotype of the donor cell. First, a number of target cells that received the test gene must be determined. Second, a number of these target cells that also express wild type or functional protein must be determined.

If the ratio of the number of cells expressing functional or wild type protein to the number of cells that received the test gene is approximately 1:1, the donor cells are deemed to be homozygous wild type or without a deleterious mutation for the test gene. If the ratio of the number of cells expressing functional wild type protein to the number of cells that received the test gene and/or syntenic DNA is approximately 1:2, the donor cells are deemed to be heterozygous for a loss-of-function or gain-of-function mutation. If the ratio of the number of cells expressing functional or wild type protein to the number of cells that received the test gene is approximately 0:1, the donor cells are deemed to be homozygous for a loss-of-function or gain-of-function mutation.

Figure 9:
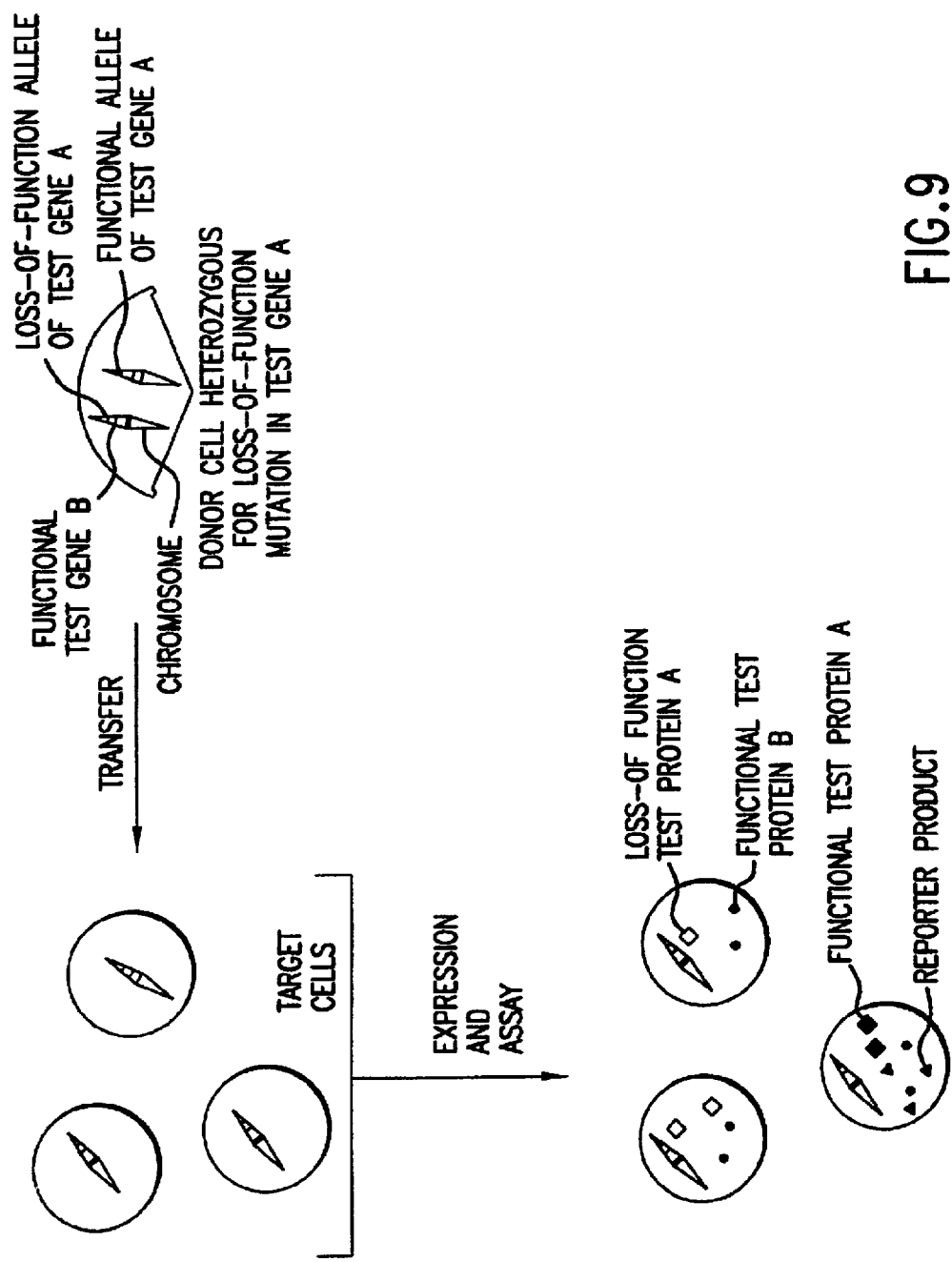
FIG. 9 shows an embodiment of the invention for more than one test gene.

Additionally, though only a single test gene is referred to throughout the specification and claims, it will be understood to one skilled in the art that more than one test gene may be transferred to from the donor cell to the target cell. (See FIG. 9 for an example of a multi-gene embodiment of this invention.) This may preferably be accomplished through simultaneous transfer of the multiple test genes. The target cells should be naturally or artificially capable of expressing all test genes and all test proteins should be detectable and distinguishable in the target cells. The target cells may be assayed for the presence of the each test gene separately, or, if the test genes are linked, one assay may confirm the presence of all test genes. Finally, different functional or immunological assays may be performed to detect functional or wild type expression for each test gene separately or, if the genes function in concert, a single assay that requires functional or wild type expression of each gene may be employed. Such an assay might prove valuable where one needs only to determine whether a loss-of-function or gain-of-function mutation exists in one of a set of genes, rather than in a single, specific gene.

Many of the assays described above are automatable for more rapid and efficient testing. For instance, haploid target cells may be subjected to all of the steps of the assay for the test gene and of the assay for the protein except the final visualization or counting step. Automated panning, immunoprecipitation or magnetic bead steps might be used to separate those cells expressing a linked surface antigen. The counting step might then be performed on such target cells placed on a microscopic slide via an automated counting system. This system might be similar to those currently used in hospitals and labs for blood counts. It might alternatively be performed by an automated FACS system. In order to obtain results as quickly as possible using an automated system or any other method of detection or calculation, a method using lymphoblasts as donor cells and MMCT as the transfer method might be optimal, as such a method should only require around nine days before obtaining results.

Additionally, the method described above it all of its permutations may be adapted for use in medical or veterinary testing for any disease mentioned herein, or any other disease resulting from or related to a loss-of-function mutation or a gain-of-function mutation. Such medical or veterinary testing may be conducted, inter alia, in diagnostic or professional laboratories by technicians, in hospital laboratories, or in medical or veterinary offices. Steps of the method of this invention may be selected so as to be amendable to the test location. For instance, steps that require less precise conditions and procedures or that take less time might be most appropriate for use in medical or veterinary offices, while more rigorous conditions and procedures can often be performed in a diagnostic laboratory. Additionally, steps may be selected so as to maximize the clinical value of the information received while minimizing the cost of testing. Steps may also be selected to provide the most comprehensive amount of information about a mutation or potential mutation regardless of cost.

The method of the present invention might also be embodied in kits. These kits may be designed for research, medical, veterinary or other uses. The precise steps of the above methods may be selected so that the reagents are amenable to commercial production for a kit, so that the reagents are stable enough to be shipped and maintain a reasonable shelf-life, or so that the kit is easy to use. Other considerations specific to the test gene and the proposed use of the kit may influence the choice of method steps.

Although only preferred embodiments of the invention are specifically described above, it will be appreciated that modifications and variations of the invention are possible without departing from the spirit and intended scope of the invention.

The following non-limiting examples are provided to more clearly illustrate the aspects of the invention and are not intended to limit the scope of the invention.

EXAMPLES

Example 1
Selection of a Test Gene

Familial hypercholesterolemia results from a heterozygous or homozygous loss-of-function mutation in the LDLR gene. Approximately 1 in 500 individuals in the general population are heterozygous for the loss-of-function mutation. Molecular confirmation of the diagnosis is not readily available. This presents a problem particularly in regards to the certainty of diagnosis and counseling of relatives of the disease sufferers. Thus, application of the methods of the invention to this disease may result in more accurate detection and better counseling of those predisposed to or with familial hypercholesterolemia. It may also result in more efficient and cost-effective diagnosis. Finally, application of the methods of this invention to study familial hypercholesterolemia in the laboratory may lead to a better understanding of the disease or more effective or specific treatments. Thus, the LDLR gene is an excellent test gene for the method of this invention.

Example 2
Selection of Donor Cells

As described above, biopsies and the products of other invasive methods have been previously used in MMCT and other cell fusion techniques to produce haploid hybrid cells. Obtaining such samples is costly, time-consuming and sometimes uncomfortable for the patient. To avoid such problems, lymphoblasts were selected as the donor cells for these experiments. Lymphoblasts are readily obtainable from whole blood, the collection of which is routine and minimally invasive. Use of whole blood also save times and money, since a portion of the sample may be used for other medical testing. Lymphoblasts may be obtained from whole blood by a variety of methods, including centrifugation in a Ficoll gradient. Finally, lymphoblasts are a useful donor cell for the LDLR gene because they constitutively express the gene. Thus, there is no necessity to reactivate a non-active gene before it may be expressed in the target cells.

Example 3
Selection of Target Cells and Test Gene Transfer Method

CHO cells were selected as the target cells because they are a hardy, readily available, and well-characterized cell line. Additionally, CHO cells do not express LDLR, but have been shown to be capable of expressing the fully functional protein in Corsetti et al. (1991).

MMCT was selected as the test gene transfer method, since it represents the most efficient means to date of transferring a chromosome or chromosome fragment from one cell to another. Transfer of an entire chromosome was desirable to preserve linkage of the LDLR gene to the gene for the surface antigen ICAM-1.

MMCT largely as described in Killary et al., and partially as further described in Example 4 below was used to transfer human Chromosome 19 comprising the wild type LDLR gene to CHO cells. The CHO cells were then incubated with dil-LDL as in Corsetti et al. After incubation, CHO cells with Chromosome 19 showed intense, cytoplasmic staining on microscope slides while a control group that did not receive Chromosome 19 showed no staining. Fluorescence was also determined by FACS (FIGS. 10A–10D). Finally, a mixture of 80% Chromosome 19 negative CHO cells and 20% Chromosome 19 positive CHO cells was subjected to FACS analysis. As expected, approximately 20% of the cells were fluorescent while 80% were not FIGS. 11A–11D. The results confirm that CHO cells can express the test gene and perform the functional assay.

Example 4

Microcell Mediated Chromosome Transfer of Chromosome 19

Human Chromosome 19 was transferred from lymphoblasts to CHO cells using microcell mediated transfer techniques generally as described in Killary et. al. (1995). However, some variations of this method were used. The incorporation by reference of the Killary paper and the descriptions here are not intended to limit the invention to the specific embodiments described. Other possible variations of MMCT or other potential transfer techniques will be understood by one skilled in the art and a nonexhaustive list is provided above.

Figure 12:
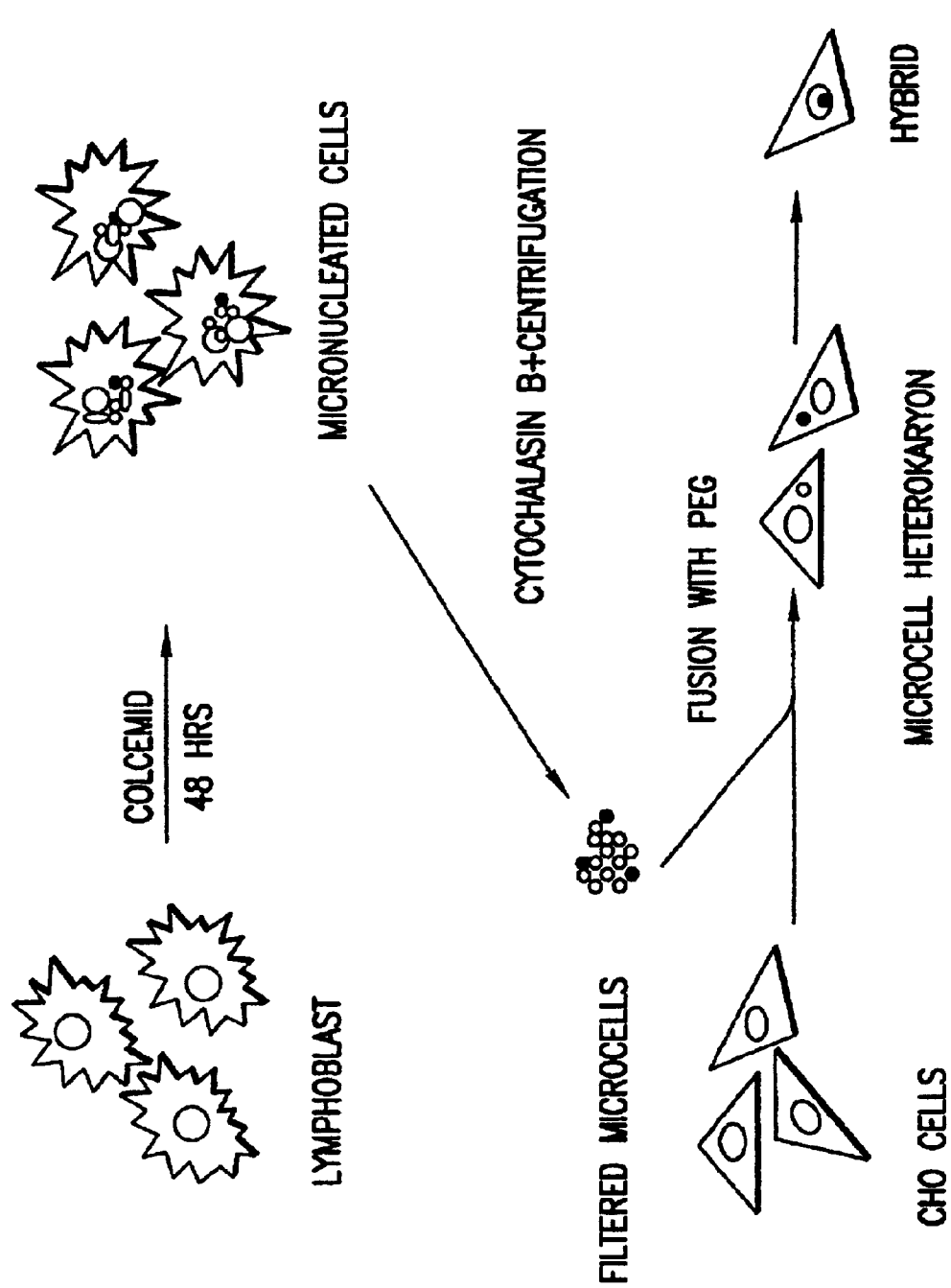
FIG. 12 shows a variation of MMCT used in the preferred embodiment in which LDLR is the test gene.
Figure 14A:
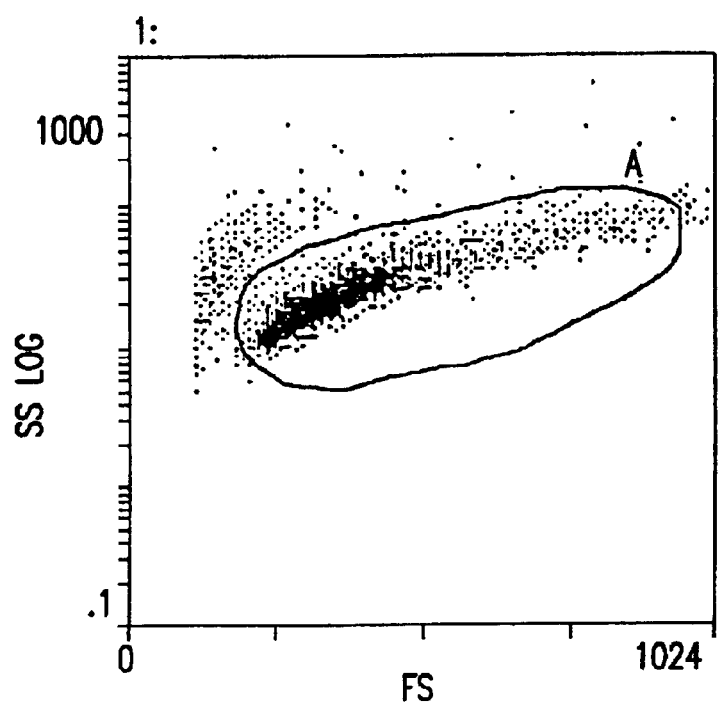
Figure 14B:
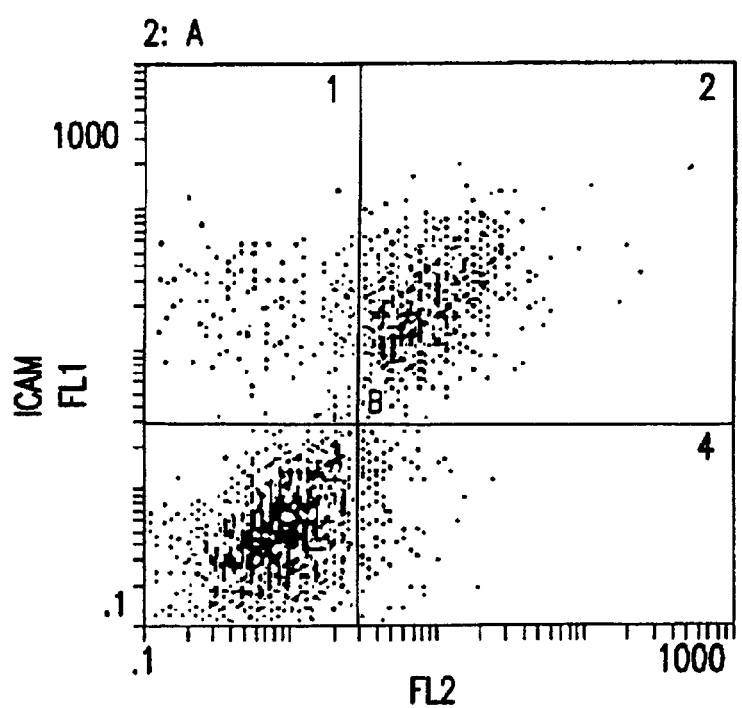
Figure 14C:
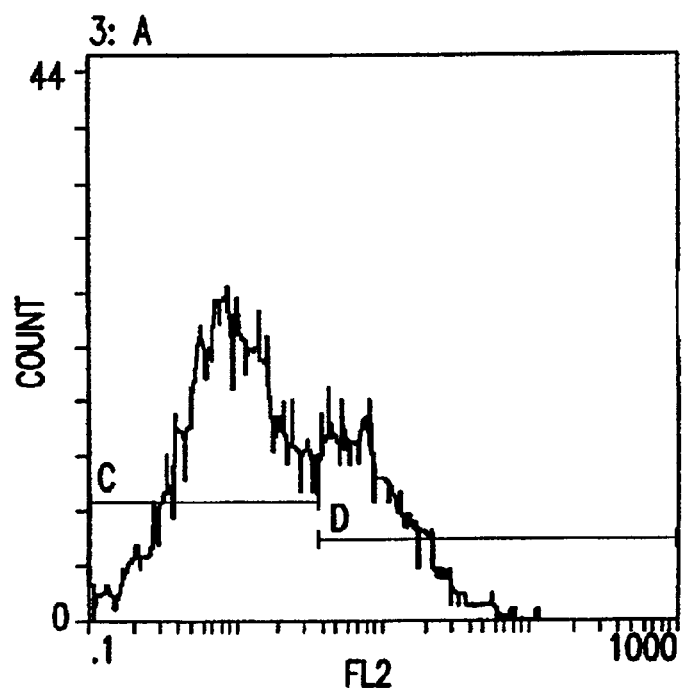
Figure 14D:
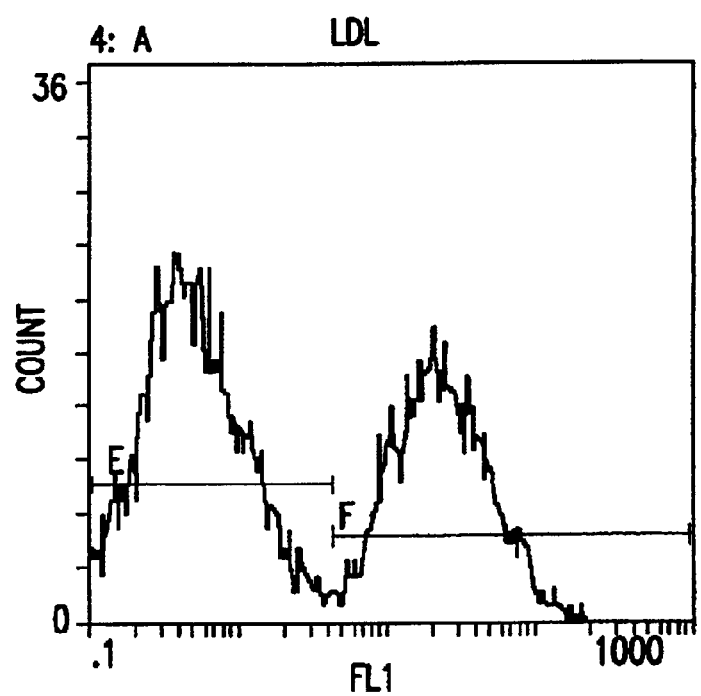

Briefly, lymphocytes were isolated from whole blood using a Ficoll hypaque gradient. Lymphoblasts were prepared by stimulating the lymphocytes with phytohemagglutinin, followed by treatment with 1 μg/ml Colcemid for 48 hours to achieve prolonged metaphase arrest and induce micronucleation. Under these conditions, 36–56% of donor cells contained micronuceli. Donor cells were then plated onto thin plastic sheets, rounded at one end to fit the bottoms of 50 ml centrifuge tubes (termed "bullets"). Bullets were pretreated with Concanavalin A as described in Killary and Fournier (Methods 8:234–246, 1995) to adhere micronucleate populations in suspension onto plastic bullets. The plastic bullets with the cells adherent to the side were then placed vertically in a centrifuge tube (two bullets/tube) in medium containing cytochalasin B (5 ug/ml). Centrifugation in the presence of cytochalasin B results in the enucleation of micronucleate populations and resultant enucleate whole cells (karyoplasts) and microcells pellet at the bottom of the centrifuge tube. The resulting pellets were then filtered through 5 micron and 3 micron nucleopore filters according to the method of McNeill and Brown (PNAS 77:5394–5398 (1980)) to select for microcells containing single human chromosomes and to remove whole cells that failed to enucleate and karyoplasts that contaminate the preparation. Under the conditions of MMCT, most target cells will not take up any chromosome. Only about 1 in 1000 to 1 in 10,000 target cells will take up a copy of Chromosome 19. (See results of Example 6). Very rarely, a target cell will take up more than one copy of Chromosome 19, but such events are so infrequent as to be irrelevant for the purposes of these experiments. After filtration, cells containing approximately one chromosome or chromosome fragment were retained. FIG. 12 depicts MMCT as used in this example.

MMCT was performed for several peripheral blood lymphocyte samples, some from normal individuals, some from individuals known to be heterozygous for a loss-of-function mutation in LDLR, and some from individuals known to be homozygous for a loss-of-function mutation in LDLR. These samples representing three genotypes for the LDLR were then used in all of the examples described below.

Example 5

Incubation of Selected Target Cells with Labeled LDL

After MMCT, the selected CHO target cells were cultured for 48 hours then allowed to take up fluorescently labeled dil-LDL.

Example 6

Detection of the Test Gene Through Labeled ICAM-1

The target CHO cells were next assayed for surface expression of ICAM-1. ICAM-1 has been shown to be linked to LDLR. Target cells expressing ICAM-1 were assumed to have received the LDLR gene and to be capable of normal protein expression.

ICAM-1 expression was detected by incubating the cells with a FITC-labeled anti-ICAM-1 antibody. Cells positive for ICAM-1 were visualized using fluorescent microscopy. Cells positive for ICAM-1 were then sorted from the remaining target cells by FACS. Approximately 250,000–2,300,000 cells were FACS-sorted. Of these only 0.08–0.7% were ICAM-1 positive.

The low percentage of ICAM-1 positive cells is likely due to the low efficiency of Chromosome 19 uptake than to any problems with cell sorting. Preliminary tests were performed to determine whether FITC-labeled ICAM-1 expressing cells were detectable and thus sortable through FACS analysis. Mouse L-cells transfected with a construct expressing ICAM-1 and nontransfected cells were incubated with FITC-labeled anti-ICAM-1 antibody. After incubation, cells not expressing ICAM-1 were easily distinguished from cells expressing the molecule by FACS analysis. (See FIGS. 13A1–13A5 and 13B1–13B5.) Thus, FACS is an efficient method for sorting of ICAM-1 expressing cells from non-ICAM expressing cells.

Example 7

Detection of Cytoplasmic Labeled LDL and ICAM-1 Expression

Spontaneous loss of chromosomal material can occur in CHO cells which originally expressed human chromosome 19. LDL Uptake and ICAM-1 expression was also performed using FACS analysis on the cells (FIGS. 14A–14E). 54% of the cells were negative for both LDL uptake and ICAM-1 expression while 26.2% of the cells labeled for both. Only a very small proportion of the cells, 65 and 13% were, express either ICAM-1 or exhibit LDL uptake.

LDL uptake and ICAM-1 expression was performed on CHO cells expressing LDLR genes from a normal donor as described above (FIGS. 15A1–15A6 and 15B1–15B5). The majority of the cell population was positive for both ICAM-1 and LDL. For individuals heterozygous for a loss-of-function mutation in the LDLR gene, a portion of the target cell population was positive for both ICAM-1 and LDL, but another portion was positive only for ICAM-1 (FIGS. 16A1–16A5, 16B1 and 15B2). For samples from an individual homozygous for a loss-of-function mutation in the LDLR, most of the target cell population was positive only for ICAM-1 (FIGS. 17A1–17A5 and 17B1–17B5). The FACS profile of the homozygous individual were similar to that of the negative control cells (FIGS. 18A1–18A5 and 18B1–18B6).

Example 8

Interpretation of the Ratio of LDL Positive Cells to ICAM-1 Positive Cells

In illustrative slides prepared and visualized as described in Example 7, for CHO cells that received the LDLR gene from normal donor, every single ICAM-1 positive cell was also positive for the LDLR. Thus when the ratio of cells expressing the wild type or functional test gene to the total number of target cells that received the test gene is approximately 1:1, the donor cells may be deemed to be normal or without a deleterious mutation for the test gene.

For CHO cells that received the LDLR gene from a heterozygous loss-of-function donor and positively expressing ICAM-1, a mixture of LDLR positive and LDLR negative cells were detected. The ratio of cells expressing the LDLR to the number expressing ICAM-1 was roughly 1:2. Thus when the ratio of cells expressing the wild type or functional test gene to the total number of target cells that received the test gene is 1:2, the donor cells may be deemed to be heterozygous for the loss-of-function mutation.

Finally, for CHO cells that received the LDLR gene from a homozygous loss-of-function donor and positively expressing ICAM-1, not a single LDLR positive cell was observed. Thus when the ratio of cells expressing the wild type or functional test gene to the total number of target cells that received the test gene is approximately 0:2, the donor cells may be deemed to be homozygous for the loss-of-function mutation.

We claim:

1. A method for determining whether an individual is wild type, heterozygous for a known genetic disorder, or homozygous for a known genetic disorder caused by a loss-of-function mutation in a test gene of interest comprising:
   (a) obtaining a sample of genetic material from the individual, said sample containing the test gene of interest,
   (b) separating the genetic material into haploid sets wherein each haploid set contains a single copy of the test gene of interest, wherein the test gene of interest is associated with the known disorder;
   (c) transferring the single copies of the test gene of interest to a population of target cells, which provide for expression therein of the test gene resulting in a detectable test gene product, the test gene product having a known function, wherein the expressed test gene product is either functional or non-functional, wherein each single copy of the test gene is transferred to a single target cell;
   (d) monitoring the population of target cells to identify a number of target cells having the test gene;
   (e) monitoring the population of target cells to identify a number of target cells having a functional test gene product;
   (f) monitoring the population of target cells to identify target cells having a non-functional test gene product, wherein presence of the non-functional test gene product is an indication of a loss-of-function mutation in the test gene of interest; and
   (g) comparing the number of target cells identified in (e) with the number of target cells identified in (d) to obtain a ratio of the number of target cells having a functional test gene product to the number of target cells having the test gene;
   wherein a ratio of approximately 1:1 is an indication that the individual is wild type, a ratio of approximately 1:2 is an indication that the individual is heterozygous for the genetic disorder, and a ratio of approximately 0:1 is an indication that the individual is homozygous for the genetic disorder.

2. The method of claim 1, wherein the loss-of-function mutation cause a genetic disorder in the individual.

3. The method of claim 1, wherein the loss-of-function mutation results in a known genetic disorder in offspring of the individual.

4. The method of claim 1, wherein the known disorder is selected from the group consisting of breast and ovarian cancer, familial hypercholesterolemia, hereditary nonpolyposis colon cancer (HNPCC), neurofibromatosis, polyposis of the colon, Duchenne dystrophy, cystic fibrosis, Li Fraumeni disease, tuberous sclerosis, Gorlin syndrome, Von Hippel-Lindau disease, porphyrias, osteogenesis imperfecta, Marfan's disease, polycystic kidney disease, hemophilia, SCID, Rett syndrome, lysosomal diseases, and ornithine transcarbamylase (OTC) deficiency.

5. The method of claim 4, wherein the test gene is the low density lipoprotein receptor gene.

6. The method of claim 1, wherein the sample of genetic material containing the test gene is obtained from donor cells.

7. The method of claim 6, wherein the donor cells are human.

8. The method of claim 6, wherein the donor cells are lymphoblasts.

9. The method of claim 6, wherein the separation of the genetic material into haploid sets is performed within the donor cell.

10. The method of claim 1, wherein the separation of the genetic material into haploid sets is a result of a transfer method.

11. The method of claim 6, wherein the separation of the genetic material into haploid sets occurs after removal of the genetic material from the donor cells.

12. The method of claim 1, wherein the target cells are selected from the group consisting of mammalian cells, insect cells and yeast cells.

13. The method of claim 12, wherein the target cells are Chinese Hamster Ovary cells.

14. The method of claim 1, wherein the single copies of the test gene of interest are located on a chromosome or chromosome fragment.

15. The method of claim 5, wherein the low density lipoprotein receptor gene is located on Chromosome 19.

16. The method of claim 1, wherein the single copies of the test gene of interest are transferred to the target cells through microcell mediated chromosome transfer.

17. The method of claim 1, wherein the single copies of the test gene of interest are transferred to the target cells through electroporation.

18. The method of claim 1, wherein the single copies of the test gene of interest are transferred to the target cells through liposome-mediated transfer.

19. The method of claim 1, wherein the single copies of the test gene of interest are transferred to the target cells through somatic cell fusion.

20. The method of claim 1, wherein the single copies of the test gene of interest are transferred to the target cells through fusion of sperm cells with the target cells.

21. The method of claim 1, wherein the target cells naturally provide for the expression therein of the test gene.

22. The method of claim 1, wherein the test gene product is a test protein.

23. The method of claim 1, wherein the target cells are manipulated to provide for expression therein of the test gene.

24. The method of claim 1, wherein the target cells have been rendered incapable of expressing the ortholog of the test gene or other functionally interfering protein so as to allow detection of the detectable test gene product.

25. The method of claim 1, wherein the target cells lack the function or functions provided by expression of a functional form of the test gene product.

26. The method of claim 1, wherein the target cells are monitored to determine whether a single copy of the test gene of interest was successfully transferred to the cells.

27. The method of claim 26, wherein the target cells are monitored using an assay.

28. The method of claim 27, wherein the assay is fluorescence in situ hybridization.

29. The method of claim 27, wherein the assay is chromosome paint.

30. The method of claim 27, wherein the assay detects the presence of a gene linked to the test gene.

31. The method of claim 27, wherein the assay is an assay for an expression product of a gene linked to the test gene.

32. The method of claim 30 or 31, wherein the linked gene and the test gene are naturally linked on a chromosome.

33. The method of claim 31, wherein the expression product of the linked gene is a protein.

34. The method of claim 33, wherein the protein is a surface protein.

35. The method of claim 34, wherein the assay comprises detection of the surface protein by a fluorescently tagged antibody that detects said surface protein.

36. The method of claim 35, wherein the surface protein is ICAM-1.

37. The method of claim 26, wherein the target cells to which a single copy of the test gene of interest was successfully transferred are separated from target cells to which a single copy of the test gene of interest was not successfully transferred by fluorescence activated cell sorting.

38. The method of claim 1, wherein monitoring the population of target cells to identify the number of target cells having a functional test gene product and monitoring the population of target cells to identify the number of target cells having a nonfunctional gene product is accomplished through a functional assay for the test gene product.

39. The method of claim 38, wherein the test gene product is a receptor.

40. The method of claim 39, wherein the functional assay comprises:

preparing a fluorescently labeled ligand capable of interaction with the receptor if the receptor is functional;

exposing the target cells to the labeled ligand in such a manner as to allow interaction of the ligand with the receptor if the receptor is functional;

detecting cells in which the ligand has interacted with the receptor.

41. The method of claim 40, wherein microscopy is used to detect cells in which the ligand has interacted with the receptor.

42. The method of claim 38, wherein the functional assay comprises a test for restoration of function in functionally deficient target cells.

43. The method of claim 38, wherein the functional assay comprises a two-hybrid assay or a two-hybrid inhibition assay.

44. The method of claim 22, wherein monitoring the population of target cells to identify the number of target cells having a functional test gene product and monitoring the population of target cells to identify the number of target cells having a nonfunctional test gene product is accomplished through an immunological assay for the test gene product.

45. The method of claim 44, wherein the immunological assay comprises detection of the test gene product with an antibody specific for the test protein.

46. The method of claim 4, wherein the test gene is any gene known to cause a genetic disorder.

* * * * *